United States Patent [19]

Himmelsbach et al.

[11] Patent Number: 5,880,284
[45] Date of Patent: Mar. 9, 1999

[54] CYCLIC UREA DERIVATIVES, PHARMACEUTICAL COMPOSITIONS CONTAINING THESE COMPOUNDS AND PROCESSES FOR PREPARING THEM

[75] Inventors: Frank Himmelsbach, Mittelbiberach; Volkhard Austel, Biberach; Günter Linz, Mittelbiberach; Helmut Pieper, Biberach; Brian Guth, Warthausen; Thomas Müller, Edewecht; Johannes Weisenberger, Biberach, all of Germany

[73] Assignee: Dr. Karl Thomae GmbH, Biberach an der Riss, Germany

[21] Appl. No.: 864,528

[22] Filed: May 28, 1997

Related U.S. Application Data

[62] Division of Ser. No. 120,008, Sep. 10, 1993, Pat. No. 5,681,841.

[30] Foreign Application Priority Data

| Sep. 11, 1992 | [DE] | Germany | 4230470.9 |
| Jan. 26, 1993 | [DE] | Germany | 4302052.6 |
| Mar. 22, 1993 | [DE] | Germany | 4309213.6 |

[51] Int. Cl.$^6$ ................................................. C07D 453/02
[52] U.S. Cl. ................................. 546/133; 546/112
[58] Field of Search .......................... 546/112, 133

[56] References Cited

U.S. PATENT DOCUMENTS

| 3,365,450 | 1/1968 | Lunsford et al. | 546/208 X |
| 4,744,813 | 5/1988 | Teach | 514/322 |
| 5,276,049 | 1/1994 | Himmelsbach et al. | 514/392 |
| 5,401,750 | 3/1995 | Varasi et al. | 546/112 |

FOREIGN PATENT DOCUMENTS

| 0402989 | 12/1990 | European Pat. Off. . |
| 0503548 | 9/1992 | European Pat. Off. . |
| 1394708 | 10/1962 | France . |
| 1516714 | 11/1962 | France . |
| 1139985 | 7/1967 | United Kingdom . |
| 9200282 | 1/1992 | WIPO . |
| 9210192 | 6/1992 | WIPO . |

*Primary Examiner*—Fiona T. Powers
*Attorney, Agent, or Firm*—R.P. Raymond; M-E. M. Devlin; A.R. Stempel

[57] ABSTRACT

The invention relates to cyclic urea derivatives of general formula I

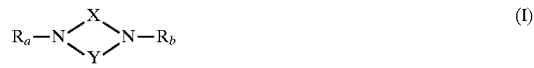

wherein $R_a$, $R_b$, X and Y are defined as in claim 1, the tautomers, stereoisomers and salts thereof, particularly the physiologically acceptable salts thereof with inorganic or organic acids or bases, which have valuable pharmacological properties, preferably aggregation inhibiting effects, and to drugs containing the compounds and processes for preparing them.

7 Claims, No Drawings

CYCLIC UREA DERIVATIVES, PHARMACEUTICAL COMPOSITIONS CONTAINING THESE COMPOUNDS AND PROCESSES FOR PREPARING THEM

This is a division of application Ser. No. 08/120,008, filed Sep. 10, 1993 now U.S. Pat. No. 5,681,841.

The invention relates to cyclic urea derivatives of general formula

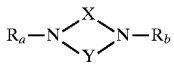 (I)

the tautomers and stereoisomers and the salts thereof, particularly the physiologically acceptable salts thereof with inorganic or organic acids or bases, which have, inter alia, valuable pharmacological properties, preferably aggregation-inhibiting effects,
with the exception of
1-(4-amidino-phenyl)-3-[4-(2-carboxy-ethyl)-cyclohexyl]-imidazolidin-2-one,
1-(4-amidino-phenyl)-3-[4-(2-methoxycarbonyl-ethyl)-cyclohexyl]-imidazolidin-2-one,
1-(4-cyano-phenyl)-3-[4-(2-methoxycarbonyl-ethyl)-cyclohexyl]-imidazolidin-2-one,
1-(4-amidino-phenyl)-3-[4-[2-(5-tetrazolyl)-ethyl]-phenyl]-imidazolidin-2-one,
1-(4-aminomethyl-cyclohexyl)-3-[4-(2-carboxy-ethyl)-phenyl]-imidazolidin-2-one,
1-(4-aminomethyl-cyclohexyl)-3-[4-(2-methoxycarbonyl-ethyl)-phenyl]-imidazolidin-2-one,
4-(4'-amidino-4-biphenylyl)-1-(2-carboxy-ethyl)-3-phenyl-3H-imidazol-2-one,
4-(4'-amidino-4-biphenylyl)-1-(2-methoxycarbonyl-ethyl)-3-phenyl-3H-imidazol-2-one,
4-(4'-cyano-4-biphenylyl)-1-(2-methoxycarbonyl-ethyl)-3-phenyl-3H-imidazol-2-one,
4-[4'-amidino-4-biphenylyl]-1-(2-carboxy-ethyl)-3-phenyl-imidazolidin-2-one,
4-(4'-amidino-4-biphenylyl)-1-(2-methoxycarbonyl-ethyl)-3-phenyl-imidazolidin-2-one,
1-(4'-amidino-4-biphenylyl)-3-(2-ethoxycarbonyl-ethyl)-3H-imidazol-2-one,
1-(4'-cyano-4-biphenylyl)-3-(2-ethoxycarbonyl-ethyl)-3H-imidazol-2-one,
1-(4'-amidino-4-biphenylyl)-3-(2-ethoxycarbonyl-ethyl)-imidazolidin-2,4-dione,
1-(4'-cyano-4-biphenylyl)-3-(2-ethoxycarbonyl-ethyl)-imidazolidin-2,4-dione,
1-(4'-amidino-4-biphenylyl)-3-(2-ethoxycarbonyl-ethyl)-3,4,5,6-tetrahydro-1H-pyrimidin-2-one,
1-(4'-cyano-4-biphenylyl)-3-(2-ethoxycarbonyl-ethyl)-3,4,5,6-tetrahydro-1H-pyrimidin-2-one,
2-(4-amidino-phenyl)-4-[4-(2-isopropyloxycarbonyl-ethyl)-phenyl]-5-methyl-4H-1,2,4-triazol-3-one,
4-[4-(2-Isopropyloxycarbonyl-ethyl)-phenyl]-2-(4-methoxy-carbonylamidino-phenyl)-5-methyl-4H-1,2,4-triazol-3-one,
1-(4-amidino-phenyl)-3-[4-(2-ethoxycarbonyl-ethyl)-phenyl]-3H-imidazol-2-one,
1-(4-ethoxycarbonylamidino-phenyl)-3-[4-(2-ethoxycarbonyl-ethyl)-phenyl]-3H-imidazol-2-one,
1-(4-ethoxycarbonylamidino-phenyl)-3-[4-(2-ethoxycarbonyl-ethyl)-phenyl]-imidazolidin-2-one,
1-(4-methoxycarbonylamidino-phenyl)-3-[4-(2-methoxycarbonyl-ethyl)-cyclohexyl]-imidazolidin-2-one,
4-[4-(2-isobutyloxycarbonyl-ethyl)-phenyl]-2-(4-methoxy-carbonylamidino-phenyl)-5-methyl-4H-1,2,4-triazol-3-one,
2-(4-amidino-phenyl)-4-[4-(2-isobutyloxycarbonyl-ethyl)-phenyl]-5-methyl-4H-1,2,4-triazol-3-one,
1-(1-amino-5-indanyl)-3-[4-(2-carboxy-ethyl)-phenyl]-imidazolidin-2-one,
1-(1-amino-5-indanyl)-3-[4-(2-methoxycarbonyl-ethyl)-phenyl]-imidazolidin-2-one,
2-(4-amidino-phenyl)-5-ethyl-4-[4-(2-isopropyloxycarbonyl-ethyl)-phenyl]-4H-1,2,4-triazol-3-one,
1-(4-amidino-phenyl)-3-[4-(2-isopropyloxycarbonyl-ethyl)-phenyl]-4-methyl-3H-imidazol-2-one,
1-(4-amidino-phenyl)-3-[4-(2-isopropyloxycarbonyl-ethyl)-phenyl]-3H-imidazol-2-one,
1-(4-amidino-phenyl)-3-[4-(2-isopropyloxycarbonyl-ethyl)-phenyl]-imidazolidin-2,4-dione,
2-(4-amidino-phenyl)-4-[4-(2-carboxy-ethyl)-phenyl]-5-trifluoromethyl-4H-1,2,4-triazol-3-one and
3-(4-cyano-phenyl)-1-(4-ethoxycarbonyl-butyl)-3H-imidazo-[4,5-b]pyridin-2-one,
pharmaceutical compositions containing these compounds, the use thereof and processes for preparing them.

In general formula I above, with the proviso that at least one of conditions (i) to (ix) below must be satisfied (i) X denotes a carbimino group substituted by a cyano group at the nitrogen atom, or a 1-nitro-ethen-2,2-diyl or 1,1-dicyano-ethen-2,2-diyl group, (ii) Y denotes a $C_{5-7}$-1,2-cycloalkylene group optionally substituted by $R_c$ or $R_d$ or by $R_c$ and $R_d$, (iii) A denotes a $C_{1-5}$-aminoalkyl group or an amino, amidino or guanidino group, in which, at one of the nitrogen atoms in each of the above mentioned groups, a hydrogen atom is replaced by an $R_1$—CO—O—($R_2CR_3$)—O—CO— group, (iv) B denotes a $C_{3-7}$-cycloalkylene group optionally substituted by one or two alkyl groups, a $C_{4-5}$-cycloalkylene group optionally substituted by a group $R_c$ and which may additionally be substituted by 1 to 4 alkyl groups, and in which, in the cycloalkylene moiety, a >CH unit is replaced by a nitrogen atom, a $C_{6-8}$-cycloalkylene group optionally substituted by a group $R_c$ and which may additionally be substituted by 1 to 4 alkyl groups and in which, in the cycloalkylene moiety, a >CH unit is replaced by a nitrogen atom and additionally another >CH unit in the 4-position may be replaced by a nitrogen atom, whilst, moreover, in the above mentioned 6–8 membered rings one or two methylene groups adjacent to a nitrogen atom may each be replaced by a carbonyl group, a $C_{5-7}$-cycloalkenylene group optionally substituted by 1 or 2 alkyl groups and which may additionally be substituted by 1 or 2 methyl groups and wherein, in the cycloalkenylene moiety, a >CH unit is replaced by a nitrogen atom, a $C_{5-7}$-cycloalkylene group, wherein a >CH unit is replaced by a nitrogen atom which is attached to Group A, and in which two hydrogen atoms on the carbon skeleton are replaced by a straight-chained alkylene bridge, this bridge containing 2 to 6 carbon atoms if it replaces two hydrogen atoms on the same carbon atom or containing 1 to 5 carbon atoms if it replaces two hydrogen atoms on adjacent carbon atoms, or containing 1 to 4 carbon atoms if it replaces two hydrogen atoms on carbon atoms which are separated by a further atom, or containing 1 to 3 carbon atoms if it replaces two hydrogen atoms on carbon atoms which are separated by 2 further atoms, whilst the above groups may each be substituted by 1 or 2 alkyl groups, a $C_{1-6}$-alkylene group linked to the group C via a group W, or B together with A denotes a pyridyl group optionally substituted by one or two alkyl groups, or a piperidinyl group in which the hydrogen atom in the 1-position together with a hydrogen atom in the 2-position is replaced by a straight-chained $C_{3-4}$-alkylene group, or B together with A denotes a piperidinyl group in which the hydrogen atoms in the 1-position and the 3-position are replaced by a straight-chained $C_{2-4}$-alkylene group, or a piperidinyl group in which the hydrogen atom in the 1-position and a hydrogen atom in the 4-position are replaced by a straight-chained $C_{1-3}$-alkylene group, whilst the methylene group of an ethylene chain attached to the 4-position may be replaced by a hydroxymethylene or carbonyl group and additionally the nitrogen atom of these above mentioned bicyclic groups, which may be substituted in the carbon skeleton by 1 or 2 alkyl groups, may be completed by borane or quaternised by a benzyl group optionally substituted by one to two methoxy groups in the phenyl nucleus, (v) C denotes a $C_{1-6}$-alkylene group in which a methylene group is replaced by an oxygen or sulphur atom or by a sulphinyl, sulphonyl or NR group or wherein an ethylene group is replaced by a $CONR_5$ or $NR_5CO$ group, a 3–7-membered cycloalkylene group optionally substituted by one or two alkyl groups, a cyclohexylene group in which two carbon atoms separated by 3 bonds may additionally be linked by a straight-chained $C_{1-3}$-alkylene group, and these bicyclic groups may also be substituted by one to two alkyl groups, an indanylene, naphthylene, 1,2,3,4-tetrahydronaphthylene or benzosuberanylene group, wherein the saturated rings may each be substituted by one or two alkyl groups and the aromatic rings may each be substituted by a fluorine, chlorine, bromine or iodine atom, or by an alkyl, trifluoromethyl, hydroxy, alkoxy, alkylsulphenyl, alkylsulphinyl, alkysulphonyl or qyano group and wherein additionally, one or two methine groups may each be replaced by a nitrogen atom, a $C_{4-5}$-cycloalkylene group optionally substituted by the group $R_c$, and optionally additionally. substituted by 1 to 4 alkyl groups and wherein in the cycloalkylene moiety a >CH unit is replaced by a nitrogen atom, a $C_{6-8}$-cycloalkylene group optionally substituted by the group $R_c$ and which may additionally be substituted by 1 to 4 alkyl groups and wherein, in the cycloalkylene moiety, a >CH unit is replaced by a nitrogen atom and additionally another >CH unit located in the 4-position may be replaced by a nitrogen atom, whilst moreover in the above mentioned 6–8-membered rings one or two methylene groups adjacent to a nitrogen atom may each be replaced by a carbonyl group, a $C_{5-7}$-cycloalkenylene group optionally substituted by one or two alkyl groups and which may additionally be substituted by one or two methyl groups and wherein, in the cycloalkenylene moiety a >CH unit is replaced by a nitrogen atom, a $C_{5-7}$-cycloalkylene group wherein a >CH unit is replaced by a nitrogen atom which is attached to group A and wherein additionally two hydrogen atoms on the carbon skeleton are replaced by a straight-chained alkylene bridge, this bridge containing two to six carbon atoms if it replaces two hydrogen atoms on the same carbon atom, or containing one to five carbon atoms if it replaces two hydrogen atoms on adjacent carbon atoms, or containing one to four carbon atoms if it replaces two hydrogen atoms on carbon atoms which are separated by a further atom, or containing one to three carbon atoms if it replaces two hydrogen atoms on carbon atoms which are separated by two further atoms, whilst the above groups may each be substituted by one or two alkyl groups, or C together with A and B denotes a pyridyl or 1-(4-pyridyl)-piperidinyl group, each optionally substituted by one or two alkyl groups, or a piperidinyl group, in which the hydrogen atom in the 1-position together with a hydrogen atom in the 2-position is replaced by a straight-chained $C_{3-4}$-alkylene group, or a piperidinyl group in which the hydrogen atom in the 1-position together with a hydrogen atom in the 3-position is replaced by a straight-chained $C_{2-4}$-alkylene group, or a piperidinyl group in which the hydrogen atom in the 1-position together with a hydrogen atom in the 4-position is replaced by a straight chained $C_{1-3}$-alkylene group, whilst the methylene group of an ethylene chain bound to the 4-position may be replaced by a hydroxymethylene or carbonyl group, and additionally the nitrogen atom of these above mentioned bicyclic groups, which may be substituted by one or two alkyl groups in the carbon skeleton, may be complexed by borane or quaternised by a benzyl group optionally substituted by one to two methoxy groups in the phenyl nucleus, or C denotes a $C_{1-6}$-alkylene group and B denotes a bond, (vi) D denotes a 1,3-arylene group, an indanylene, naphthylene, 1,2,3,4-tetrahydronaphthylene or benzosuberanylene group, wherein the saturated rings may each be substituted by one or two alkyl groups and the aromatic rings may each be substituted by a fluorine, chlorine, bromine or iodine atom or by an alkyl, trifluoromethyl, hydroxy, alkoxy, alkylsulphenyl, alkylsulphinyl, alkylsulphonyl or cyano group and wherein, additionally, one or two methine groups may each be replaced by a nitrogen atom, a $C_{3-7}$-cycloalkylene group optionally substituted by one or two alkyl groups or a cyclohexylene group in which two carbon atoms separated by three bonds may additionally be linked by a straight-chained $C_{1-3}$-alkylene group, whilst these bicyclic groups may each also be substituted by one to two alkyl groups, (vii) E denotes a straight chained $C_{1-6}$-alkylene group or a straight-chained $C_{2-6}$-alkenylene group, each is substituted by a $C_{1-8}$-alkyl group, by an aryl or heteroaryl group, by an $HNR_6$ or N-phenylalkyl-$NR_6$ group or by an N-alkyl $NR_6$ group having 1 to 8 carbon atoms in the alkyl moiety, a $C_{5-7}$-cycloalkylene group optionally substituted by one or two alkyl groups and wherein a >CH unit is replaced by a nitrogen atom, a cycloalkylene group having 4 to 7 carbon atoms in the cycloalkylene moiety which is substituted by a hydroxy, amino, aryl or heteroaryl group, by a $C_{1-8}$-alkoxy or $C_{1-8}$-alkylamino group, by a dialkylamino group having a total of 2 to 10 carbon atoms, by an $HNR_6$ or N-phenylalkyl-$NR_6$ group or by an N-alkyl-$NR_6$ group having 1 to 8 carbon atoms in the alkyl moiety, or an alkylene group linked to the group D via a group W, whilst the alkylene group may additionally be substituted by one or two $C_{1-8}$-alkyl groups, by a hydroxy, amino, aryl or heteroaryl group, by a $C_{1-8}$-alkoxy or $C_{1-8}$-alkylamino group, by a dialkylamino group having a total of 2 to 10 carbon atoms, by an $HNR_6$ or N-phenylalkyl-$NR_6$ group or by an N-alkyl-$NR_6$ group having 1 to 8 carbon atoms in the alkyl moiety, (viii) F-denotes an alkoxy carbonyl group having a total of 3 to 9 carbon atoms, an $R_7O$—CO—, phosphono, O-alkyl-phosphono, O,O'-dialkylphosphono, tetrazol-5-yl or $R_8CO$—O—$CHR_9$—O—CO— group and (ix) the third of the groups $R_a$ to $R_d$ denotes a perfluoroalkyl or aryl group;

those wherein:

X denotes a carbimino group optionally substituted at the nitrogen atom by an alkyl or cyano group, or X denotes a carbonyl, thiocarbonyl, sulphonyl, 1-nitro-ethen-2,2-diyl or 1,1-dicyano-ethen-2,2-diyl group;

Y denotes a straight-chained $C_{2-4}$-alkylene group optionally substituted by $R_c$ or $R_d$ or by $R_c$ and $R_d$, and which may additionally be substituted by one or two alkyl groups, and wherein, additionally, one or two methylene groups may each be replaced by a carbonyl group, or Y denotes a straight-chained $C_{2-4}$-alkenylene group optionally substituted by $R_c$ or $R_d$ or by $R_c$ and $R_d$, wherein additionally any methylene group present may be replaced by a carbonyl group, or Y denotes a $C_{5-7}$-1,2-cycloalkylene group optionally substituted by $R_c$ or $R_d$ or by $R_c$ and $R_d$, or Y denotes a $C_{5-7}$-1,2-cycloalkenylene group optionally substituted by $R_c$ or $R_d$ or by $R_c$ and $R_d$, or Y denotes a 1,2-arylene group, a 1,2-phenylene group in which one or two methine groups are each replaced by a nitrogen atom or wherein one or two —CH=CH— groups are each replaced by a —CO—NH— group or wherein a methine group is replaced by a nitrogen atom and a —CH=CH— group by a —CO—NH— group, whilst the above mentioned heterocyclic groups may additionally be substituted by one or two alkyl groups, or a —CO—NH—, —NH—CO—, —CH=N— or —N=CH— group optionally substituted by $R_c$ or $R_d$;

a first of the groups $R_a$ to $R_d$ denotes a group of the formula

A—B—C—

(wherein A denotes a $C_{1-5}$-aminoalkyl group, or an amino, amidino or guanidino group, in which, at one of the nitrogen atoms of the above mentioned groups one or two hydrogen atoms may each be replaced by an alkyl group or a hydrogen atom may be replaced by an alkoxycarbonyl group having a total of 2 to 5 carbon atoms, by a benzyloxycarbonyl group or by an $R_1$—CO—O—($R_2CR_3$)—O—CO— group, wherein $R_1$ denotes a $C_{1-8}$-alkyl group, a $C_{5-7}$-cycloalkyl group or a phenyl or phenylalkyl group, $R_2$ denotes a hydrogen atom, an alkyl group, a $C_{5-7}$-cycloalkyl group or a phenyl group, and $R_3$ denotes a hydrogen atom or an alkyl group, or A denotes a cyano or cyanoalkyl group or if A is bound to a nitrogen atom of the groups B or C which is not part of a lactam group, A may also represent a hydrogen atom, an alkyl group, a benzyl group in which the phenyl moiety may be substituted by 1 to 2 methoxy groups, a formyl, acetyl or trifluoroacetyl group, an alkoxycarbonyl group having a total of 2 to 5 carbon atoms, a benzyloxycarbonyl group or an $R_1$—CO—O—($R_2CR_3$)—O—CO— group, wherein $R_1$ to $R_3$ are as hereinbefore defined;

B denotes a bond, a $C_{1-6}$-alkylene group, an arylene group, a pyridinylene, pyrimidinylene, pyrazinylene or pyridazinylene group in which one or two —CH=N— groups may each be replaced by a —CO—NH— group and one of the nitrogen atoms, instead of being bound to a hydrogen atom, may also be bound to the group C, provided that the latter does not have a heteroatom or carbonyl group adjoining the group B, and wherein the above mentioned heterocyclic groups may additionally be substituted by one or two alkyl groups, or B denotes a $C_{3-7}$-cycloalkylene group optionally substituted by one or two alkyl groups, a $C_{4-5}$-cycloalkylene group optionally substituted by a group $R_c$ and which may additionally be substituted by 1 to 4 alkyl groups and wherein, in the cycloalkylene moiety, a >CH unit is replaced by a nitrogen atom which is linked to the group A, wherein, with the proviso that a heteroatom of the group $R_c$ is separated from the cyclic nitrogen atom of the cyclic imino group by at least two carbon atoms, $R_c$ represents an alkyl, hydroxy, alkoxy, phenylalkoxy, alkylsulphenyl, alkylsulphinyl, alkylsulphonyl, cyano, carboxy, alkoxycarbonyl, phenylalkoxycarbonyl, alkylcarbonyl, aminocarbonyl, alkylaminocarbonyl, dialkylaminocarbonyl, amino, alkylamino, dialkylamino or phenyl group, or B denotes a $C_{6-8}$-cycloalkylene group which is optionally substituted by a group $R_c$ and which may additionally be substituted by 1 to 4 alkyl groups and wherein, in the cycloalkylene moiety, a >CH unit is replaced by a nitrogen atom which is linked to the group A and additionally another >CH unit in the 4-position may be replaced by a nitrogen atom, whilst, moreover, in the above mentioned 6–8-membered rings one or two methylene groups adjacent to a nitrogen atom may each be replaced by a carbonyl group, whilst $R_c$ is as hereinbefore defined, or B denotes a $C_{5-7}$-cycloalkenylene group optionally substituted by one or two alkyl groups and which may additionally be substituted by one or two methyl groups and wherein, in the cycloalkenylene moiety, a >CH unit is replaced by a nitrogen atom which is linked to the group A, the nitrogen atom being separated from the double bond by means of at least one optionally mono- or disubstituted methylene group, or B denotes a $C_{5-7}$cycloalkylene group wherein a >CH unit is replaced by a nitrogen atom linked to the group A and additionally two hydrogen atoms on the carbon skeleton are replaced by a straight-chained alkylene bridge, this bridge containing 2 to 6 carbon atoms if it replaces two hydrogen atoms on the same carbon atom, or containing 1 to 5 carbon atoms if it replaces two hydrogen atoms on adjacent carbon atoms, or containing 1 to 4 carbon atoms if it replaces two hydrogen atoms on carbon atoms which are separated by a further atom, or containing 1 to 3 carbon atoms if it replaces two hydrogen atoms on carbon atoms which are separated by two further atoms, in which the above groups may each be substituted by one or two alkyl groups, or B denotes a $C_{1-6}$-alkylene group linked to group C via a group W, wherein W denotes an oxygen or sulphur atom or a sulphinyl, sulphonyl, $NR_4$, $NR_5CO$ or $CONR_5$ group, wherein $R_4$ denotes a hydrogen atom or an alkyl, alkylcarbonyl, alkylsulphonyl, arylcarbonyl, heteroarylcarbonyl, arylsulphonyl or heteroarylsulphonyl group and $R_5$ denotes a hydrogen atom or an alkyl group, or B together with A denotes a pyridyl group optionally substituted by one or two alkyl groups or a piperidinyl group, in which the hydrogen atom in the 1-position together with a hydrogen atom in the 2-position is replaced by a straight-chained $C_{3-4}$-alkylene group, or B together with A denotes a piperidinyl group, in which the hydrogen atom in the 1-position together with a hydrogen atom in the 3-position is replace d by a straight-chained $C_{2-4}$-alkylene group, or B together with A denotes a piperidinyl group in which the hydrogen atom in the 1-position together with a hydrogen atom in the 4-position is replaced by a straight-chained $C_{1-3}$-alkylene group, wherein the methylene group of an ethylene chain bound to the 4-position may be replaced by a hydroxymethylene or carbonyl group and additionally the nitrogen atom of these above mentioned bicyclic groups, which may be substituted by one or two alkyl groups in the carbon skeleton, may be complexed by borane or quaternised by a benzyl group which is optionally substituted by 1 to 2 methoxy groups in the phenyl nucleus; and C denotes a $C_{1-6}$-alkylene group wherein a methylene group may be replaced by an oxygen or sulphur atom or by a sulphinyl, sulphonyl or $NR_4$ group, or wherein an ethylene group may be replaced by a $CONR_5$ or $NR_5CO$ group, wherein $R_4$ and $R_5$ are as hereinbefore defined, or C denotes a $C_{2-6}$-alkenylene group, an alkylene carbonyl group, having a total of 2 to 7 carbon atoms, which is linked to the group B via the carbonyl group, an arylene group, a pyridinylene, pyrimidinylene, pyrazinylene or pyridazinylene group, wherein one or two —CH=N— groups may each be replaced by a —CO—NH— group and one of the nitrogen atoms, instead of being bound to a hydrogen atom, may also be bound to the group B, provided that B does not denote a bond and does not adjoin the group C with a heteroatom or a carbonyl group, wherein the above mentioned heterocyclic groups may additionally be substituted by one or two alkyl groups, or C denotes a 3–7-membered cycloalkylene group optionally substituted by one or two alkyl groups or a cyclohexylene group in which two carbon atoms separated by three bonds are linked by a straight-chained $C_{1-3}$-alkylene group, whilst these bicyclic groups may additionally be substituted by one or two alkyl groups; or C together with A and B denotes a pyridyl or 1-(4-pyridyl)-piperidinyl group optionally substituted by one or two alkyl groups, or a piperidinyl group, in which the hydrogen atom in the 1-position together with a hydrogen atom in the 2-position is replaced by a straight chained $C_{3-4}$-alkylene group, or C together with A and B denotes a piperidinyl group in which the hydrogen atom in the 1-position together with a hydrogen atom in the 3-position is replaced by-a straight-chained $C_{2-4}$-alkylene group, or C together with A and B denotes a piperidinyl group in which the hydrogen atom in the 1-position together with a hydrogen atom in the 4-position is replaced by a straight-chained $C_{1-3}$-alkylene group, whilst the 4-position bound methylene-group of an ethylene chain may be replaced by a hydroxymethylene or carbonyl group and additionally the nitrogen atom of these above mentioned bicyclic groups which. may be substituted by one or two alkyl groups in the carbon skeleton may be complexed by borane or quaternised by a benzyl group which is optionally substituted by 1 to 2 methoxy groups in the phenyl nucleus; or if B denotes a bond, C may also represent (a) an indanylene, naphthylene, 1,2,3,4-tetrahydronaphthylene or benzosuberanylene group, in which one of the rings is bound to the group A and the other ring is bound to the cyclic group of general formula I, whilst the saturated rings may each be substituted by one or two alkyl groups and the aromatic rings may each be substituted by a fluorine, chlorine, bromine or iodine atom or by an alkyl, trifluoromethyl, hydroxy, alkoxy, aklylsulphenyl, alkylsulphinyl, alkylsulphonyl or cyano group and wherein, additionally, one or two methine groups may each be replaced by a nitrogen atom, (b) a $C_{4-5}$-cycloalkylene group optionally substituted by the group Rt and which may additionally be substituted by 1 to 4 alkyl groups and wherein, in the cycloalkylene moiety, a >CH unit is replaced by a nitrogen atom linked to the group A, wherein $R_c$ is as hereinbefore defined, (c) a $C_{6-8}$-cycloalkylene group optionally substituted by the group $R_c$ and which may additionally be substituted by 1 to 4 alkyl groups and wherein, in the cycloalkylene moiety, a >CH unit is replaced by a nitrogen atom linked to the group A and additionally another >CH-unit in the 4-position may be replaced by a nitrogen atom, whilst furthermore, in the above mentioned 6–8-membered rings, one or two methylene groups adjacent to a nitrogen atom may each be replaced by a carbonyl group, whilst $R_c$ is as hereinbefore defined, (d) a $C_{5-7}$-cycloalkenylene group optionally substituted by one or two alkyl groups and which may additionally be substituted by one or two methyl groups and wherein, in the cycloalkenylene moiety, a >CH unit is replaced by a nitrogen atom linked to the group A, whilst the nitrogen atom is separated from the double bond by at least one optionally mono- or di-substituted methylene group, or (e) a $C_{5-7}$-cycloalkylene group wherein a >CH unit is replaced by a nitrogen atom linked to the group A and additionally two hydrogen atoms on the carbon skeleton are replaced by a straight-chained alkylene bridge, this bridge containing 2 to 6 carbon atoms if it replaces two hydrogen atoms on the same carbon atom, or containing 1 to 5 carbon atoms if it replaces two hydrogen atoms on adjacent carbon atoms, or containing 1 to 4 carbon atoms if it replaces two hydrogen atoms on carbon atoms separated by a further atom, or containing 1 to 3 carbon atoms if it replaces two hydrogen atoms on carbon atoms separated by two further atoms in which the above groups may each be substituted by one or two alkyl groups);

a second of groups $R_a$ to $R_d$ denotes a group of the formula

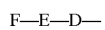

F—E—D—

(wherein D denotes a $C_{1-6}$-alkylene group in which a methylene group may be replaced by an oxygen or sulphur atom or by a sulphinyl, sulphonyl or $NR_4$ group, or wherein an ethylene group may be replaced by a CO—$NR_5$ or $NR_5$—CO group wherein $R_4$ and $R_5$ are as hereinbefore defined, a $C_{2-6}$-alkenylene group, an arylene group, a pyridinylene, pyrimidinylene, pyrazinylene or pyridazinylene group in which one or two —CH=N— groups may each be replaced by a —CO—NH— group and one of the nitrogen atoms, instead of being bound to a hydrogen atom, may also be bound to the group E provided that E does not represent a bond or does not adjoin the group D with a heteroatom or a carbonyl group, whilst the above mentioned heterocyclic groups may additionally be substituted by one or two alkyl groups, or D denotes an indanylene, naphthylene, 1,2,3,4-tetrahydronaphthylene or benzosuberanylene group, in which one of the rings is bound to the group E and the other ring is bound to the cyclic group of general formula I, whilst the saturated rings may each be substituted by one or two alkyl groups and the aromatic rings may each be substituted by a fluorine, chlorine, bromine or iodine atom or by an alkyl, trifluoromethyl, hydroxy, alkoxy, alkylsulphenyl, alkylsulphinyl, alkylsulphonyl or cyano group and wherein additionally one or two methine groups may each be replaced by a nitrogen atom, or D denotes a $C_{3-7}$-cycloalkylene group optionally substituted by one or two alkyl groups, a $C_{4-7}$-cycloalkylene group optionally substituted by one or two alkyl groups, wherein a >CH unit is replaced by a nitrogen atom, and furthermore in the above mentioned 4–7-membered rings one, or for a ring size of at least 5 one or two, methylene groups adjacent to a nitrogen atom may each be replaced by a carbonyl group, a $C_{1-7}$-cycloalkylene group optionally substituted by one or two alkyl groups, wherein two >CH units located in the 1,4-position relative to each other are each replaced by a nitrogen atom, whilst moreover in the above mentioned 6- or 7-membered rings one or two methylene groups adjacent to a nitrogen atom may each be replaced by a carbonyl group, a cyclohexylene group in which two carbon atoms separated by three bonds are linked by a straight-chained $C_{1-3}$-alkylene groups, whilst these bicyclic groups may also be substituted by 1 to 2 alkyl groups, or, if E is a cyclic imino group, D may also represent an alkylenecarbonyl group having a total of 2 to 6 carbon atoms, wherein the carbonyl group in each case is bound to the nitrogen atom of the cyclic imino group of the group E, or, if E does not represent a bond, D may represent a bond;

E denotes a bond, a $C_{1-6}$-alkylene group or a $C_{2-6}$-alkenylene group each of which may be substituted by one or two $C_{1-8}$-alkyl groups, by a hydroxy, amino, aryl or heteroaryl group, by a $C_{1-8}$-alkoxy or $C_{1-8}$-alkylamino group, by a dialkylamino group having a total of 2 to 10 carbon atoms, by an $HNR_6$ or N-phenylalkyl-$NR_6$ group or by an N-alkyl-$NR_6$ group having 1 to 8 carbon atoms in the alkyl moiety, wherein $R_c$ denotes an alkylcarbonyl or alkylsulphonyl group each having 1 to 8 carbon atoms in the alkyl moiety, an alkyloxycarbonyl group having a total of 2 to 5 carbon atoms, a cycloalkylcarbonyl or cycloalkylsulphonyl group each having 5 to 7 carbon atoms in the cycloalkyl moiety, an arylalkylcarbonyl, arylalkylsulphonyl, arylalkoxycarbonyl, arylcarbonyl, arylsulphonyl, heteroarylalkylcarbonyl, heteroarylalkylsulphonyl, heteroarylalkoxycarbonyl, heteroarylcarbonyl or heteroarylsulphonyl group, an arylene group, a pyridinylene, pyrimidinylene, pyrazinylene or pyridazinylene group, wherein one or two CH=N groups may each be replaced by a CO—NH group and one of the nitrogen atoms, instead of being bound to a hydrogen atom, may also be bound to the group Do provided that D does not denote a bond and D does not adjoin the group E with a heteroatom or a carbonyl group, whilst the above mentioned heterocyclic groups may additionally be substituted by one or two alkyl groups, a $C_{5-7}$-cycloalkylene group optionally substituted by one or two alkyl groups, wherein a >CH unit is replaced by a nitrogen atom which is linked to a carbon atom of the group D, a cycloalkylene group having 4 to 7 carbon atoms in the cycloalkylene moiety, optionally substituted by one or two $C_{1-8}$-alkyl groups or by a hydroxy, amino, aryl or heteroaryl group, by an alkoxy or alkylamino group having 1 to 8 carbon atoms, by a dialkylamino group having a total of 2 to 10 carbon atoms, by a n $HNR_6$ or N-phenylalkyl-$NR_6$ group or by an N-alkyl-$NR_6$ group having 1 to 8 carbon atoms in the alkyl moiety, whilst $R_6$ is as hereinbefore defined, or, if D does not denote a bond, E may denote an alkylene group linked to the group D via a group W, wherein W is as hereinbefore defined and the alkylene group may additionally be substituted by one or two $C_{1-8}$-alkyl groups, by a hydroxy, amino, aryl or heteroaryl group, by an alkoxy or alkylamino group each having 1 to 8 carbon atoms, by a dialkylamino group having a total of 2 to 10 carbon atoms, by an $HNR_6$ or N-phenylalkyl-$NR_6$ group or by an N-alkyl-$NR_6$ group having 1 to 8 carbon atoms in the alkyl moiety, whilst the heteroatom of the additional substituent is separated by at least two carbon atoms from a heteroatom of group W and $R_6$ is as hereinbefore defined, and with the proviso that D together with E does not represent a $(CH_2)_n$—CONH—$CH_2CH_2$ group, wherein n denotes the number 1, 2, 3 or 4 and the ethylene moiety attached to the nitrogen atom may optionally be substituted as mentioned hereinbefore; and F denotes a carbonyl group which is substituted by a hydroxy group, by a $C_{1-8}$-alkoxy group, by an arylalkoxy group or by an $R_7O$— group, wherein $R_7$ denotes a $C_{4-8}$-cycloalkyl group or a cycloalkylalkyl group having 3 to 8 carbon atoms in the cycloalkyl moiety, wherein the cycloalkyl group may be substituted by an alkyl group, by an alkyl group and by 1 to 3 methyl groups, or by an alkoxy or dialkylamino group and additionally a methylene group in a 4–8-membered cycloalkyl moiety may be replaced by an oxygen or sulphur atom or by a sulphinyl, sulphonyl or alkylamino group, or $R_7$ may denote a bicycloalkyl or bicycloalkylalkyl group wherein the bicycloalkyl moiety contains 6 to 10 carbon atoms and may additionally be substituted by 1 to 3 methyl groups, or $R_7$ may denote a $C_{9-12}$-benzocycloalkyl group or an aryl group, or F denotes a phosphono, O-alkyl-phosphono, O,O'-dialkylphosphono, tetrazol-5-yl or $R_8CO—O—CHR_9—O—CO—$ group, wherein $R_8$ denotes a $C_{1-8}$-alkyl or $C_{1-8}$-alkoxy group, a cycloalkyl or cycloalkoxy group each having 5 to 7 carbon atoms in the cycloalkyl moiety or an aryl, aryloxy, arylalkyl or arylalkoxy group and $R_9$ denotes a hydrogen atom, a $C_{5-7}$-cycloalkyl group or an alkyl or aryl group, and the shortest distance between the group F and the furthest removed nitrogen atom of the groups A—B—C amounts to at least 11 bonds);

the third of the groups $R_a$ to $R_d$ denotes a hydrogen atom, an alkyl, perfluoroalkyl, alkoxy, alkylsulphenyl, alkylsulphinyl, alkylsulphonyl, amino, alkylamino, dialkylamino, aryl, arylalkyl, heteroaryl or heteroarylalkyl group; and the fourth of the groups $R_a$ to $R_d$ denotes a hydrogen atom or an alkyl, aryl or arylalkyl group;

wherein, unless otherwise specified the aryl moieties mentioned in the definition of the above groups may be taken to mean a phenyl group which is monosubstituted by $R_{10}$, mono-, di- or tri-substituted by $R_{11}$, or monosubstituted by $R_{10}$ and additionally mono- or di-substituted by $R_{11}$, wherein the substituents may be identical or different and $R_{10}$ denotes a cyano, carboxy, aminocarbonyl, alkylaminocarbonyl, dialkylaminocarbonyl, alkoxycarbonyl, alkylcarbonyl, alkylsulphenyl, alkylsulphinyl, alkylsulphonyl, alkylsulphonyloxy, perfluoroalkyl, trifluoromethoxy, nitro, amino, alkylamino, dialkylamino, alkylcarbonylamino, phenylalkylcarbonylamino, phenylcarbonylamino, alkylsulphonylamino, phenylalkylsulphonylamino, phenylsulphonylamino, N-alkyl-alkylcarbonylamino, N-alkyl-phenylalkylcarbonylamino, N-Alkyl-phenylcarbonylamino, N-Alkyl-alkylsulfonylamino, N-alkyl-phenylalkylsulphonylamino, N-alkyl-phenylsulphonylamino, aminosulphonyl, alkylamino-sulphonyl or dialkylaminosulphonyl group and $R_{11}$ denotes an alkyl, hydroxy or alkoxy group or a fluorine, chlorine, bromine or iodine atom, whilst two groups $R_{11}$, if they are bound to adjacent carbon atoms, may also represent a $C_{3-6}$-alkylene group, a 1,3-butadiene-1,4-diylene group or a methylene-dioxy group, the arylene moieties mentioned in the definition of the above groups may be taken to mean a phenylene group which may be monosubtituted by $R_{10}$, mono- or di-substituted by $R_{11}$, or monosubstituted by $R_{10}$ and additionally monosubstituted by $R_{11}$, whilst the substituents may be identical or different and are defined as hereinbefore, the heteroaryl moieties mentioned in the definition of the above groups may be taken to mean a 5-membered heteroaromatic ring which contains an oxygen, sulphur or nitrogen atom, a nitrogen atom and an oxygen, sulphur or nitrogen atom, or two nitrogen atoms and an oxygen, sulphur or nitrogen atom, or a 6-membered heteroaromatic ring which contains 1, 2 or 3 nitrogen atoms and wherein, additionally, one or two CH=N groups may each be replaced by a CO—$NR_5$ group, wherein $R_5$ is as hereinbefore defined, and additionally the above mentioned heteroaromatic rings may be substituted by one or two alkyl groups or, on the carbon skeleton, by a fluorine, chlorine, bromine or iodine atom or by a hydroxy or alkoxy group, and unless otherwise specified the above mentioned alkyl, alkylene or alkoxy moieties may each contain 1 to 4 carbon atoms and each carbon atom in the above mentioned alkylene and cycloalkylene moieties may be linked to not more than one heteroatom.

Preferred compounds of general formula I above are, with the exception of

1-[4-(4-amidino-phenyl)-cyclohexyl]-3-(2-carboxy-ethyl)-imidazolidin-2-one,

1-[4-(4-amidino-phenyl)-cyclohexyl]-3-(2-methoxycarbonyl-ethyl)-imidazolidin-2-one, 1-[4-(4-amidino-phenyl)-cyclohexyl]-3-(2-methoxycarbonyl-ethyl)-3H-imidazol-2-one, 1-[4-(4-amidino-phenyl)-cyclohexyl]-3-(2-carboxy-ethyl)-3H-imidazol-2-one, 1-[4-(4-cyano-phenyl)-cyclohexyl]-3-(2-ethoxycarbonyl-ethyl)-3H-imidazol-2-one, 1-(4-amidino-phenyl)-3-[4-(2-carboxy-ethyl)-cyclohexyl]-imidazolidin-2-one, 1-(4-amidino-phenyl)-3-[4-(2-methoxycarbonyl-ethyl)-cyclohexyl]-imidazblidin-2-one, 1-(4-cyano-phenyl)-3-[4-(2-methoxycarbonyl-ethyl)-cyclohexyl]-3H-idazolidin-2-one, 1-(4-amidino-phenyl)-3-[4-(2-phosphono-ethyl)-phenyl]-imidazolidin-2-one, 1-(4-amidino-phenyl)-3-[4-[2-(O-methyl-phosphono)-ethyl]-phenyl]-imidazolidin-2-one, 1-(4-cyano-phenyl)-3-[4-(2-phosphono-ethyl)-phenyl]-imidazolidin-2-one, 1-(4-cyano-phenyl)-3-[4-[2-(O-methyl-phosphono)-ethyl]-phenyl]-imidazolidin-2-one, 1-(1-amidino-4-piperidinyl)-3-[4-(2-carboxy-ethyl)-phenyl)-imidazolidin-2-one, 1-(1-amidino-4-piperidinyl)-3-[4-(2-methoxycarbonyl-ethyl)-phenyl]-imidazolidin-2-one, 1-(4-aminomethyl-cyclohexyl)-3-[4-(2-carboxy-ethyl)-phenyl]-imidazolidin-2-one, 1-(4-aminomethyl-cyclohexyl)-3-[4-(2-methoxycarbonyl-ethyl)-phenyl]-imidazolidin-2-one, 1-(4-amidino-phenyl)-3-[4-(2-carboxy-ethyl)-phenyl]-4-phenyl-3H-imidazol-2-one, 1-(4-amidino-phenyl)-3-[4-(2-methoxycarbonyl-ethyl)-phenyl]-4-phenyl-3H-imidazol-2-one, 1-(4-amidino-phenyl)-3-[4-(2-carboxy-ethyl)-phenyl]-4-phenyl-imidazolidin-2-one, 1-(4-amidino-phenyl)-3-[4-(2-methoxycarbonyl-ethyl)-phenyl]-4-phenyl-imidazolidin-2-one, 4-(4-amidino-phenyl)-1-[4-(2-carboxy-ethyl)-phenyl]-3-phenyl-3H-imidazol-2-one, 4-(4-amidino-phenyl)-1-[4-(2-methoxycarbonyl-ethyl)-phenyl]-3-phenyl-3H-imidazol-2-one, 4-(4-cyano-phenyl)-1-[4-(2-methoxycarbonyl-ethyl)-phenyl]-3-phenyl-3H-imidazol-2-one, 4-(4-amidino-phenyl)-1-[4-(2-carboxy-ethyl)-phenyl]-3-phenyl-3H-imidazol-2-thione,
4-(4-amidino-phenyl)-1-[4-(2-methoxycarbonyl-ethyl)-phenyl]-3-phenyl-3H-imidazol-2-thione,
4-(4-cyano-phenyl)-1-[4-(2-methoxycarbonyl-ethyl)-phenyl]-3-phenyl-3H-imidazol-2-thione,
4-(4-amidino-phenyl)-1-[4-(2-carboxy-ethyl)-phenyl]-5-methyl-3-phenyl-3H-imidazol-2-one,
4-(4-amidino-phenyl)-1-[4-(2-methoxycarbonyl-ethyl)-phenyl]-5-methyl-3-phenyl-3H-imidazol-2-one,
4-(4-cyano-phenyl)-1-[4-(2-methoxycarbonyl-ethyl)-phenyl]-5-methyl-3-phenyl-3H-imidazol-2-one,
4-(4-amidino-phenyl)-1-[4-(2-carboxy-ethyl)-phenyl]-3-phenyl-imidazolidin-2-one,
4-(4-amidino-phenyl)-1-[4-(2-methoxycarbonyl-ethyl)-phenyl]-3-phenyl-imidazolidin-2-one,
1-(4-amidino-phenyl)-4-[4-(2-carboxy-ethyl)-phenyl]-3-phenyl-3H-imidazol-2-one,
1-(4-amidino-phenyl)-4-[4-(2-methoxycarbonyl-ethyl)-phenyl]-3-phenyl-3H-imidazol-2-one,
1-(4-cyano-phenyl)-4-[4-(2-methoxycarbonyl-ethyl)-phenyl]-3-phenyl-3H-imidazol-2-one,
1-(4-amidino-phenyl)-4-[4-(2-carboxy-ethyl)-phenyl]-3-phenyl-imidazolidin-2-one,
1-(4-amidino-phenyl)-4-[4-(2-methoxycarbonyl-ethyl)-phenyl]-3-phenyl-imidazolidin-2-one,
1-(4-amidino-phenyl)-4-[4-(2-carboxy-ethyl)-phenyl]-3-phenyl-3H-imidazol-2-thione,
1-(4-amidino-phenyl)-4-[4-(2-methoxycarbonyl-ethyl)-phenyl]-3-phenyl-3H-imidazol-2-thione,
1-(4-cyano-phenyl)-4-(4-(2-methoxycarbonyl-ethyl)-phenyl]-3-phenyl-3H-imidazol-2-thione,
1-(4-amidino-phenyl)-4-[4-(2-carboxy-ethyl)-phenyl]-5-methyl-3-phenyl-3H-imidazol-2-one,
1-(4-amidino-phenyl)-4-(4-(2-methoxycarbonyl-ethyl)-phenyl]-5-methyl-3-phenyl-3H-imidazol-2-one,
1-(4-cyano-phenyl)-4-[4-(2-methoxycarbonyl-ethyl)-phenyl]-5-methyl-3-phenyl-3H-imidazol-2-one,
4-(4'-amidino-4-biphenylyl)-1-(2-carboxy-ethyl)-3-phenyl-3H-imidazol-2-one,
4-(4'-amidino-4-biphenylyl)-1-(2-methoxycarbonyl-ethyl)-3-phenyl-3H-imidazol-2-one,
4-(4'-cyano-4-biphenylyl)-1-(2-methoxycarbonyl-ethyl)-3-phenyl-3H-imidazol-2-one,
4-[4'-amidino-4-biphenylyl)-1-(2-carboxy-ethyl)-3-phenyl-imidazolidin-2-one,
4-(4'-amidino-4-biphenylyl)-1-(2-methoxycarbonyl-ethyl)-3-phenyl-imidazolidin-2-one,
4-(4'-amidino-4-biphenylyl)-1-(2-carboxy-ethyl)-3-phenyl-3H-imidazol-2-thione,
4-(4'-amidino-4-biphenylyl)-1-(2-methoxycarbonylethyl)-3-phenyl-3H-imidazol-2-thione,
4-(4'-cyano-4-biphenylyl)-1-(2-methoxycarbonyl-ethyl)-3-phenyl-3H-imidazol-2-thione,
4-(4'-amidino-4-biphenylyl)-1-(2-carboxy-ethyl)-5-methyl-3-phenyl-3H-imidazol-2-one,
4-(4'-amidino-4-biphenylyl)-1-(2-methoxycarbonyl-ethyl)-5-methyl-3-phenyl-3H-imidazol-2-one,
4-(4'-cyano-4-biphenylyl)-1-(2-methoxycarbonyl-ethyl)-5-methyl-3-phenyl-3H-imidazol-2-one,
1-(4-amidino-phenyl)-3-[4-(2-butyloxycarbonyl-ethyl)-phenyl]-imidazolidin-2-one,
1-(4'-amidino-4-biphenylyl)-3-(2-ethoxycarbonyl-ethyl)-3H-imidazol-2-one,
1-(4'-cyano-4-biphenylyl)-3-(2-ethoxycarbonyl-ethyl)-3H-imidazol-2-one,
1-(4'-amidino-4-biphenylyl)-3-(2-ethoxycarbonyl-ethyl)-imidazolidin-2,4-dione,
1-(4'-cyano-4-biphenylyl)-3-(2-ethoxycarbonyl-ethyl)-imidazolidin-2,4-dione,
1-(4'-amidino-4-biphenylyl)-3-(2-ethoxycarbonyl-ethyl)-3,4,5,6-tetrahydro-1H-pyrimidin-2-one,
1-(4'-cyano-4-biphenylyl)-3-(2-ethoxycarbonyl-ethyl)-3,4,5,6-tetrahydro-1H-pyrimidin-2-one,
2-(4-amidino-phenyl)-4-[4-(2-isopropyloxycarbonyl-ethyl)-phenyl]-5-methyl-4H-1,2,4-triazol-3-one,
4-[4-(2-isopropyloxycarbonyl-ethyl)-phenyl]-2-(4-methoxy-carbonylamidino-phenyl)-5-methyl-4H-1,2,4-triazol-3-one,
1-(4-amidino-phenyl)-3-[4-(2-ethoxycarbonyl-ethyl)-phenyl]-3H-imidazol-2-one,
1-(4-ethoxycarbonylamidino-phenyl)-3-[4-(2-ethoxycarbonyl-ethyl)-phenyl]-3H-imidazol-2-one,
1-(4-ethoxycarbonylamidino-phenyl)-3-[4-(2-ethoxycarbonyl-ethyl)-phenyl]-imidazolidin-2-one,
1-(4-methoxycarbonylamidino-phenyl)-3-[4-(2-methoxycarbonyl-ethyl)-cyclohexyl]-imidazolidin-2-one,
4-[4-(2-isobutyloxycarbonyl-ethyl)-phenyl]-2-(4-methoxy-carbonylamidino-phenyl)-5-methyl-4H-1,2,4-triazol-3-one,
2-(4-amidino-phenyl)-4-[4-(2-isobutyloxycarbonyl-ethyl)-phenyl]-5-methyl-4H-1,2,4-triazol-3-one,
1-(1-amino-5-indanyl)-3-[4-(2-carboxy-ethyl)-phenyl]-imidazolidin-2-one,
1-(1-amino-5-indanyl)-3-[4-(2-methoxycarbonyl-ethyl)-phenyl]-imidazolidin-2-one,
1-(1-amino-1,2,3,4-tetrahydro-6-naphthyl)-3-[4-(2-carboxy-ethyl)-phenyl]-imidazolidin-2-one,
1-(1-amino-1,2,3,4-tetrahydro-6-naphthyl)-3-[4-(2-methoxy-carbonyl-ethyl)-phenyl]-imidazolidin-2-one,
1-(4-amino-cyclohexyl)-3-[4-(3-carboxy-propyl)-phenyl]-imidazolidin-2-one,
1-(4-amino-cyclohexyl)-3-[4-(3-methoxycarbonyl-propyl)-phenyl]-imidazolidin-2-one,
1-(4-amino-cyclohexyl)-3-[4-(2-carboxy-ethyl)-phenyl]-imidazolidin-2-one,
1-(4-amino-cyclohexyl)-3-[4-(2-methoxycarbonyl-ethyl)-phenyl]-imidazolidin-2-one,
1-(4-aminomethyl-phenyl)-3-[3-(2-carboxy-ethyl)-phenyl]-imidazolidin-2-one,
1-(4-aminomethyl-phenyl)-3-[3-(2-methoxycarbonyl-ethyl)-phenyl]-imidazolidin-2-one,
1-(4-amino-cyclohexyl)-3-[4-[(2-carboxy-ethyl)-aminocarbonyl]-phenyl]-imidazolidin-2-one,
1-(4-amino-cyclohexyl)-3-[4-[(2-methoxycarbonyl-ethyl)-aminocarbonyl]-phenyl]-imidazolidin-2-one,
1-[4-[(2-carboxy-ethyl)-aminocarbonyl]-phenyl]-3-(4-piperidinyl)-imidazolidin-2-one,
1-[4-[(2-methoxycarbonyl-ethyl)-aminocarbonyl]-phenyl]-3-(4-piperidinyl)-imidazolidin-2-one,
1-[4-(1-amino-cyclopropyl)-phenyl]-3-[4-(2-carboxyethyl)-phenyl]-imidazolidin-2-one,
1-[4-(1-amino-cyclopropyl)-phenyl]-3-[4-(2-methoxycarbonyl-ethyl)-phenyl]-imidazolidin-2-one,
1-[4-(1-amino-cyclopentyl)-phenyl]-3-[4-(2-carboxyethyl)-phenyl]-imidazolidin-2-one,
1-[4-(1-amino-cyclopentyl)-phenyl]-3-[4-(2-methoxycarbonyl-ethyl)-phenyl]-imidazolidin-2-one,
2-(4-amidino-phenyl)-5-ethyl-4-[4-(2-isopropyloxycarbonyl-ethyl)-phenyl]-4H-1,2,4-triazol-3-one,
1-(4-amidino-phenyl)-3-[4-(2-isopropyloxycarbonylethyl)-phenyl]-4-methyl-3H-imidazol-2-one,
4-(4-amidino-phenyl)-2-[4-(2-isopropyloxycarbonylethyl)-phenyl]-4H-1,2,4-triazol-3-one, 1-(4-amidino-phenyl)-3-[4-(2-isopropyloxycarbonylethyl)-phenyl]-imidazolidin-2-one,
1-(4-amidino-phenyl)-3-[4-(2-isopropyloxycarbonylethyl)-phenyl]-3H-imidazol-2-one,
1-(4-amidino-phenyl)-3-[4-(2-isopropyloxycarbonylethyl)-phenyl]-imidazolidin-2,4-dione,
1-[4-[(2-carboxy-ethyl)-aminocarbonyl]-phenyl]-3-(1-methyl-4-piperidinyl)-imidazolidin-2-one,
2-(4-amidino-phenyl)-4-[4-(2-phosphono-ethyl)-phenyl]-5-methyl-4H-1,2,4-triazol-3-one,
2-(4-amidino-phenyl)-4-[4-[2-(O-methyl-phosphono)-ethyl]-phenyl]-5-methyl-4H-1,2,4-triazol-3-one,
2-(4-amidino-phenyl)-4-[4-(2-carboxy-ethyl)-phenyl]-5-phenyl-4H-1,2,4-triazol-3-one,
2-(4-amidino-phenyl)-4-[4-(2-methoxycarbonyl-ethyl)-phenyl]-5-phenyl-4H-1,2,4-triazol-3-one,
3-(4-amidino-phenyl)-1-[4-(2-carboxy-ethyl)-phenyl]-4-trifluoromethyl-3H-imidazol-2-one,
3-(4-amidino-phenyl)-1-[4-(2-methoxycarbonyl-ethyl)-phenyl]-4-trifluoromethyl-3H-imidazol-2-one,
2-(4-amidino-phenyl)-4-[4-(2-carboxy-ethyl)-phenyl]-5-trifluoromethyl-4H-1,2,4-triazol-3-one,
2-(4-amidino-phenyl)-4-[4-(2-methoxycarbonyl-ethyl)-phenyl]-5-trifluoromethyl-4H-1,2,4-triazol-3-one and
3-(4-cyano-phenyl)-1-(4-ethoxycarbonyl-butyl)-3H-imidazo-[4,5-b]pyridin-2-one,
and with the proviso that at least one of conditions (i) to (ix) below is satisfied (i) X denotes a carbimino group substituted at the nitrogen atom by a cyano group, (ii) Y denotes a $C_{5-7}$-1,2-cycloalkylene group optionally substituted by $R_c$ or $R_d$ or by $R_c$ and $R_d$.

(iii) A denotes a $C_{1-5}$-aminoalkyl group or an amino, amidino or guanidino group, wherein at one of the nitrogen atoms in each of the above mentioned groups a hydrogen atom is replaced by an $R_1$—CO—O—($R_2CR_3$)—O—CO— group, (iv) B denotes a $C_{3-7}$-cycloalkylene group optionally substituted by one or two alkyl groups,
a $C_{4-5}$-cycloalkylene group optionally substituted by a group $R_c$ and which may additionally be substituted by 1 to 4 alkyl groups and in which, in the cycloalkylene moiety, a >CH unit is replaced by a nitrogen atom,
a $C_{6-8}$-cycloalkylene group optionally substituted by a group $R_c$ and which may additionally be substituted by 1 to 4 alkyl groups and in which, in the cycloalkylene moiety, a >CH unit is replaced by a nitrogen atom and additionally another >CH unit in the 4-position may be replaced by a nitrogen atom, whilst, moreover, in the above mentioned 6- to 8-membered rings one or two methylene groups adjacent to a nitrogen atom may each be replaced by a carbonyl group,
a $C_{5-7}$-cycloalkenylene group optionally substituted by 1 or 2 alkyl groups and which may additionally be substituted by 1 or 2 methyl groups and wherein, in the cycloalkenylene moiety, a >CH unit is replaced by a nitrogen atom,
a piperidinylene group in which two hydrogen atoms on the carbon skeleton are replaced by a straight-chained alkylene bridge, this bridge containing 2 to 6 carbon atoms if it replaces two hydrogen atoms on the same carbon atom, or containing 1 to 5 carbon atoms if it replaces two hydrogen atoms on adjacent carbon atoms, or containing 1 to 4 carbon atoms if it replaces two hydrogen atoms on carbon atoms separated by a further atom, or containing 1 to 3 carbon atoms if it replaces two hydrogen atoms on carbon atoms separated by 2 further atoms, in which the above groups may each be substituted by one or two alkyl groups,
an alkylene group linked to the group C via a group W,
or B together with A denotes a pyridyl group optionally substituted by one or two alkyl groups, or a piperidinyl group in which the hydrogen atom in the 1-position together with a hydrogen atom in the 2-position is replaced by a straight-chained $C_{3-4}$-alkylene group, or a piperidinyl group in which the hydrogen atoms in the 1-position together with a hydrogen atom in the 3-position is replaced by a straight-chained $C_{2-4}$-alkylene group, or a piperidinyl group in which the hydrogen atom in the 1-position together with a hydrogen atom in the 4-position is replaced by a straight-chained $C_{1-3}$-alkylene group, whilst a 4-position bound methylene group of an ethylene chain may be replaced by a hydroxymethylene or carbonyl group and additionally the nitrogen atom of these above mentioned bicyclic groups, which may be substituted in the carbon skeleton by 1 or 2 alkyl groups, may be completed by borane or quaternised by a benzyl group optionally substituted by one to two methoxy groups in the phenyl nucleus, (v) C denotes a $C_{1-6}$-alkylene group in which a methylene group is replaced by an oxygen or sulphur atom or by a sulphinyl, sulphonyl or $NR_4$ group or wherein an ethylene group is replaced by a $CONR_5$ or $NR_5CO$ group,
a 5–7-membered cycloalkylene group optionally substituted by one or two alkyl groups,
a cyclohexylene group in which two carbon atoms separated by three bonds are linked by a straight-chained $C_{1-3}$-alkylene group, whilst these bicyclic groups may also be substituted by one to two alkyl groups,
an indanylene, naphthylene, 1,2,3,4-tetrahydronaphthylene or benzosuberanylene group, wherein the saturated rings may each be substituted by one or two alkyl groups and the aromatic rings may each be substituted by a fluorine, chlorine, bromine or iodine atom, or by an alkyl, trifluoromethyl, hydroxy, alkoxy, alkylsulphenyl, alkylsulphinyl, alkysulphonyl or cyano group,
a $C_{5-7}$-cycloalkylene group optionally substituted by the group $R_c$ and which may additionally be substituted by 1 to 4 alkyl groups and wherein, in the cycloalkylene moiety, a >CH unit is replaced by a nitrogen atom,
a piperidinylene group in which two hydrogen atoms on the carbon skeleton are replaced by a straight-chained alkylene bridge, this bridge containing 2 to 6 carbon atoms if it replaces 2 hydrogen atoms on the same carbon atom, or containing 1 to 5 carbon atoms if it replaces two hydrogen atoms on adjacent carbon atoms, or containing 1 to 4 carbon atoms if it replaces two hydrogen atoms on carbon atoms separated by a further atom, or containing 1 to 3 carbon atoms if it replaces two hydrogen atoms on carbon atoms separated by two further atoms, in which the above groups may each be substituted by one or two alkyl groups,
or C together with A and B denotes a pyridyl or 1-(4-pyridyl)-piperidinyl group optionally substituted by one or two alkyl groups, or a piperidinyl group in which the hydrogen atom in the 1-position together with a hydrogen atom in the 4-position is replaced by a straight-chained $C_{1-3}$-alkylene group, whilst a 4-position bound methylene group of an ethylene chain may be replaced by a hydroxymethylene or carbonyl group and additionally the nitrogen atom of these above mentioned bicyclic groups, which may be substituted in the carbon skeleton by one or two alkyl groups, may be complexed by borane or quaternised by a benzyl group optionally substituted by 1 to 2 methoxy groups in the phenyl nucleus, or C denotes a $C_{1-6}$-alkylene group and B denotes a bond, (vi) D denotes a 1,3-arylene group, an indanylene, naphthylene, 1,2,3,4-tetrahydronaphthylene or benzosuberanylene group, wherein the saturated rings may each be substituted by one or two alkyl groups and the aromatic rings may each be substituted by a fluorine, chlorine, bromine or iodine atom or by an alkyl, trifluoromethyl, hydroxy, alkoxy, alkylsulphenyl, alkylsulphinyl, alkylsulphonyl or cyano group, a $C_{4-7}$-cycloalkylene group optionally substituted by one or two alkyl groups or a cyclohexylene group in which two carbon atoms separated by three bonds are linked by a straight-chained $C_{1-3}$-alkylene group, whilst these bicyclic groups may each also be substituted by one to two alkyl groups, (vii) E denotes a straight-chained $C_{1-3}$-alkylene group substituted by a $C_{1-6}$-alkyl group, by an aryl group or by an $HNR_6$- or $N$-alkyl-$NR_6$- group, a $C_{5-7}$-cycloalkylene group optionally substituted by one or two alkyl groups and wherein a >CH unit is replaced by a nitrogen atom, a cycloalkylene group having 4 to 7 carbon atoms in the cycloalkylene moiety substituted by a hydroxy or amino group, by a $C_{1-6}$-alkoxy group or by an $HNR_6$- or $N$-alkyl-$NR_6$- group, or E denotes an alkylene group linked to group D via a group W, wherein the alkylene group may additionally be substituted by one or two $C_{1-6}$-alkyl groups, by a hydroxy, amino or aryl group, by a $C_{1-6}$-alkoxy group or by an $HNR_6$- or $N$-alkyl-$NR_6$- group, (viii) F denotes an alkoxycarbonyl group having a total of 3 to 9 carbon atoms, an $R_7O$—CO—, phosphono, O-alkyl-phosphono, O,O'-dialkyl-phosphono or $R_8CO$—O—$CHR_9$—O—CO— group and (ix) the third of the groups $R_a$ to $R_d$ denotes a trifluoromethyl or aryl group;

those wherein:

X denotes a carbimino group optionally substituted at the nitrogen atom by an alkyl or cyano group, or X denotes a carbonyl, thiocarbonyl or sulphonyl group;

Y denotes a straight-chained $C_{2-3}$-alkylene group optionally substituted by $R_c$ or $R_d$ or by $R_c$ and $R_d$ and which may additionally be substituted by one or two alkyl groups, and wherein, additionally, a methylene group may be replaced by a carbonyl group, a straight-chained $C_{2-3}$-alkenylene group optionally substituted by $R_c$ or $R_d$ or by $R_c$ and $R_d$, wherein additionally any methylene group present may be replaced by a carbonyl group, a $C_{5-7}$-1,2-cycloalkylene group optionally substituted by $R_c$ or $R_d$ or by $R_c$ and $R_d$, a $C_{5-7}$-1,2-cycloalkenylene group, a 1,2-arylene group, a 1,2-phenylene group in which one or two methine groups are each replaced by a nitrogen atom, whilst the above mentioned heterocyclic groups may additionally be substituted by one or two alkyl groups, or a CO—NH, NH—CO, CH=N or N=CH group optionally substituted by $R_c$ or $R_d$;

a first of the groups $R_a$ to $R_d$ denotes a group of the formula

A—B—C—

(wherein A denotes a $C_{1-5}$-aminoalkyl group, or an amino, amidino or guanidino group, whilst at one of the nitrogen atoms in each of the above mentioned groups one or two hydrogen atoms may each be replaced by an alkyl group or one hydrogen atom may be replaced by an alkoxycarbonyl group having a total of 2 to 5 carbon atoms, by a benzyloxycarbonyl group or by an $R_1$—CO—O—$(R_2CR_3)$—O—CO— group, wherein $R_1$ denotes a $C_{1-8}$-alkyl group, a $C_{5-7}$-cycloalkyl group or a phenyl or phenylalkyl group, $R_2$ denotes a hydrogen atom or an alkyl group and $R_3$ denotes a hydrogen atom, or A denotes a cyano or cyanoalkyl group, or if A is bound to a nitrogen atom of groups B or C which is not part of a lactam group, A may also denote a hydrogen atom, an alkyl group a benzyl group wherein the phenyl moiety may be substituted by one to two methoxy group, a formyl, acetyl or trifluoroacetyl group, an alkoxycarbonyl group having a total of 2 to 5 carbon atoms, a benzyloxycarbonyl group, or an $R_1$—CO—O—$(R_2CR_3)O$—CO— group, wherein $R_1$ to $R_3$ are as hereinbefore defined;

B denotes a bond, an alkylene group, an arylene group, a pyridinylene, pyrimidinylene, pyrazinylene or pyridazinylene group optionally substituted by one or two alkyl groups, a $C_{3-7}$-cycloalkylene group optionally substituted by one or two alkyl groups, a $C_{4-5}$-cycloalkylene group optionally substituted by a group $R_c$ and which may additionally be substituted by 1 to 4 alkyl groups and wherein, in the cycloalkylene moiety, a >CH unit is replaced by a nitrogen atom linked to the group A, wherein with the proviso that any heteroatom of the group $R_c$ is separated from the cyclic nitrogen atom of the cyclic imino group by at least two carbon atoms, $R_c$ denotes an alkyl, hydroxy, alkoxy, cyano, carboxy, alkoxycarbonyl, alkylcarbonyl, aminocarbonyl, alkylaminocarbonyl or dialkylamino carbonyl group, or B denotes a $C_{6-8}$-cycloalkylene group optionally substituted by a group $R_c$ and which may additionally be substituted by 1 to 4 alkyl groups and wherein, in the cycloalkylene moiety, a >CH unit is replaced by a nitrogen atom linked to the group A and additionally another >CH unit located in the 4-position may be replaced by a nitrogen atom, whilst furthermore in the above mentioned 6- to 8-membered rings one or two methylene groups adjacent to a nitrogen atom may each be replaced by a carbonyl group, whilst $R_c$ is as hereinbefore defined, a $C_{5-7}$-cycloalkenylene group optionally substituted by one or two alkyl groups and which may additionally be substituted by one or two methyl groups and wherein, in the cycloalkenylene moiety, a >CH unit is replaced by a nitrogen atom linked to the group A, wherein the nitrogen atom is separated from the double bond by at least one optionally mono- or di-substituted amethylene group, a piperidinylene group in which two hydrogen atoms on the carbon skeleton are replaced by a straight-chained alkylene bridge, this bridge containing 2 to 6 carbon atoms if it replaces two hydrogen atoms on the same carbon atom, or containing 1 to 5 carbon atoms if it replaces two hydrogen atoms on adjacent carbon atoms, or containing 1 to 4 carbon atoms if it replaces two hydrogen atoms on carbon atoms separated by a further atom, or containing 1 to 3 carbon atoms if it replaces two hydrogen atoms on carbon atoms separated by two further atoms, in which the above mentioned groups may each be substituted by one or two alkyl groups, or B denotes an alkylene group linked to the group C via a group W, wherein W represents an oxygen or sulphur atom or a sulphinyl, sulphonyl, $NR_4$, $NR_5CO$ or $CONR_5$ group, wherein $R_4$ denotes a hydrogen atom or an alkyl, alkylcarbonyl, alkylsulphonyl, arylcarbonyl or arylsulphonyl group and $R_5$ denotes a hydrogen atom or an alkyl group, or B together with A denotes a pyridyl group optionally substituted by one or two alkyl groups, or a piperidinyl group wherein the hydrogen atom in the 1-position together with a hydrogen atom in the 2-position is replaced by a straight-chained $C_{3-4}$-alkylene group, or a piperidinyl group in which the hydrogen atom in the 1-position together with a hydrogen atom in the 3-position is replaced by a straight-chained $C_{2-4}$-alkylene group, or a piperidinyl group in which the hydrogen atom in the 1-position together with a hydrogen atom in the 4-position is replaced by a straight-chained $C_{1-3}$-alkylene group, whilst a 4-position bound methylene group of an ethylene chain may be replaced by a hydroxymethylene or carbonyl group and additionally the nitrogen atom of these above mentioned bicyclic groups, which may be substituted in the carbon skeleton by one or two alkyl groups, may be completed by borane or quaternised by a benzyl group optionally substituted by one to two methoxy groups in the phenyl nucleus; and C denotes a $C_{1-6}$-alkylene group wherein a methylene group may be replaced by an oxygen or sulphur atom or by a sulphinyl, sulphonyl or $NR_4$ group, or wherein an ethylene group may be replaced by a $CONR_5$ or $NR_5CO$ group, wherein $R_4$ and $R_5$ are as hereinbefore defined, a $C_{2-6}$-alkenylene group, an alkylene carbonyl group having a total of 2 to 6 carbon atoms and linked to the group B via the carbonyl group, an arylene group, a pyridinylene, pyrimidinylene, pyrazinylene or pyridazinylene group, wherein one or two CH=N groups may each be replaced by a CO—NH group and one of the nitrogen atoms, instead of being bound to a hydrogen atom, may also be bound to the group B, provided that B does not represent a bond and B does not adjoin the group C with a heteroatom or a carbonyl group, whilst the above mentioned heterocyclic groups may additionally be substituted by one or two alkyl groups, a 5- to 7-membered cycloalkylene group optionally substituted by one or two alkyl groups, a cyclohexylene group in which two carbon atoms separated by three bonds are linked by a straight-chained $C_{1-3}$-alkylene group, whilst these bicyclic groups may also be substituted by 1 to 2 alkyl groups;

or C together with A and B denotes a pyridyl or 1,4-pyridyl-piperidinyl group optionally substituted by one or two alkyl groups, or a piperidinyl group in which the hydrogen atom in the 1-position together with a hydrogen atom in the 4-position is replaced by a straight-chained $C_{1-3}$-alkylene group, whilst a 4-position bound methylene group of an ethylene chain may be replaced by a hydroxymethylene or carbonyl group and additionally the nitrogen atom of these above mentioned bicyclic groups, which may be substituted by one or two alkyl groups in the carbon skeleton, may be completed by borane or quaternised by a benzyl group optionally substituted by 1 to 2 methoxy groups in the phenylnucleus, or if B denotes a bond, C may also represent (a) an indanylene, naphthylene, 1,2,3,4-tetrahydronapthylene or benzosuberanylene group wherein one of the rings is bound to the group A and the other ring is bound to the cyclic group of general formula I, whilst the saturated rings may each be substituted by one or two alkyl groups and the aromatic rings may each be substituted by a fluorine, chlorine, bromine or iodine atom, or by an alkyl, trifluoromethyl, hydroxy, alkoxy, alkylsulphenyl, alkylsulphinyl, alkylsulphonyl or cyano group, (b) a $C_{5-4}$-cycloalkylene group optionally substituted by a group $R_c$ and which may additionally be substituted by 1 to 4 alkyl groups and wherein, in the cycloalkylene moiety, a >CH unit is replaced by a nitrogen atom linked to the group A, whilst $R_c$ is as defined as hereinbefore, or (c) a piperidinylene group in which two hydrogen atoms on the carbon skeleton are replaced by a straight-chained alkylene bridge, this bridge containing 2 to 6 carbon atoms if it replaces two hydrogen atoms on the same carbon atom, or containing 1 to 5 carbon atoms if it replaces two hydrogen atoms on adjacent carbon atoms, or containing 1 to 4 carbon atoms if it replaces two hydrogen atoms on carbon atoms separated by a further atom, or containing 1 to 3 carbon atoms if it replaces two hydrogen atoms on carbon atoms separated by two further atoms, in which the above mentioned groups may each be substituted by one or two alkyl groups);

a second of the groups $R_a$ to $R_d$ denotes a group of formula

F—E—D—

(wherein D denotes a $C_{1-6}$-alkylene group wherein a methylene group may be replaced by an oxygen or sulphur atom or by a sulphinyl, sulphonyl or $NR_4$ group, or wherein an ethylene group may be replaced by a CO—$NR_5$ or $NR_5$—CO group, where $R_4$ and $R_5$ are as hereinbefore defined, an arylene group, a pyridinylene, pyrimidinylene, pyrazinylene or pyridazinylene group wherein one or two CH=N groups may each be replaced by a CO—NH group and one of the nitrogen atoms, instead of being bound to a hydrogen atom, may also be bound to the group E, provided that E does not denote a bond and E does not adjoin the group D with a heteroatom or a carbonyl group, whilst the above mentioned heterocyclic groups may additionally be substituted by one or two alkyl groups, an indanylene, naphthylene, 1,2,3,4-tetrahydronapthalene or benzosuberanylene group, in which one of the rings is bound to the group E and the other ring is bound to the cyclic group of general formula I, whilst the saturated rings may each be substituted by one or two alkyl groups and the aromatic rings may each be substituted by a fluorine, chlorine, bromine or iodine atom or by an alkyl, trifluoromethyl, hydroxy, alkoxy, alkylsulphenyl, alkylsulphinyl, alkylsulphonyl or cyano group, a $C_{4-7}$-cycloalkylene group optionally substituted by one or two alkyl groups, a $C_{5-7}$-cycloalkylene group optionally substituted by one or two alkyl groups and wherein a >CH unit is replaced by a nitrogen atom, whilst furthermore in the above mentioned 5–7-membered rings a methylene group adjacent to a nitrogen atom may be replaced by a carbonyl group, a piperazinylene group optionally substituted by one or two alkyl groups and wherein a methylene group adjacent to a nitrogen atom may be replaced by a carbonyl group, a cyclohexylene group in which two carbon atoms separated by three bonds are linked by a straight-chained $C_{1-3}$-alkylene group, whilst these bicyclic groups may also be substituted by 1 to 2 alkyl groups, or, if E is a cyclic imino group, D may also represent an alkylenecarbonyl group having a total of 2 to 6 carbon atoms, wherein the carbonyl group is bound to the nitrogen atom of the cyclic imino group of group E, or, if E is not a bond, D may represent a bond;

E denotes a bond, a $C_{1-6}$-alkylene group which may be substituted by one or two $C_{1-6}$-alkyl groups, by a hydroxy, amino or aryl group, by a $C_{1-6}$-alkoxy group or by an $HNR_6$- or N-alkyl-$NR_6$- group, wherein $R_6$ denotes an alkylcarbonyl or alkylsulphonyl group each having 1 to 6 carbon atoms in the alkyl moiety, an alkyloxycarbonyl group having a total of 2 to 5 carbon atoms, a cycloalkylcarbonyl or cycloalkylsulphonyl group each having 5 to 7 carbon atoms in the cycloalkyl moiety, or an arylalkylcarbonyl, arylalkylsulphonyl, arylalkoxycarbonyl, arylcarbonyl or arylsulphonyl group, or E denotes a $C_{2-6}$-alkenylene group, an arylene group, a pyridinylene, pyrimidinylene, pyrazinylene or pyridazinylene group optionally substituted by one or two alkyl groups, a $C_{5-7}$-cycloalkylene group optionally substituted by one or two alkyl groups and wherein a >CH unit is replaced by a nitrogen atom linked to a carbon atom of group D, a $C_{4-7}$-cycloalkylene group optionally substituted by one or two $C_{1-6}$-alkyl groups, by a hydroxy, amino or aryl group, by a $C_{1-6}$-alkoxy group or by an $HNR_6$- or N-alkyl-$NR_6$- group, wherein $R_6$ is as hereinbefore defined, or, if D does not represent a bond, E may denote an alkylene group linked to the group D via a group W, wherein W is as hereinbefore defined and the alkylene group may additionally be substituted by one or two $C_{1-6}$-alkyl groups, by a hydroxy, amino or aryl group, by a $C_{1-6}$-alkoxy group, or by an $HNR_6$- or N-alkyl-$NR_6$- group, in which the heteroatom of the additional substituent is separated from a heteroatom of group W by at least two carbon atoms and $R_6$ is as hereinbefore defined, and with the proviso that D together with E does not represent a —(CH$_2$)$_n$—CONH—CH$_2$CH$_2$— group, wherein n represents the number 1, 2, 3 or 4 and the ethylene moiety attached to the nitrogen atom may optionally be substituted as hereinbefore described, and F denotes a carbonyl group substituted by a hydroxy group, by a $C_{1-8}$-alkoxy group, by an arylalkoxy group or by an $R_7O$— group, wherein $R_7$ denotes a $C_{5-7}$-cycloalkyl group or a cycloalkylalkyl group having 5 to 7 carbon atoms in the cycloalkyl moiety, wherein the cycloalkyl group may be substituted by an alkyl group, by an alkyl group and by 1 to 3 methyl groups, or by an alkoxy group, and additionally a methylene group in a 5- to 7-membered cycloalkyl moiety may be replaced by an oxygen atom or by an alkylamino group, or $R_7$ denotes a $C_{9-12}$benzocycloalkyl group or an aryl group, or F denotes a phosphono, O-alkyl-phosphono, O,O'-dialkyl-phosphono, tetrazol-5-yl or $R_8CO$—O—CHR—O—CO— group, wherein $R_8$ denotes a $C_{1-8}$-alkyl or $C_{1-8}$-alkoxy group, a cycloalkyl or cycloalkyloxy group each having 5 to 7 carbon atoms in the cycloalkyl moiety, or an arylalkyl or arylalkoxy group and $R_9$ denotes a hydrogen atom or an alkyl group, and the shortest distance between group F and the furthest removed nitrogen atom of the group A—B—C— amounts to at least 11 bonds;

a third of the groups $R_a$ to $R_d$ denotes a hydrogen atom or an alkyl, trifluoromethyl, aryl or arylalkyl group); and the fourth of the groups $R_a$ to $R_d$ denotes a hydrogen atom or an alkyl or aryl group, whereby unless otherwise specified the aryl moieties mentioned in the definition of the above groups may be taken to mean a phenyl group which may be monosubstituted by $R_{10}$, mono-, di- or tri-substituted by $R_{11}$ or monosubstituted by $R_{10}$ and additionally mono- or di-substituted by $R_{11}$, whilst the substituents may be identical or different, and $R_{10}$ denotes a cyano, carboxy, aminocarbonyl, alkylamino-carbonyl, dialkylaminocarbonyl, alkoxycarbonyl, alkyl-carbonyl, alkylsulphenyl, alkylsulphinyl, alkylsulphonyl, alkylsulphonyloxy, trifluoromethyl, trifluoromethoxy, nitro, amino, alkylamino, dialkylamino, alkylcarbonylamino, phenylalkylcarbonylamino, phenylcarbonylamino, alkylsulphonylamino, phenylalkylsulphonylamino, phenylsulphonylamino, N-alkyl-alkylcarbonylamino, N-alkyl-phenylalkylcarbonylamino, N-alkyl-phenylcarbonylamino, N-alkyl-alkylsulphonylamino, N-alkyl-phenylalkylsulphonylamino, N-alkyl-phenylsulfonylamino, aminosulphonyl, alkylaminosulphonyl or dialkylaminosulphonyl group and $R_{11}$ denotes an alkyl, hydroxy or alkoxy group or a fluorine, chlorine, bromine or iodine atom, whilst two groups $R_{11}$, if they are bound to adjacent carbon atoms, may also represent a $C_{3-6}$-alkylene group, a 1,3-butadiene-1,4-diylene group or a methylenedioxy group, the arylene groups mentioned in the definition of the above groups may be taken to mean a phenylene group which may be monosubstituted by $R_{10}$, mono- or di-substituted by $R_{11}$, or monosubstituted by $R_{10}$ and additionally monosubstituted by $R_{11}$, whilst the substituents may be identical or different and are defined as hereinbefore, and unless otherwise specified the above mentioned alkyl, alkylene or alkoxy moieties may each contain 1 to 4 carbon atoms, and each carbon atom in the above mentioned alkylene and cycloalkylene moieties may be linked to not more than one heteroatom, the tautomers, stereoisomers and salts thereof.

Particularly preferred compounds of general formula I above are, with the exception of 1-(4-amidino-phenyl)-3-[4-(2-carboxy-ethyl)-cyclohexyl]-imidazolidin-2-one,
1-(4-amidino-phenyl)-3-[4-(2-methoxycarbonyl-ethyl)-cyclohexyl]-imidazolidin-2-one,
1-(4-cyano-phenyl)-3-[4-(2-methoxycarbonyl-ethyl)-cyclohexyl]-imidazolidin-2-one,
1-(4-amidino-phenyl)-3-[4-(2-phosphono-ethyl)-phenyl]-imidazolidin-2-one,
1-(4-amidino-phenyl)-3-(4-[2-(O-methyl-phosphono)-ethyl]-phenyl]-imidazolidin-2-one,
1-(4-cyano-phenyl)-3-[4-(2-phosphono-ethyl)-phenyl]-imidazolidin-2-one,
1-(4-cyano-phenyl)-3-[4-[2-(O-methyl-phosphono)-ethyl]-phenyl]-imidazolidin-2-one,
1-(4-aminomethyl-cyclohexyl)-3-[4-(2-carboxy-ethyl)-phenyl]-imidazolidin-2-one,
1-(4-aminomethyl-cyclohexyl)-3-[4-(2-methoxycarbonyl-ethyl)-phenyl]-imidazolidin-2-one,
1-(4-amidino-phenyl)-3-(4-(2-carboxy-ethyl)-phenyl]-4-phenyl-3H-imidazol-2-one,
1-(4-amidino-phenyl)-3-[4-(2-methoxycarbonyl-ethyl)-phenyl]-4-phenyl-3H-imidazol-2-one,
1-(4-amidino-phenyl)-3-[4-(2-carboxy-ethyl)-phenyl]-4-phenyl-imidazolidin-2-one,
1-(4-amidino-phenyl)-3-[4-(2-methoxycarbonyl-ethyl)-phenyl]-4-phenyl-imidazolidin-2-one,
4-(4-amidino-phenyl)-1-[4-(2-carboxy-ethyl)-phenyl]-3-phenyl-3H-imidazol-2-one,
4-(4-amidino-phenyl)-1-[4-(2-methoxycarbonyl-ethyl)-phenyl]-3-phenyl-3H-imidazol-2-one,
4-(4-cyano-phenyl)-1-[4-(2-methoxycarbonyl-ethyl)-phenyl]-3-phenyl-3H-imidazol-2-one,
4-(4-amidino-phenyl)-1-[4-(2-carboxy-ethyl)-phenyl]-5-methyl-3-phenyl-3H-imidazol-2-one,
4-(4-amidino-phenyl)-1-[4-(2-methoxycarbonyl-ethyl)-phenyl]-5-methyl-3-phenyl-3H-imidazol-2-one,
4-(4-cyano-phenyl)-1-[4-(2-methoxycarbonyl-ethyl)-phenyl]-5-methyl-3-phenyl-3H-imidazol-2-one,
4-(4-amidino-phenyl)-1-[4-(2-carboxy-ethyl)-phenyl]-3-phenyl-imidazolidin-2-one,
4-(4-amidino-phenyl)-1-[4-(2-methoxycarbonyl-ethyl)-phenyl]-3-phenyl-imidazolidin-2-one,
1-(4-amidino-phenyl)-4-[4-(2-carboxy-ethyl)-phenyl]-3-phenyl-3H-imidazol-2-one,
1-(4-amidino-phenyl)-4-[4-(2-methoxycarbonyl-ethyl)-phenyl]-3-phenyl-3H-imidazol-2-one,
1-(4-cyano-phenyl)-4-[4-(2-methoxycarbonyl-ethyl)-phenyl]-3-phenyl-3H-imidazol -2-one,
1-(4-amidino-phenyl)-4-[4-(2-carboxy-ethyl)-phenyl]-3-phenyl-imidazolidin-2-one,
1-(4-amidino-phenyl)-4-[4-(2-methoxycarbonyl-ethyl)-phenyl]-3-phenyl-imidazolidin-2-one,
1-(4-amidino-phenyl)-4-[4-(2-carboxy-ethyl)-phenyl]-5-methyl-3-phenyl-3H-imidazol-2-one,
1-(4-amidino-phenyl)-4-[4-(2-methoxycarbonyl-ethyl)-phenyl]-5-methyl-3-phenyl-3H-imidazol-2-one,
1-(4-cyano-phenyl)-4-[4-(2-methoxycarbonyl-ethyl)-phenyl]-5-methyl-3-phenyl-3H-imidazol-2-one,
1-(4-amidino-phenyl)-3-[4-(2-butyloxycarbonyl-ethyl)-phenyl]-imidazolidin-2-one,
2-(4-amidino-phenyl)-4-[4-(2-isopropyloxycarbonyl-ethyl)-phenyl]-5-methyl-4H-1,2,4-triazol-3-one,
4-[4-(2-isopropyloxycarbonyl-ethyl)-phenyl]-2-(4-methoxy-carbonylamidino-phenyl)-5-methyl-4H-1,2,4-triazol-3-one,
1-(4-amidino-phenyl)-3-[4-(2-ethoxycarbonyl-ethyl)-phenyl]-3H-imidazol-2-one,
1-(4-ethoxycarbonylamidino-phenyl)-3-[4-(2-ethoxycarbonyl-ethyl)-phenyl]-3H-imidazol-2-one,
1-(4-ethoxycarbonylamidino-phenyl)-3-[4-(2-ethoxycarbonyl-ethyl)-phenyl]-imidazolidin-2-one,
1-(4-methoxycarbonylamidino-phenyl)-3-[4-(2-methoxycarbonyl-ethyl)-cyclohexyl]-imidazolidin-2-one,
4-[4-(2-isobutyloxycarbonyl-ethyl)-phenyl]-2-(4-methoxy-carbonylamidino-phenyl)-5-methyl-4H-1,2,4-triazol-3-one,
2-(4-amidino-phenyl)-4-[4-(2-isobutyloxycarbonyl-ethyl)-phenyl]-5-methyl-4H-1,2,4-triazol-3-one,
1-(1-amino-5-indanyl)-3-[4-(2-carboxy-ethyl)-phenyl]-imidazolidin-2-one,
1-(1-amino-5-indanyl)-3-[4-(2-methoxycarbonyl-ethyl)-phenyl]-imidazolidin-2-one,
1-(1-amino-1,2,3,4-tetrahydro-6-naphthyl)-3-[4-(2-carboxy-ethyl)-phenyl)-imidazolidin-2-one,
1-(1-amino-1,2,3,4-tetrahydro-6-naphthyl)-3-[4-(2-methoxy-carbonyl-ethyl)-phenyl]-imidazolidin-2-one,
1-(4-amino-cyclohexyl)-3-[4-(3-carboxy-propyl)-phenyl]-imidazolidin-2-one,
1-(4-amino-cyclohexyl)-3-[4-(3-methoxycarbonyl-propyl)-phenyl]-imidazolidin-2-one,
1-(4-amino-cyclohexyl)-3-[4-(2-carboxy-ethyl)-phenyl]-imidazolidin-2-one,
1-(4-amino-cyclohexyl)-3-[4-(2-methoxycarbonyl-ethyl)-phenyl]-imidazolidin-2-one,
1-(4-aminomethyl-phenyl)-3-[3-(2-carboxy-ethyl)-phenyl]-imidazolidin-2-one,
1-(4-aminomethyl-phenyl)-3-[3-(2-methoxycarbonyl-ethyl)-phenyl]-imidazolidin-2-one,
1-[4-(1-amino-cyclopropyl)-phenyl]-3-[4-(2-carboxyethyl)-phenyl]-imidazolidin-2-one,
1-[4-(1-amino-cyclopropyl)-phenyl]-3-[4-(2-methoxycarbonyl-ethyl)-phenyl]-imidazolidin-2-one,
1-[4-(1-amino-cyclopentyl)-phenyl]-3-[4-(2-carboxyethyl)-phenyl]-imidazolidin-2-one,
1-[4-(1-amino-cyclopentyl)-phenyl]-3-[4-[(2-methoxycarbonyl-ethyl)-phenyl]-imidazolidin-2-one,
2-(4-amidino-phenyl)-5-ethyl-4-[4-(2-isopropyloxycarbonyl-ethyl)-phenyl]-4H-1,2,4-triazol-3-one,
1-(4-amidino-phenyl)-3-[4-(2-isopropyloxycarbonylethyl)-phenyl]-4-methyl-3H-imidazol-2-one,
4-(4-amidino-phenyl)-2-[4-(2-isopropyloxycarbonylethyl)-phenyl]-4H-1,2,4-triazol-3-one,
1-(4-amidino-phenyl)-3-[4-(2-isopropyloxycarbonylethyl)-phenyl]-imidazolidin-2-one,
1-(4-amidino-phenyl)-3-[4-(2-isopropyloxycarbonyl-ethyl)-phenyl]-3H-imidazol-2-one,
1-(4-amidino-phenyl)-3-[4-(2-isopropyloxycarbonylethyl)-phenyl]-imidazolidin-2,4-dione,
2-(4-amidino-phenyl)-4-[4-(2-phosphono-ethyl)-phenyl]-5-methyl-4H-1,2,4-triazol-3-one,
2-(4-amidino-phenyl)-4-[4-[2-(O-methyl-phosphono)-ethyl]-phenyl]-5-methyl-4H-1,2,4-triazol-3-one,
2-(4-amidino-phenyl)-4-[4-(2-carboxy-ethyl)-phenyl]-5-phenyl-4H-1,2,4-triazol-3-one,
2-(4-amidino-phenyl)-4-[4-(2-methoxycarbonyl-ethyl)-phenyl]-5-phenyl-4H-1,2,4-triazol-3-one, 3-(4-amidino-phenyl)-1-[4-(2-carboxy-ethyl)-phenyl]-4-trifluoromethyl-3H-imidazol-2-one, 3-(4-amidino-phenyl)-1-[4-(2-methoxycarbonyl-ethyl)-phenyl]-4-trifluoromethyl-3H-imidazol-2-one, 2-(4-amidino-phenyl)-4-[4-(2-carboxy-ethyl)-phenyl]-5-trifluoromethyl-4H-1,2,4-triazol-3-one, 2-(4-amidino-phenyl)-4-(4-(2-methoxycarbonyl-ethyl)-phenyl]-5-trifluoromethyl-4H-1,2,4-triazol-3-one and 3-(4-cyano-phenyl)-1-(4-ethoxycarbonyl-butyl)-3H-imidazo-[4,5-b]pyridin-2-one and with the proviso that at least one of conditions (i) to (ix) below is satisfied (i) X denotes a carbimino group substituted by-a cyano group at the nitrogen atom, (ii) Y denotes a 1,2-cyclopentylene or 1,2-cyclohexylene group optionally substituted by one or two alkyl groups, (iii) A denotes an amidino group substituted by an $R_1$—CO—O—$(R_2CR_3)$—O—CO— group, (iv) B denotes a pyrrolidinylene group optionally substituted by one or two alkyl groups, a piperidinylene group optionally substituted by 1 to 4 alkyl groups and which may additionally be substituted in the 4-position by a cyano, aminocarbonyl, alkylaminocarbonyl, dialkylaminocarbonyl, alkylcarbonyl or alkoxy group, a piperidinylene group in which two hydrogen atoms on the carbon skeleton are replaced by a straight-chained alkylene group, this bridge containing 2 to 5 carbon atoms if it replaces two hydrogen atoms on the same carbon atom, or containing 1 to 4 carbon atoms if it replaces two hydrogen atoms on adjacent carbon atoms, or containing 2 to 3 carbon atoms if it replaces two hydrogen atoms on carbon atoms separated by a further atom, or containing 1 or 2 carbon atoms if it replaces two hydrogen atoms on carbon atoms separated by two further atoms, a 1,2,3,6-tetrahydro-pyridinylene group optionally substituted by one or two alkyl groups, an azacycloheptylene group optionally substituted by one or two alkyl groups, a piperazinylene group optionally substituted by one or two alkyl groups, a 2-oxo-piperazinylene group optionally substituted by one or two alkyl groups, an alkyleneoxy group, a $C_{3-6}$-cycloalkylene group optionally substituted by one or two alkyl groups or B together with A denotes a pyridyl group optionally substituted by one or two alkyl groups, or a piperidinyl group in which the hydrogen atom in the 1-position together with a hydrogen atom in the 4-position is replaced by a methylene, ethylene or 1,3-propylene group, whilst a 4-position bound methylene group of an ethylene chain may be replaced by a carbonyl or hydroxymethylene group, and additionally the nitrogen atom of the above mentioned bicyclic groups, which may additionally be substituted by one or two alkyl groups in the carbon skeleton, may be complexed by borane or quaternised by a benzyl group, (v) C denotes an alkyleneoxy group, a cyclohexylene group in which two carbons separated by three bonds can additionally be linked by a methylene or ethylene group, a piperidinylene group optionally substituted by one or two alkyl groups or an indanylene, napthylene or 1,2,3,4-tetrahydronaphthylene group or C together with A and B denotes a pyridyl or 1-(4-pyridyl)-piperidinyl group optionally substituted by one or two alkyl groups, or a piperidinyl group in which the hydrogen atom in the 1-position together with a hydrogen atom in the 4-position is replaced by a methylene or ethylene group and additionally the nitrogen atom of these above mentioned bicyclic groups, which may additionally be substituted by one or two alkyl groups in the carbon skeleton, may be complexed by borane or quaternised by a benzyl group, or C denotes a $C_{1-6}$-alkylene group and B is a bond, (vi) D denotes a 1,3-arylene group, a $C_{5-7}$-cycloalkylene group optionally substituted by one or two alkyl groups, a cyclohexylene group in which two carbon atoms separated by three bonds are additionally linked by a methylene or ethylene group, or D denotes an indanylene, naphthylene or 1,2,3,4-tetrahydronaphthylene group, (vii) E denotes a straight-chained alkylene group which is substituted by a $C_{1-6}$-alkyl group, by an aryl group or by an $HNR_6$- group, an alkyleneoxy group linked to the group D via the oxygen atom, and which is substituted by a $C_{1-6}$-alkyl group, by an aryl, hydroxy or amino group, by a $C_{1-6}$-alkoxy group or by an $HNR_6$- group, or E denotes a piperidinylene group optionally substituted by one or two alkyl groups, (viii) F denotes an alkoxycarbonyl group having a total of 3 to 7 carbon atoms, an $R_7O$—CO—, phosphono, O-alkyl-phosphono, O,O'-dialkyl-phosphono or $R_8CO$—O—$CHR_9$—O—CO— group and (ix) the third of the groups $R_a$ to $R_d$ denotes a trifluoromethyl or aryl group, those wherein:

X denotes a carbimino group substituted by a cyano group at the nitrogen atom, or X denotes a carbonyl or sulphonyl group, Y denotes a $CH_2CH_2$, $CH_2CH_2CH_2$, CH=CH, $CH_2CO$ or $COCH_2$ group optionally substituted by $R_c$ or by $R_c$ and $R_d$, or Y denotes an N=CH or CH=N group optionally substituted by $R_c$, a 1,2-arylene group, a 1,2-phenylene group in which one or two methine groups are each replaced by a nitrogen atom, whilst the above mentioned heterocyclic groups may additionally be substituted by one or two alkyl groups, or Y denotes a 1,2-cyclopentylene or 1,2-cyclohexylene group optionally substituted by one or two alkyl groups;

a first of the groups $R_a$ to $E_d$ denotes a group of the formula

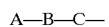

(wherein A denotes an amidino group optionally substituted by an alkoxycarbonyl group having a total of two or three carbon atoms or by a benzyloxycarbonyl or $R_1$—CO—O—$(R_2CR_3)$—O—CO— group, wherein $R_1$ denotes an alkyl group, $R_2$ denotes a hydrogen atom or a methyl group and $R_3$ denotes a hydrogen atom, or A denotes a cyano, cyanomethyl, cyanoethyl, amino, aminomethyl, aminoethyl or aminopropyl group or, if A is bound to a nitrogen atom of the groups B or C, A may denote a hydrogen atom, a methyl, ethyl, benzyl, tert.butyloxycarbonyl, benzyloxycarbonyl, trifluoroacetyl or $R_1$—CO—O—($R_2CR_3$)—O—CO— group, wherein $R_1$ to $R_3$ are as hereinbefore defined, B denotes a bond, a pyrrolidinylene group optionally substituted by one or two alkyl groups, a piperidinylene group optionally substituted by 1 to 4 alkyl groups, which may additionally be substituted in the 4-position by a cyano, aminocarbonyl, alkylaminocarbonyl, dialkylaminocarbonyl, alkylcarbonyl or alkoxy group, a piperidinylene group in which two hydrogen atoms on the carbon skeleton are replaced by a straight-chained alkylene group, this bridge containing 2 to 5 carbon atoms if it replaces two hydrogen atoms on the same carbon atom, or containing 1 to 4 carbon atoms if it replaces two hydrogen atoms on adjacent carbon atoms, or containing 2 to 3 carbon atoms if it replaces two hydrogen atoms on carbon atoms separated by a further atom, or containing one or two carbon atoms if it replaces two hydrogen atoms on carbon atoms separated by two further atoms, a 1,2,3,6-tetrahydropyridinylene group optionally substituted by one or two alkyl groups, an azacycloheptylene group optionally substituted by one or two alkyl groups, a piperazinylene group optionally substituted by one or two alkyl groups, wherein a nitrogen atom of the cyclic imino groups mentioned above in the definition of group B is linked to group A, a 2-oxo-piperazinylene group optionally substituted by one or two alkyl groups, wherein the nitrogen atom in the 4-position is linked to the group A, an alkylene group, an alkyleneoxy group, wherein the oxygen atom is linked to the group C and the nitrogen atoms of group A are separated from the oxygen atom by at least two carbon atoms, a $C_{3-6}$-cycloalkylene group optionally substituted by one or two alkyl groups or B together with A denotes a pyridyl group optionally substituted by one or two alkyl groups, or a piperidinyl group in which the hydrogen atom in the 1-position together with a hydrogen atom in the 4-position is replaced by a methylene, ethylene or 1,3-propylene group, whilst a 4-position bound methylene group of an ethylene chain may be replaced by a carbonyl or hydroxymethylene group and additionally the nitrogen atom of the above mentioned bicyclic groups, which may additionally be substituted by one or two alkyl groups in the carbon skeleton, may be complexed by borane or quaternised by a benzyl group, and C denotes a $C_{1-6}$-alkylene group, an alkyleneoxy group in which the oxygen atom is bound to a carbon atom of group B or to one of the bicyclic groups formed by B together with A and between the oxygen atom of the alkyleneoxy group and the nitrogen atom of the cyclic group of general formula I there are at least two carbon atoms, a $C_{2-4}$-alkenylene group, although this cannot be linked to a heteroatom of group A, of group B or of the cyclic group of general formula I via a vinylene moiety, or C denotes a cyclohexylene group in which two carbon atoms separated by three bonds, are additionally linked by a methylene or ethylene group, an arylene group or a pyridinylene, pyrimidinylene, pyrazinylene or pyridazinylene group optionally substituted by one or two alkyl groups, if B denotes a piperazinylene group optionally substituted by one or two alkyl groups, C may also denote an alkylenecarbonyl group, in which the carbonyl group is attached to the optionally mono- or di-alkyl substituted nitrogen atom of the piperazinylene B group, or C together with A and B represents a pyridyl or 1-(4-pyridyl)-piperidinyl group optionally substituted by one or two alkyl groups, or a piperidinyl group in which the hydrogen atom in the 1-position together with a hydrogen atom in the 4-position is replaced by a methylene or ethylene group, and additionally the nitrogen atom of these above mentioned bicyclic groups, which may additionally be substituted by one or two alkyl groups in the carbon skeleton, may be complexed by borane or quaternised by a benzyl group, or if B denotes a bond, C may also represent a piperidinylene group optionally substituted by one or two alkyl groups, wherein the nitrogen atom is linked to the group A, or an indanylene, naphthylene or 1,2,3,4-tetrahydro-naphthylene group, wherein one of the rings is bound to the group A and the other ring to the cyclic group of general formula I);

a second of groups $R_a$ to $R_d$ denotes a group of formula

F—E—D—

(wherein D denotes an alkylene group, an arylene group, a pyridinylene, pyrimidinylene, pyrazinylene or pyridazinylene group optionally substituted by one or two alkyl groups, a $C_{5-7}$-cycloalkylene group optionally substituted by one or two alkyl groups, a cyclohexylene group in which two carbon atoms separated by three bonds are additionally linked by a methylene or ethylene group, an indanylene, naphthylene or 1,2,3,4-tetrahydronaphthylene group, wherein one of the rings is bound to the group E and the other ring to the cyclic group of general formula I, or, if E denotes a piperidinylene group optionally substituted by one or two alkyl groups, D may also denote an alkylenecarbonyl group in which the carbonyl group is attached to the optionally mono- or di-alkyl substituted nitrogen atom of the piperidinylene E group;

E denotes a bond, a $C_{2-4}$-alkenylene group, an alkylene group which may be substituted by a $C_{1-6}$-alkyl group, by an aryl, hydroxy or amino group, by a $C_{1-6}$-alkoxy group or by an $HNR_6$- group, whilst $R_6$ denotes an alkylcarbonyl or alkylsulphonyl group each having 1 to 6 carbon atoms in the alkyl moiety, a cycloalkylcarbonyl or cycloalkylsulphonyl group each having 5 to 7 carbon atoms in the cycloalkyl moiety, or an arylcarbonyl, arylsulphonyl, arylalkylcarbonyl or arylalkylsulphonyl group, or E denotes an alkyleneoxy group linked to group D via the oxygen atom and which may be substituted by a $C_{1-6}$-alkyl group, by an aryl, hydroxy or amino group, by a $C_{1-6}$-alkoxy group or by an $HNR_6$- group, in which the heteroatom of the additional substituent is separated from the oxygen atom of the alkyleneoxy group by at least two carbon atoms and $R_6$ is as hereinbefore defined, or E denotes an arylene group, a cyclohexylene group optionally substituted by one or two alkyl groups or, if D is an alkylenecarbonyl group, E may denote a piperidinylene group optionally substituted by one or two alkyl groups, wherein the nitrogen atom is linked to the carbonyl group of the alkylenecarbonyl group of group D; and F denotes a carbonyl group substituted by a hydroxy group, by a $C_{1-6}$-alkoxy group, by an arylalkoxy group or by an $R_7O$— group, wherein $R_7$ denotes a $C_{5-7}$-cycloalkyl group, a cycloalkylalkyl group having 5 to 7 carbon atoms in the cycloalkyl moiety, a $C_{9-11}$-benzocycloalkyl group or an aryl group, or F denotes a phosphono, O-alkyl-phosphono, O,O'-dialkyl-phosphono, tetrazol-5-yl or $R_8CO$—O—CHR—O—CO— group, wherein $R_8$ denotes a cycloalkyl or cycloalkyloxy group each having 5 to 7 carbon atoms in the cycloalkyl moiety, a $C_{1-6}$-alkyl or $C_{1-6}$-alkoxy group and $R_9$ denotes a hydrogen atom or an alkyl group, and the shortest distance between group F and the furthest removed nitrogen atom of the group A—B—C— amounts to at least 11 bonds);

a third of the groups $R_a$ to $R_d$ denotes a hydrogen atom or an alkyl, trifluoromethyl, aryl or arylalkyl group; and the fourth of the groups $R_a$ to $R_d$ denotes a hydrogen atom or an alkyl group, whilst, unless otherwise specified, the aryl moieties mentioned in the definition of the above mentioned groups may be taken to mean a phenyl group which may be monosubstituted by $R_{10}$, mono- or di-substituted by $R_{11}$, or monosubstituted by $R_{10}$ and additionally monosubstituted by $R_{11}$, wherein the substituents may be identical or different and $R_{10}$ denotes a cyano, aminocarbonyl, alkylaminocarbonyl, dialkylaminocarbonyl, alkylcarbonyl, alkylsulphenyl, alkylsulphinyl, alkylsulphonyl, alkylsulphonyloxy, trifluoromethyl, nitro, amino, alkylcarbonylamino, N-alkyl-alkylcarbonylamino, alkylsulfonylamino or N-alkyl-alkylsulphonylamino group and $R_{11}$ denotes an alkyl, hydroxy or alkoxy group or a fluorine, chlorine or bromine atom, while two groups $R_{11}$ provided that they are bound to adjacent carbon atoms, may also denote a $C_{3-4}$-alkylene group, a 1,3-butadiene-1,4-diylene group or a methylenedioxy group, the arylene moieties mentioned in the definition of the above mentioned groups may be taken to mean a phenylene group which may be monosubstituted by $R_{10}$, mono- or di-substituted by $R_{11}$, or monosubstituted by $R_{10}$ and additionally monosubstituted by $R_{11}$, wherein the substituents may be identical or different and are defined as hereinbefore, and unless otherwise specified the above mentioned alkyl, alkylene or alkoxy moieties may each contain 1 to 4 carbon atoms and each carbon atom in the above mentioned alkylene and cycloalkylene moieties is linked to not more than one heteroatom, particularly those compounds, with the exception of 1-(4-amidino-phenyl)-3-[4-(2-carboxy-ethyl)-cyclohexyl]-imidazolidin-2-one, 1-(4-amidino-phenyl)-3-[4-(2-methoxycarbonyl-ethyl)-cyclohexyl]-imidazolidin-2-one, 1-(4-amidino-phenyl)-3-[4-(2-phosphono-ethyl)-phenyl]-imidazolidin-2-one, 1-(4-amidino-phenyl)-3-[4-[2-(O-methyl-phosphono)-ethyl]-phenyl]-imidazolidin-2-one, 1-(4-aminomethyl-cyclohexyl)-3-[4-(2-carboxy-ethyl)-phenyl]-imidazolidin-2-one, 1-(4-aminomethyl-cyclohexyl)-3-[4-(2-methoxycarbonyl-ethyl)-phenyl]-imidazolidin-2-one, 1-(4-amidino-phenyl)-3-[4-(2-butyloxycarbonyl-ethyl)-phenyl]-imidazolidin-2-one, 2-(4-amidino-phenyl)-4-[4-(2-isopropyloxycarbonyl-ethyl)-phenyl]-5-methyl-4H-1,2,4-triazol-3-one, 1-(4-amidino-phenyl)-3-[4-(2-ethoxycarbonyl-ethyl)-phenyl]-3H-imidazol-2-one, 2-(4-amidino-phenyl)-4-[4-(2-isobutyloxycarbonyl-ethyl)-phenyl]-5-methyl-4H-1,2,4-triazol-3-one, 1-(4-amino-cyclohexyl)-3-[4-(3-carboxy-propyl)-phenyl]-imidazolidin-2-one, 1-(4-amino-cyclohexyl)-3-[4-(3-methoxycarbonyl-propyl)-phenyl]-imidazolidin-2-one, 1-(4-amino-cyclohexyl)-3-[4-(2-carboxy-ethyl)-phenyl]-imidazolidin-2-one, 1-(4-amino-cyclohexyl)-3-[4-(2-methoxycarbonyl-ethyl)-phenyl]-imidazolidin-2-one, 1-(4-aminomethyl-phenyl)-3-[3-(2-carboxy-ethyl)-phenyl]-imidazolidin-2-one, 1-(4-aminomethyl-phenyl)-3-(3-(2-methoxycarbonyl-ethyl)-phenyl]-imidazolidin-2-one, 1-(4-amidino-phenyl)-3-[4-(2-isopropyloxycarbonyl-ethyl)-phenyl]-4-methyl-3H-imidazol-2-one, 4-(4-amidino-phenyl)-2-[4-(2-isopropyloxycarbonyl-ethyl)-phenyl]-4H-1,2,4-triazol-3-one, 1-(4-amidino-phenyl)-3-[4-(2-isopropyloxycarbonyl-ethyl)-phenyl]-imidazolidin-2-one, 1-(4-amidino-phenyl)-3-[4-(2-isopropyloxycarbonyl-ethyl)-phenyl]-3H-imidazol-2-one, 1-(4-amidino-phenyl)-3-[4-(2-isopropyloxycarbonyl-ethyl)-phenyl]-imidazolidin-2,4-dione, 2-(4-amidino-phenyl)-4-[4-(2-phosphono-ethyl)-phenyl]-5-methyl-4H-1,2,4-triazol-3-one and 2-(4-amidino-phenyl)-4-[4-[2-(O-methyl-phosphono)-ethyl]-phenyl]-5-methyl-4H-1,2,4-triazol-3-one, and with the proviso that at least one of conditions (i) to (viii) below must be satisfied (i) X denotes a carbimino group substituted at the nitrogen atom by a cyano group, (ii) Y denotes a 1,2-cyclohexylene group, (iii) A denotes an amidino group substituted by an $R_1$—CO—O—$(R_2CR_3)$—O—CO— group, (iv) B denotes a 1,3-pyrrolidinylene or 1,3-piperidinylene group, a 1,4-piperidinylene group optionally substituted by one to four methyl groups and which may additionally be substituted in the 4-position by a cyano or aminocarbonyl group, a 1,4-azacycloheptylene group, a 1,4-piperazinylene group, a 2-oxo-1,4-piperazinylene group, a —$CH_2CH_2$— group, or a 1,2-cyclopentylene group or B together with A denotes a 4-piperidinyl group in which the hydrogen atom in the 1-position together with a hydrogen atom in the 4-position is replaced by a methylene or ethylene group, wherein a 4-position bound methylene group of an ethylene chain may be replaced by a carbonyl group, (v) C denotes an —O—CH$_2$— or —O—CH$_2$CH$_2$— group, a 1,4-cyclohexylene group in which a hydrogen atom in the 1-position together with a hydrogen atom in the 4-position may be replaced by an ethylene group, a 1,4-piperidinylene group, a 1,2,3,4-tetrahydro-2,6-naphthylene group or C together with A and B denotes a 4-piperidinyl group in which the hydrogen atom in the 1-position together with a hydrogen atom in the 4-position is replaced by a methylene or ethylene group, or C denotes a C$_{1-4}$-alkylene group and B is a bond, (vi) D denotes a 1,3-phenylene group optionally substituted by a fluorine or chlorine atom or by a methyl, trifluoromethyl or cyano group, a 1,4-cyclohexylene group wherein a hydrogen atom in the 1-position together with a hydrogen atom in the 4-position may be replaced by an ethylene group, or D denotes a 1,5-indanylene, 2,6-naphthylene or 1,2,3,4-tetrahydro-2,6-naphthylene group, (vii) E denotes a straight-chained C$_{1-4}$-alkylene group which is substituted by a C$_{1-4}$-alkyl group, by a phenyl group or by a C$_{1-4}$-alkylsulphonylamino group, or E denotes a 1,4-piperidinylene group, (viii) F denotes an alkoxycarbonyl group having a total of 3 to 6 carbon atoms, or an R$_7$—CO—, R$_8$CO—O—CHR$_9$—O—CO—, phosphono, O-methyl-phosphono or O-ethyl-phosphono group;

wherein:

X denotes a carbimino group substituted by a cyano group at the nitrogen atom, or X denotes a carbonyl or sulphonyl group;

Y denotes a CH$_2$CH$_2$, CH$_2$CH$_2$CH$_2$, CH═CH, CH$_2$CO or COCH$_2$ group optionally substituted by R$_c$ or by R$_c$ and R$_d$, an N═CH or CH═N group optionally substituted by R$_c$, or a 1,2-phenylene or 1,2-cyclohexylene group;

a first of groups R$_a$ to R$_d$ denotes a group of the formula

A—B—C—

(wherein A denotes an amidino group optionally substituted by an R$_1$—CO—O—(R$_2$CR$_3$)—O—CO— group, wherein R$_1$ denotes a methyl group, R$_2$ denotes a hydrogen atom or a methyl group and R$_3$ denotes a hydrogen atom, or A denotes an amino or aminomethyl group or, if A is bound to a nitrogen atom of groups B or C, it may also denote a hydrogen atom or a methyl group, B denotes a bond, a 1,3-pyrrolidinylene or 1,3-piperidinylene group, a 1,4-piperidinylene group optionally substituted by one to four methyl groups and which may additionally be substituted in the 4-position by a cyano or aminocarbonyl group, a 1,4-azacycloheptylene group, a 1,4-piperazinylene group, wherein a nitrogen atom of the group mentioned above in the definition of group B is linked to group A, a 2-oxo-1,4-piperazinylene group wherein the nitrogen atom in the 4-position is linked to the group A, a —CH$_2$CH$_2$O— group, wherein the oxygen atom is linked to the group C, a 1,2-cyclopentylene group, or B together with A denotes a 4-piperidinyl group in which the hydrogen atom in the 1-position together with a hydrogen atom in the 4-position is replaced by a methylene or ethylene group, whilst a 4-position bound methylene group of an ethylene chain may be replaced by a carbonyl group; and C denotes a C$_{1-4}$-alkylene group, an —O—CH$_2$— or —O—CH$_2$CH$_2$— group, wherein the oxygen atom is bound to a carbon atom of group B or to one of the bicyclic groups formed by B together with A and the methylene group of the —O—CH$_2$— group is bound to a carbon atom of the cyclic group of general formula I, a 1,4-cyclohexylene group in which a hydrogen atom in the 1-position together with a hydrogen atom in the 4-position may be replaced by an ethylene group, a 1,4-phenylene group, or C together with A and B denotes a 4-piperidinylene group in which the hydrogen atom in the 1-position together with a hydrogen atom in the 4-position is replaced by a methylene or ethylene group, or, if B is a 1,4-piperazinylene group, C may also represent a —CO—CH$_2$— group, wherein the carbonyl group is bound to a nitrogen atom of the 1,4-piperazinylene group of group B, or if B denotes a bond, C may also represent a 1,4-piperidinylene group in which the nitrogen atom is linked to the group A, or a 1,2,3,4-tetrahydro-2,6-naphthylene group which is linked in the 2-position to the group A);

a second of the groups R$_a$ to R$_d$ denotes a group of the formula

F—E—D—

(wherein D denotes a C$_{1-4}$-alkylene group, a 1,3- or 1,4-phenylene group optionally substituted by a fluorine or chlorine atom or by a methyl, trifluoromethyl or cyano group, a 1,4-cyclohexylene group in which a hydrogen atom in the 1-position together with a hydrogen atom in the 4-position may be replaced by an ethylene group, a 1,5-indanylene, 2,6-naphthylene or 1,2,3,4-tetrahydro-2,6-naphthylene group, or, if E is a 1,4-piperidinylene group, D may also represent a —CO—CH$_2$— group, in which the carbonyl group is linked to the nitrogen atom of the 1,4-piperidinylene group of group E, E denotes a bond, a —CH═CH— group, a C$_{1-4}$-alkylene group which may be substituted by a C$_{1-4}$-alkyl group, by a phenyl group or by a C$_{1-4}$-alkylsulphonylamino group, an —O—CH$_2$— group, wherein the oxygen atom is linked to the group D, a 1,4-cyclohexylene group, or, if D is a —COCH$_2$— group, E may also represent a 1,4-piperidinylene group, wherein the nitrogen atom is linked to the carbonyl gruop of the —COCH$_2$— group of group D; and F denotes a carbonyl group which is substituted by a hydroxy group, by a $C_{1-5}$-alkoxy group, by a phenylalkoxy group having 1 to 3 carbon atoms in the alkoxy moiety, or by an $R_7O—$ group, wherein $R_7$ denotes a $C_{5-7}$-cycloalkyl group or a cyclohexylmethyl or indanyl group, or F denotes an $R_8CO—O—CHR_9—CO—$, phosphono, O-methyl-phosphono or O-ethyl-phosphono group, wherein $R_8$ denotes a cycloalkyloxy group having 5 to 7 carbon atoms in the cycloalkyl moiety, or a $C_{1-4}$-alkyl or $C_{1-4}$-alkoxy group, and $R_9$ denotes a hydrogen atom or a methyl group, and the shortest distance between group F and the furthest removed nitrogen atom of the group A—B—C— amounts to at least 11 bonds;)

a third of the groups $R_a$ to $R_d$ denotes a hydrogen atom or a methyl, trifluoromethyl or phenyl group; and the fourth of the groups $R_a$ to $R_4$ denotes a hydrogen atom or a methyl group;

and each carbon atom in the above mentioned alkylene and cycloalkylene moieties is linked to at most one heteroatom;

the tautomers, stereoisomers and salts thereof.

The most particularly preferred compounds of general formula I are, with the exception of 1-(4-amidino-phenyl)-3-[4-(2-phosphono-ethyl)-phenyl]-imidazolidin-2-one, 1-(4-amidino-phenyl)-3-[4-(2-butyloxycarbonyl-ethyl)-phenyl]-imidazolidin-2-one, 2-(4-amidino-phenyl)-4-[4-(2-isopropyloxycarbonyl-ethyl)-phenyl]-5-methyl-4H-1,2,4-triazol-3-one, 1-(4-amidino-phenyl)-3-[4-(2-ethoxycarbonyl-ethyl)-phenyl]-3H-imidazol-2-one, 2-(4-amidino-phenyl)-4-[4-(2-isobutyloxycarbonyl-ethyl)-phenyl]-5-methyl-4H-1,2,4-triazol-3-one, 1-(4-aminomethyl-phenyl)-3-[3-(2-carboxy-ethyl)-phenyl]-imidazolidin-2-one, 1-(4-aminomethyl-phenyl)-3-[3-(2-methoxycarbonyl-ethyl)-phenyl]-imidazolidin-2-one, 1-(4-amidino-phenyl)-3-[4-(2-isopropyloxycarbonyl-ethyl)-phenyl]-4-methyl-3H-imidazol-2-one, 1-(4-amidino-phenyl)-3-[4-(2-isopropyloxycarbonyl-ethyl)-phenyl]-imidazolidin-2-one, 1-(4-amidino-phenyl)-3-[4-(2-isopropyloxycarbonyl-ethyl)-phenyl]-3H-imidazol-2-one, 1-(4-amidino-phenyl)-3-[4-(2-isopropyloxycarbonyl-ethyl)-phenyl]-imidazolidin-2,4-dione and 2-(4-amidino-phenyl)-4-[4-(2-phosphono-ethyl)-phenyl]-5-methyl-4H-1,2,4-triazol-3-one, and with the proviso that at least one of conditions (i) to (viii) below must be satisfied (i) X denotes a carbimino group substituted by a cyano group at. the nitrogen atom, (ii) Y denotes a 1,2-cyclohexylene group, (iii) A denotes an amidino group substituted by an $R_1—CO—O—(R_2CR_3)—O—CO—$ group, (iv) B denotes a 1,4-azacycloheptylene group, a 1,4-piperidinylene group optionally substituted by 1 to 4 methyl groups and which may additionally be substituted in the 4-position by a cyano or aminocarbonyl group, a 1,4-piperazinylene group, or A and B together denote a 2-amino-ethoxy or 4-quinuclidinyl group, (v) C denotes a 1,4-piperidinylene, 1,2,3,4-tetrahydro-2,6-naphthylene or 1,4-bicyclo[2.2.2]octanylene group, (vi) D denotes a 1,3-phenylene, cis-1,4-cyclohexylene or trans-1,4-cyclohexylene group, (vii) E denotes a straight-chained $C_{2-4}$-alkylene chain which is substituted by a $C_{1-4}$-alkyl group, by a phenyl group, or by a $C_{1-4}$-alkylsulphonylamino group, or a 1,4-piperidinylene group, (viii) F denotes an alkoxycarbonyl group having a total of 3 to 6 carbon atoms, an $R_7—CO—$, $R_8CO—O—CHR_9—O—CO—$, phosphono or. O-ethyl-phosphono group;

wherein:

X denotes a carbimino group substituted by a cyano group at the nitrogen atom, or a carbonyl or sulphonyl group, Y denotes a $CH_2CH_2$, $CH_2CH_2CH_2$ or $CH=CH$ group optionally substituted by $R_c$ or by $R_c$ and $R_d$, an $N=CH$ group optionally substituted by $R_c$, a $CH_2CO$ or $COCH_2$ group, a 1,2-phenylene or 1,2-cyclohexylene group, wherein $R_c$ denotes a hydrogen atom or a methyl, trifluoromethyl or phenyl group and $R_d$ denotes a hydrogen atom or a methyl group, $R_a$ denotes a group of the formula

A—B—C—

(wherein A denotes an amidino group optionally substituted by an $R_1—CO—O—(R_2CR_3)—O—CO—$ group, wherein $R_1$ denotes a methyl group, $R_2$ denotes a hydrogen atom or a methyl group and $R_3$ denotes a hydrogen atom, or A denotes an aminomethyl group or, if A is bound to a nitrogen atom of groups B or C, A may also denote a hydrogen atom or a methyl group;

B denotes a bond, a 1,4-azacycloheptylene group, a 1,4-piperidinylene group optionally substituted by 1 to 4 methyl groups and which may additionally be substituted in the 4-position by a cyano or aminocarbonyl group, or a 1,4-piperazinylene group, wherein a nitrogen atom of the above mentioned groups is linked to the group A, or A and B together denote a 2-amino-ethoxy or 4-quinuclidinyl group; and C denotes a $CH_2CH_2$ group, a 1,4-phenylene, 1,4-cyclohexylene or 1,4-bicyclo[2.2.2]octanylene group, or if B is a bond, C may also represent a 1,4-piperidinylene group which is bound to the group A via a nitrogen atom, or a 1,2,3,4-tetrahydro-2,6-napthalene group which is bound in the 2-position to the group A, or, if B is a 1,4-piperazinylene group, C may also represent a $—COCH_2—$ group linked via the carbonyl group to the 1,4-piperazinylene B group);

$R_b$ denotes a group of the formula

F—E—D—

(wherein D denotes a straight-chained $C_{1-4}$-alkylene group, a 1,3-phenylene, or a 1,4-cyclohexylene group or a 1,4-phenylene group optionally substituted by a fluorine atom, or by a methyl, trifluoromethyl or cyano group, or D may denote a 2,6-naphthylene or 1,2,3,4-tetrahydro-2,6-naphthylene group, or if E is a 1,4-piperidinylene group, D may also represent a $—COCH_2—$ group linked via the carbonyl group to the 1,4-piperidinylene group of group E;

E denotes a bond, a $CH=CH$ group, a straight-chained $C_{2-4}$-alkylene group optionally substituted by a $C_{1-4}$-alkyl group, by a phenyl group or by a $C_{1-4}$- alkylsulphonylamino group, or E may denote a —O—CH$_2$— group, in which the oxygen atom is attached to the group D, or if D is a —COCH$_2$— group, E may also represent a 1,4-piperidinylene group, wherein the nitrogen atom is linked to the carbonyl group of the —COCH$_2$— group of group D; and F denotes a carbonyl group which is substituted by a hydroxy group, by a C$_{1-5}$-alkoxy group or by an R$_7$O— group, wherein
R$_7$ denotes a cyclopentyl, cyclohexyl, cyclohexylmethyl or 5-indanyl group,
or F denotes an R$_8$CO—O—CHR$_9$—O—CO—, phosphono or O-ethyl-phosphono group, wherein
R$_8$ denotes a tert.butyl, ethoxy or cyclohexyloxy group and
R$_8$ denotes a hydrogen atom or a methyl group,
and the shortest distance between the group F and the furthest removed nitrogen atom of the group A—B—C— amounts to at least 11 bonds);
the tautomers thereof, the stereoisomers thereof and the salts thereof.

The following are examples of particularly preferred cyclic urea derivatives of general formula I:
(a) 2-(4-amidinophenyl)-4-[4-(2-carboxy-1-propyl)phenyl]-5-methyl-4H-1,2,4-triazol-3-one,
(b) 4-[4-(2-carboxyethyl)phenyl]-5-methyl-2-[2-(4-piperidinyl)ethyl]-4H-1,2,4-triazol-3-one,
(c) 1-[4-(2-carboxyethyl)phenyl]-3-[2-(4-piperidinyl)ethyl]-imidazolidin-2-one,
(d) 4-[4-(2-carboxy-1-pentyl)phenyl]-5-methyl-2-[2-(4-piperidinyl)ethyl]-4H-1,2,4-triazol-3-one,
(e) 1-(4-amidinophenyl)-3-[4-[2-(n-butylsulfonylamino)-2-carboxy-ethyl]phenyl]-imidazolidin-2-one,
(f) 2-(4-amidinophenyl)-4-[trans-4-(2-carboxyethyl)cyclohexyl]-4H-1,2,4-triazol-3-one,
(g) 2-(4-amidinophenyl)-4-[4-[2-(cyclohexyloxycarbonyl)-ethyl]phenyl]-5-methyl-4H-1,2,4-triazol-3-one,
(h) 2-(4-amidinophenyl)-4-[trans-4-(2-carboxyethyl)cyclohexyl]-5-methyl-4H-1,2,4-triazol-3-one,
(i) 1-(4-amidinophenyl)-3-[trans-4-(2-carboxyethyl)cyclohexyl]-imidazolidin-2-one,
(j) 1-(4-amidinophenyl)-3-[trans-4-(2-carboxyethyl)cyclohexyl]-imidazolidin-2,4-dione,
(k) 1-(4-amidinophenyl)-3-[trans-4-[2-(methoxycarbonyl)-ethyl)cyclohexyl]-imidazolidin-2-one,
(l) 1-(trans-4-carboxycyclohexyl)-3-[4-(4-cyano-4-piperidinyl)phenyl]-imidazolidin-2-one,
(m) 1-[4-(4-aminocarbonyl-4-piperidinyl)phenyl]-3-(trans-4-carboxycyclohexyl)-imidazolidin-2-one,
(n) 1-[4-[2-(ethoxycarbonyl)ethyl]phenyl]-3-[2-(4-piperidinyl)ethyl]-imidazolidin-2-one,
(o) 1-(trans-4-carboxycyclohexyl)-3-[4-(4-piperidinyl)-phenyl]-imidazolidin-2-one,
(p) 1-[trans-4-(2-carboxyethyl)cyclohexyl]-3-[2-(4-piperidinyl)ethyl]-imidazolidin-2-one,
(q) 1-[4-(2-carboxyethyl)phenyl]-3-[2-(4-quinuclidinyl)-ethyl)-imidazolidin-2-one,
(r) 1-(2-(4-quinuclidinyl)ethyl)-3-(4-[2-(ethoxycarbonyl)-ethyl]phenyl]-imidazolidin-2-one,
(s) 1-[trans-4-(5-indanyloxycarbonyl)cyclohexyl]-3-[4-(4-piperidinyl)phenyl]-imidazolidin-2-one,
(t) 1-[trans-4-[[1-(cyclohexyloxycarbonyloxy)ethyl]oxycarbonyl]cyclohexyl]-3-[4-(4-piperidinyl)phenyl]-imidazolidin-2-one,
(u) 1-[trans-4-(ethoxycarbonyl)cyclohexyl]-3-[4-(4-piperidinyl)phenyl]-imidazolidin-2-one,
(v) 1-[trans-4-[2-(ethoxycarbonyl)ethyl]cyclohexyl]-3-[2-(4-piperidinyl)ethyl]-imidazolidin-2-one,
(w) 1-(2-aminomethyl-1,2,3,4-tetrahydro-6-naphthyl)-3-(trans-4-carboxycyclohexyl)-imidazolidin-2-one,
(x) 1-[trans-4-[(carboxymethyl)oxy]cyclohexyl]-3-[2-(4-piperidinyl)ethyl]-imidazolidin-2-one,
(y) 1-[4-(2-carboxyethenyl)-2-fluoro-phenyl]-3-[2-(4-piperidinyl)ethyl]-imidazolidin-2-one,
(z) 1-(trans-4-carboxycyclohexyl)-3-[4-(4-piperidinyl)cyclohexyl]-imidazolidin-2-one,
(aa) 1-(trans-4-carboxycyclohexyl)-3-[4-(4-quinuclidinyl)-phenyl]-imidazolidin-2-one,
(bb) 1-(trans-4-caboxycyclohexyl)-3-[4-(4-methyl-4-piperidinyl)phenyl]-imidazolidin-2-one,
(cc) 1-[4-(4-quinuclidinyl)phenyl]-3-[trans-4-(ethoxycarbonyl)cyclohexyl]-imidazolidin-2-one,
(dd) 1-[trans-4-(ethoxycarbonyl)cyclohexyl]-3-[4-(4-methyl-4-piperidinyl)phenyl]-imidazolidin-2-one,
(ee) 1-[4-(2-carboxyethenyl)phenyl]-3-[2-(4-piperidinyl)-ethyl]-imidazolidin-2-one,
(ff) 1-[trans-4-(ethoxycarbonyl)cyclohexyl]-3-[4-(4-piperidinyl)phenyl]-3H-imidazol-2-one,
(gg) 1-[4-aminomethyl]-bicyclo[2.2.2]octan-1-yl]-3-[4-(2-carboxyethyl)phenyl]-imidazolidin-2-one,
(hh) 1-[4-(2-carboxy-1-phenyl-ethyl)phenyl]-3-[2-(4-piperidinyl)ethyl]-imidazolidin-2-one,
(ii) 1-(2-carboxy-1,2,3,4-tetrahydro-6-naphthyl)-3-[2-(4-piperidinyl)ethyl]-imidazolidin-2-one and
(jj) 1-(trans-4-carboxycyclohexyl)-3-[4-[(2-aminoethyl)oxy]-phenyl]imidazolidin-2-one, the stereoisomers thereof and the salts thereof.

The new compounds may be prepared by the following processes, for example:

a) in order to prepare compounds of general formula I wherein A is as hereinbefore defined and F denotes a carboxy group or F has the meanings given hereinbefore with the exception of the carboxy group and A denotes a C$_{1-5}$-aminoalkyl group, an amino, amidino or guanidino group, wherein at one of the nitrogen atoms in each of the above mentioned groups one or two hydrogen atoms may each be replaced by an alkyl group, or, if A is bound to a nitrogen atom of groups B or C which is not part of a lactam group, A represents a hydrogen atom:
converting a compound of general formula

(II)

wherein
R$_a$, R$_b$, X and Y are as hereinbefore defined, with the proviso that one of the groups R$_a$ to R$_d$ denotes an F'—E—D— group and one other of the groups R$_a$ to R$_d$ denotes an A—B—C— group or one of the groups R$_a$ to R$_d$ denotes an F—E—D— group and one other of the groups R$_a$ to R$_d$ denotes an A'—B—C— group or one of the groups R$_a$ to R$_d$ denotes an F'—E—D— group and one other of the groups denotes an A'—B—C— group, wherein
A to F are as hereinbefore defined,
A' denotes a group which may be converted by hydrolysis, treatment with acid, thermolysis or hydrogenolysis into an aminoalkyl, amino, amidino or guanidino group, whilst at one of the nitrogen atoms in each of the above mentioned groups, one or two hydrogen atoms may each be replaced by an alkyl group, or, if A' is bound to a nitrogen atom of groups B or C which is not part of a lactam group, A' may denote a group which may be replaced by a hydrogen atom by hydrolysis, treatment with acid, thermolysis or hydrogenolysis and F' denotes a group which may be converted into a carboxy group by hydrolysis, treatment with acid, thermolysis or hydrogenolysis, into a compound of general formula I wherein A is as hereinbefore defined and F denotes a carboxy group or F has the meanings given hereinbefore with the exception of the carboxy group and A denotes an aminoalkyl group having 1 to 5 carbon atoms, an amino, amidino or guanidino group, in which at one of the nitrogen atoms in each of the above mentioned groups, one or two hydrogen atoms may each be replaced by an alkyl group, or, if A is bound to a nitrogen atom of groups B or C which is not part of a lactam group, A may also represent a hydrogen atom.

For example, functional derivatives of the carboxyl group such as unsubstituted or substituted amides, esters, thioesters, trimethylsilylesters, orthoesters, iminoesters, amidines or anhydrides, or a nitrile group, may be converted by hydrolysis into a carboxyl group; esters with tertiary alcohols, e.g. tert.butylesters, may be converted by treatment with an acid or thermolysis into a carboxyl group; and esters with aralkanols, e.g. benzylesters, may be converted by hydrogenolysis into a carboxy group, and by hydrolysis imino groups which are substituted by a protecting group such as a formyl, acetyl, trifluoroacetyl, ethoxycarbonyl or methoxycarbonyl group, or by treatment with an acid or thermolysis imino groups which are substituted by a protecting group such as a tert.butyloxycarbonyl group, or by hydrogenolysis imino groups which are substituted by a protecting group such as a benzyloxycarbonyl, benzyl, methoxybenzyl or 2,4-dimethoxybenzyl group, are converted into the corresponding NH compound.

The hydrolysis is appropriately carried out either in the presence of an acid such as hydrochloric acid, sulphuric acid, phosphoric acid, acetic acid, trichloroacetic acid or trifluoroacetic acid, or mixtures thereof, or in the presence of a base such as lithium hydroxide, sodium hydroxide or potassium hydroxide, in a suitable solvent such as water, water/methanol, water/ethanol, water/isopropanol, methanol, ethanol, water/tetrahydrofuran or water/dioxane, at temperatures between −10° C. and 120° C., e.g. at temperatures between ambient temperature and the boiling temperature of the reaction mixture.

If F' in a compound of formula II represents a cyano or aminocarbonyl group, these groups may also be converted into a carboxyl group with a nitrite, e.g. sodium nitrite, in the presence of an acid such as sulphuric acid, which may appropriately be used as the solvent at the same time, at temperatures between 0° and 50° C.

If, in a compound according to Formula II, A' contains or denotes F', for example the tert.butyloxycarbonyl group, the tert.butyl group may also be cleaved by treatment with an acid such as trifluoroacetic acid, formic acid, p-toluenesulphonic acid, sulphuric acid, hydrochloric acid, phosphoric acid or polyphosphoric acid, optionally in an inert solvent such as lmethylene chloride, chloroform, benzene, toluene, diethylether, tetrahydrofuran or dioxane, preferably at temperatures between −10° and 120° C., e.g. at temperatures between 0° and 60° C., or it may also be cleaved thermolytically, optionally in an inert solvent such as methylene chloride, chloroform, benzene, toluene, tetrahydrofuran or dioxane and preferably in the presence of a catalytic amount of an acid such as p-toluenesulphonic acid, sulphuric acid, phosphoric acid or polyphosphoric acid, preferably at the boiling temperature of the solvent used, e.g.

at temperatures between 40° and 120° C., whereby an N-carboxy-imino compound which may be formed in the reaction mixture may be simultaneously decarboxylated.

If F' in a compound of formula II represents, for example, a benzyloxycarbonyl group, or if A' contains it, the benzyl group may also be hydrogenolytically cleaved in the presence of a hydrogenation catalyst such as palladium/charcoal, in a suitable solvent such as methanol, ethanol, ethanol/water, glacial acetic acid, ethyl acetate, dioxane or dimethylformamide, preferably at temperatures between 0° and 80° C., e.g. at ambient temperature, under a hydrogen pressure of 1 to 5 bar, whilst any N-carboxy-imino compound thus obtained in the reaction mixture is simultaneously decarboxylated.

b) In order to prepare compounds of general formula I wherein A represents an H$_2$N—C(=NH)— group in which a nitrogen atom may be substituted by one or two C$_{1-3}$-alkyl groups:

reacting a compound of general formula

(III)

optionally formed in the reaction mixture, wherein R$_a$, R$_b$, X and Y are as hereinbefore defined, with the proviso that one of the groups R$_a$ to R$_d$ represents a group of the formula

(wherein B and C are as hereinbefore defined and Z$_1$ denotes an alkoxy or arylkoxy group such as a methoxy, ethoxy, n-propoxy, isopropoxy or benzyloxy group or an alkylthio or aralkylthio group such as a methylthio, ethylthio, n-propylthio or benzylthio group or an amino group) with an amine of general formula

(IV)

(wherein R$_{12}$ and R$_{13}$, which may be identical or different, represent hydrogen atoms or C$_{1-3}$-alkyl groups) or with the addition salts thereof.

The reaction is expediently carried out in a solvent such as methanol, ethanol, n-propanol, water, methanol/water, tetrahydrofuran or dioxane at temperatures between −10° and 150° C., preferably at temperatures between 0° and 120° C., with a corresponding free amine or with a corresponding acid addition salt such as, for example, the corresponding ammonium carbonates, acetates or chlorides.

A compound of general formula III may be obtained, for example, by reacting a corresponding nitrile with a suitable alcohol such as methanol, ethanol, n-propanol, isopropanol or benzyl alcohol in the presence of an acid such as hydrochloric acid or by reacting a corresponding amide with a trialkyloxonium salt such as triethyloxonium-tetrafluoroborate, in a solvent such as methylene chloride, tetrahydrofuran or dioxane, at temperatures between −10° and 50° C., but preferably at 0° to 30° C., or by reacting a corresponding nitrile with hydrogen sulphide, appropriately in a solvent such as pyridine or dimethylformamide and in the presence of a base such as triethylamine with subsequent alkylation of the resulting thioamide with a suitable alkyl or aralkyl halide, or by reacting a corresponding nitrile with an alkoxide such as sodium methoxide in a solvent such as dioxane or tetrahydrofuran, but preferably in the alcohol in question. During the reactions with an alcohol, any ester group present may be transesterified at the same time.

c) In order to prepare 4H-1,2,4-triazol-3-ones of general formula I:
cyclising a compound of general formula $$(R_{14}CZ_2)=N-NR_{15}-CO-HN-R_{16} \quad (V)$$

wherein

R$_{14}$ has the meanings given for R$_c$ or R$_d$ hereinbefore, one of the groups R$_{15}$ or R$_{16}$ has the meanings given for R$_a$ hereinbefore and the other group R$_{15}$ or R$_{16}$ has the meanings given for R$_b$ hereinbefore and Z$_2$ denotes. a nucleophilic leaving group such as a halogen atom, a hydroxy, alkoxy, alkylsulphenyl, amino, alkylamino or dialklylamino group, e.g. a chlorine, bromine or iodine atom or a methoxy, ethoxy or methylsulphenyl group.

The reaction is optionally carried out in a solvent such as toluene, xylene, decalin, dioxane, dimethylformamide, methylenechloride, methanol, ethanol, isopropanol, pyridine, acetic acid or trifluoroacetic acid, at temperatures between 20° and 250° C., optionally in the presence of a base or an acid such as trifluoroacetic acid or a dehydrating agent such as phosphorusoxychloride, phosphoruspentachloride or N,N'-dicyclohexylcarbodiimide. However, the reaction is preferably carried out without a solvent.

If Z$_2$ denotes a halogen atom, the reaction is optionally carried out in one of the above mentioned solvents, preferably in the presence of a base such as potassium carbonate, sodium hydride, potassium tert.butoxide or triethylamine, at temperatures between 20° and 60° C., or if Z$_2$ denotes a hydroxy, alkoxy, alkylsulphenyl, amino, alkylamino or dialkylamino group, the reaction is optionally carried out in the presence of an acid such as trifluoroacetic acid, which may simultaneously be used as solvent, at temperatures between 20° and 120° C., but preferably without a solvent at temperatures between 100° and 220° C.

d) In order to prepare compounds of general formula I wherein X denotes a carbonyl group and Y denotes one of the above mentioned ethylene or vinylene groups:
cyclising a compound of general formula $$R_{17}-CO-CHR_{18}-NR_{15}-CO-NHR_{16} \quad (VI)$$

optionally formed in the reaction mixture, wherein one of the groups R$_{15}$ or R$_{16}$ has the meanings given for R$_a$ hereinbefore and the other group R$_{15}$ or R$_{16}$ has the meanings given for R$_b$ hereinbefore, one of the groups R$_{17}$ or R$_{18}$ has the meanings given for R$_c$ hereinbefore, and the other group R$_{17}$ or R$_{18}$ has the meanings given for R$_d$ hereinbefore, optionally with subsequent hydrogenation.

The cyclisation is preferably carried out in a solvent such as methylene chloride, chloroform, acetic acid, benzene, toluene or dioxane, optionally in the presence of an acid such as trifluoroacetic acid, p-toluenesulphonic acid or hydrochloric acid and optionally in the presence of a dehydrating agent such as phosphorusoxychloride, phosphoruspentachloride or N,N'-dicyclohexylcarbodiimide at temperatures between 20° and 150° C., preferably at temperatures between 20° C. and the boiling temperature of the solvent used.

The optional subsequent hydrogenation is preferably carried out with hydrogen in the presence of a catalyst such as palladium/charcoal or platinum in a solvent such as methanol, ethanol, ethylacetate or glacial acetic acid, optionally with the addition of an acid such as hydrochloric acid at temperatures between 0° and 50° C., but preferably at ambient temperature, under a hydrogen pressure of 1 to 7 bar, but preferably 3 to 5 bar.

e) In order to prepare compounds of general formula I wherein X denotes a carbonyl group and Y denotes one of the above mentioned ethylene or vinylene groups:
Reacting a compound of general formula $$R_{15}-NH-CHR_{18}-R_{17}C(OR_{19})_2 \quad (VII)$$

with an isocyanate of general formula $$O=C=N-R_{16} \quad (VIII)$$

wherein one of the groups R$_{15}$ or R$_{16}$ has the meanings given for R$_a$ hereinbefore and the other group R$_{15}$ or R$_{16}$ has the meanings given for R$_b$ hereinbefore, one of the groups R17 or R$_{18}$ has the meanings given for R$_c$ hereinbefore and the other group R$_{17}$ or R$_{18}$ has the meanings given for R$_d$ hereinbefore and R$_{19}$ denotes a C$_{1-4}$alkyl group, optionally with subsequent hydrogenation.

The reaction is optionally carried out in an inert solvent such as dioxane or toluene at temperatures between 20° and 200° C., preferably at temperatures between 20° and 160° C. However, the reaction may also be carried out without a solvent.

An open-chained urea optionally obtained as intermediate product in the reaction of a compound of general formula VII and with an isocyanate of general formula VIII is subsequently, if desired, converted into the desired compound in the presence of an acid such as acetic acid, trifluoroacetic acid, p-toluenesulphonic acid or hydrochloric acid.

The optional subsequent hydrogenation is preferably carried out with hydrogen in the presence of a catalyst such as palladium/charcoal or platinum in a solvent such as methanol, ethanol, ethyl acetate or glacial acetic acid, optionally with the addition of an acid such as hydrochloric acid at temperatures between 0° and 50° C., but preferably at ambient temperature, under a hydrogen pressure of 1 to 7 bar, preferably 3 to 5 bar.

f) In order to prepare compounds of general formula I wherein X denotes a carbonyl group and Y denotes one of the above mentioned COCH$_2$, CH$_2$CO, CONH or NHCO groups:
Cyclising a compound of general formula

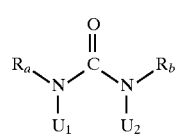

(IX)

wherein R$_a$ and R$_b$ are as hereinbefore defined, one of the groups U$_1$ or U$_2$ represents a hydrogen atom and the other group U$_1$ or U$_2$ represents either a Z$_3$—CO—CH$_2$— group optionally substituted by R$_c$ or R$_d$ or by R$_c$ and R$_d$, wherein Z$_3$ represents a nucleophilic leaving group such as a halogen atom, a hydroxy, alkoxy or sulphonyloxy group, e.g. a chlorine, bromine or iodine atom or a methoxy, ethoxy, isopropyloxy, methanesulphonyloxy or p-toluenesulphonyloxy group, or a Z$_3$'—CONH— group optionally substituted by R$_c$ or R$_d$, wherein Z$_3$' denotes a nucleophilic leaving group such as a halogen atom or an alkoxy group, e.g. a chlorine or bromine atom or a methoxy group, or Z$_3$' together with the hydrogen atom of the NH group denotes a further carbon-nitrogen bond.

The reaction is optionally carried out in a solvent such as ethanol, isopropanol, methylenechloride, dioxane, toluene, dimethylformamide or dimethylsulphoxide, optionally in the presence of a base such as pyridine, triethylamine, sodium hydride or potassium tert.butoxide and optionally in the presence of a dehydrating agent such as N,N'-dicyclohexylcarbodiimide at temperatures between 20° and 200° C. However, the reaction may also be carried out without a solvent.

If Z$_3$ or Z$_3$' represents a nucleophilic leaving group such as a halogen atom or a sulphoneester group, the reaction is preferably carried out in the presence of a base such as potassium carbonate, sodium hydride, potassium tert.butoxide, pyridine or triethylamine at temperatures between 20° and 60° C., if Z$_3$ or Z$_3$' denotes an alkoxy group, the reaction is preferably carried out without a solvent at temperatures between 50° and 250° C., or if Z$_3$ denotes a hydroxy group, the reaction is preferably carried out in the presence of a dehydrating agent such as triphenylphosphine/carbon tetrachloride, N,N'-dicyclohexylcarbodiimide or N,N'-carbonyldiimidazole.

g) In order to prepare compounds of general formula I wherein A denotes an amino, aminoalkyl, amidino or guanidino group substituted by an alkoxycarbonyl group, by a benzyloxycarbonyl group or by an R$_1$—CO—O(R$_2$CR$_3$)—O—CO— group, or A denotes an R$_1$—CO—O—(R$_2$CR$_3$)—O—CO— group:

Reacting a compound of general formula

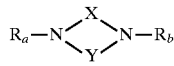

(X)

(wherein R$_a$, R$_b$, X and Y are as hereinbefore defined, with the proviso that one of the groups R$_a$ to R$_d$ denotes an A"—B—C— group wherein B and C are as hereinbefore defined and A" denotes an H$_2$N—C$_{1-5}$-alkyl, H$_2$N—C(=NH)— or H$_2$N—C(=NH)—NH— or H$_2$N group or a hydrogen atom)

with a compound of general formula

Z$_4$—R$_{20}$  (XI)

wherein R$_{20}$ denotes an alkoxycarbonyl group having a total of 2 to 5 carbon atoms, an R$_1$—CO—O—(R$_2$CR$_3$)—O—CO— or benzyloxycarbonyl group and Z$_4$ denotes a nucleophilic leaving group such as a halogen atom, an aryloxy, arylthio, alkoxycarbonyloxy, aralkoxycarbonyloxy or N-imidazolyl group, e.g. a chlorine or bromine atom or a 4-nitrophenoxygroup.

The acylation is appropriately carried out in a solvent such as tetrahydrofuran, methylenechloride, chloroform, dimethylformamide, water or mixtures of these solvents, optionally in the presence of a base such as sodium carbonate, potassium carbonate or sodium hydroxide solution, or in the presence of a tertiary organic base such as triethylamine, N-ethyl-diisopropylamine, N-methyl-morpholine or pyridine, which may simultaneously be used as solvent, at temperatures between −30° and 100° C., but preferably at temperatures between −10° and 60° C.

h) In order to prepare compounds of general formula I wherein F denotes a carbonyl group substituted by a C$_{1-6}$-alkoxy group, by a phenylalkoxy group or by an R$_7$O— group:

Reacting a compound of general formula

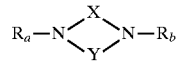

(XII)

(wherein R$_a$, R$_b$, X and Y are as hereinbefore defined, with the proviso that one of the groups R$_a$ to R$_d$ represents an F"—E—D— group wherein E and D are as hereinbefore defined and F" denotes a carboxy or alkoxycarbonyl group)

with an alcohol of general formula

HO—R$_{21}$  (XIII)

wherein R$_{21}$ has the meanings given for R$_7$ hereinbefore or represents a C$_{1-6}$-alkyl group or a phenylalkyl group.

The reaction of a carboxy compound is optionally carried out in a solvent or mixture of solvents such as methylene chloride, dimethylformamide, benzene, toluene, chlorobenzene, tetrahydrofuran, benzene/tetrahydrofuran or dioxane or, particularly advantageously, in a corresponding alcohol of general formula XIII, optionally in the presence of an acid such as hydrochloric acid or in the presence of a dehydrating agent, e.g. in the presence of isobutyl chloroformate, thionylchloride, trimethylchlorosilane, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide or 1-hydroxybenzotriazole and optionally also in the presence of 4-dimethylamino-pyridine, N,N'-carbonyldiimidazole or triphenylphosphine/carbon tetrachloride, conveniently at temperatures between 0° and 150° C., preferably at temperatures between 0° and 80° C.

The reaction of a corresponding alkoxycarbonyl compound with an alcohol of general formula XIII is preferably carried out in a suitable alcohol as solvent, optionally in the presence of another solvent such as methylene chloride or ether, preferably in the presence of an acid such as hydrochloric acid, at temperatures between 0° and 150° C., preferably at temperatures between 50° and 100° C.

i) In order to prepare compounds of general formula I wherein A denotes an H$_2$N—CH$_2$—V— group, where V denotes a bond or a straight-chained or branched C$_{1-4}$-alkylene group:

Reduction of a compound of general formula

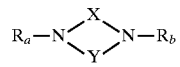

(XIV)

wherein R$_a$, R$_b$, X and Y are as hereinbefore defined, with the proviso that one of the groups R$_a$ to R$_d$ denotes an NC—V—B—C— group, wherein B and C are as hereinbefore defined and V denotes a bond or a straight-chained or branched C$_{1-4}$-alkylene group.

The reduction is preferably carried out in a suitable solvent such as methanol, methanol/water, methanol/water/ammonia, ethanol, ether, tetrahydrofuran, dioxane or dimethylformamide, optionally with the addition of an acid such as hydrochloric acid, in the presence of catalytically activated hydrogen, e.g. hydrogen in the presence of Raney-Nickel, platinum or palladium/charcoal, or in the presence of a metal hydride such as sodium borohydride, lithium borohydride or lithium aluminium hydride, at temperatures between 0° and 100° C., preferably at temperatures between 20° and 80° C.

j) In order to prepare compounds of general formula I wherein A denotes an aminoalkyl group in which the amino group is not bound to a quaternary carbon atom, or A denotes an amino group which is bound to a CH or CH$_2$ group of the group B or C:
Reduction of a compound of general formula

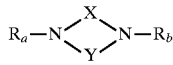 (XV)

wherein R$_a$, R$_b$, X and Y are as hereinbefore defined, with the proviso that one of the groups R$_a$ to R$_d$ denotes an A—B—C— group wherein
A, B and C are as hereinbefore defined, with the proviso that an H$_2$N—CH or H$_2$N—CH$_2$ group present in group A, in group A and B together, or in group A and C together, is replaced by an HO—N=C< or HO—N=CH— group.

The reduction is preferably carried out in a suitable solvent such as methanol, methanol/water, methanol/water/ammonia, ethanol, ether, tetrahydrofuran, dioxane or dimethylformamide, optionally with the addition of an acid such as hydrochloric acid in the presence of catalytically activated hydrogen, e.g. hydrogen in the presence of Raney-nickel, platinum or palladium/charcoal, at temperatures between 0° and 100° C., preferably at temperatures between 0° and 100° C.

k) In order to prepare compounds of general formula I wherein X denotes a carbimino group substituted by a cyano group, or a carbonyl, thiocarbonyl or sulphonyl group:
Reacting a compound of general formula R$_a$—NH—Y'—NH—R$_b$ (XVI)

(wherein R$_a$ and R$_b$ are as hereinbefore defined and
Y' represents a straight-chained C$_{2-3}$-alkylene group optionally substituted by R$_c$ or R$_d$ or by R$_c$ and R$_d$, whilst a methylene group in such an ethylene group may additionally be substituted by a carbonyl group, or
Y' denotes a CO—NH, NH—CO, CH=N or N=CH group optionally substituted by R$_c$ or R$_d$) with a compound of general formula

Z$_5$—X'—Z$_6$ (XVII)

wherein
X' denotes a carbimino group substituted by a cyano group, or
X' denotes a carbonyl, thiocarbonyl or sulphonyl group,
Z$_5$ and Z$_6$, which may be identical or different, represent nucleophilic leaving groups such as halogen atoms, alkoxy or aryloxy groups, e.g. a chlorine atom or a methoxy, ethoxy, phenyloxy or N-imidazolyl group.

The reaction is preferably carried out in a solvent such as methylene chloride, chloroform, toluene or dioxane, optionally in the presence of a base such as sodium hydride, triethylamine or pyridine, at temperatures between 0° and 100° C., preferably at temperatures between 20° and 60° C.

l) In order to prepare compounds of general formula I wherein X denotes a carbimino group substituted by a cyano group, or X denotes a carbonyl or sulphonyl group and Y represents a straight-chained C$_{2-3}$-alkylene group optionally substituted by R$_c$ or R$_d$ or by R$_c$ and R$_d$:

Cyclising a compound of general formula

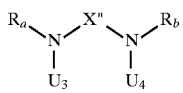 (XVIII)

wherein
R$_a$ and R$_b$ are as hereinbefore defined,
X'' denotes a cyano-substituted carbimino group or a carbonyl or sulphonyl group,
one of the groups U$_3$ or U$_4$ represents a hydrogen atom and
the other group U$_3$ or U$_4$ represents a straight-chained C$_{2-3}$-alkylene group optionally substituted by R$_c$ or R$_d$ or by R$_c$ and R$_d$, and which may also be terminally substituted by a nucleophilic leaving group such as a halogen atom, a hydroxy or sulphonic acid ester group, e.g. by a chlorine, bromine or iodine atom or by a methanesulphonyloxy or p-toluenesulphonyloxy group.

The reaction is preferably carried out in a solvent such as methylene chloride, acetonitrile, tetrahydrofuran, toluene, dimethylformamide or dimethylsulphoxide, optionally in the presence of a base such as sodium hydride, potassium carbonate, potassium tert.butoxide or N-ethyl-diisopropylamine and optionally in the presence of a dehydrating agent such as triphenylphosphine/diethyl azodicarboxylate at temperatures between −20° and 100° C., preferably at temperatures between 0° and 60° C.

m) In order to prepare compounds of general formula I wherein X denotes a carbonyl or sulphonyl group:
Reacting a compound of general formula

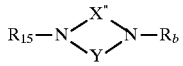 (XIX)

with a compound of general formula

Z$_7$—R$_{16}$ (XX)

wherein Y is as hereinbefore defined
X' denotes a cyano-substituted carbimino group or a carbonyl or sulphonyl group,
one of the groups R$_{15}$ or R$_{16}$ has the meanings given for R$_a$ hereinbefore and
the other group R$_{15}$ or R$_{16}$ has the meanings given for R$_b$ hereinbefore and
Z$_7$ denotes a nucleophilic leaving group such as a halogen atom, a hydroxy or sulphonic acid ester group, e.g, a fluorine, chlorine, bromine or iodine atom or a methanesulphonyloxy or p-toluenesulphonyloxy group.

The reaction is preferably carried out in a solvent such as methylene chloride, acetonitrile, tetrahydrofuran, toluene, pyridine, dimethylformamide, dimethylsulphoxide or N-methyl-pyrrolidone, optionally in the presence of a base such as sodium hydride, potassium carbonate, potassium tert.butoxide, N-ethyl-diisopropylamine or N,N,N',N'-tetramethyl-ethylenediamine and optionally in the presence of a dehydrating agent such as triphenylphosphine/diethyl azodicarboxylate and optionally in the presence of copper powder or a copper salt such as copper(I) iodide as reaction accelerator, at temperatures between −20° and 220° C., but preferably at temperatures between 0° and 60° C. if Z$_7$ is bound to an aliphatic carbon atom, or at temperatures between 60° and 180° C. if Z$_7$ is bound to an aromatic carbon atom, whilst in this case Z$_7$ can only represent a halogen atom.

n) In order to prepare compounds of general formula I wherein A denotes an alkyl group:
Reacting a compound of general formula

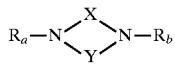 (XXI)

(wherein $R_a$, $R_b$, X and Y are as hereinbefore defined, with the proviso that one of the groups $R_a$ to $R_d$ denotes an A'''—B—C— group wherein B and C are as hereinbefore defined and A''' denotes a hydrogen atom)
with a compound of general formula

 (XXII)

wherein
$R_{22}$ denotes a $C_{1-3}$-alkyl group and $Z_8$ denotes a nucleophilic leaving group such as a halogen atom, e.g. a chlorine, bromine or iodine atom, or a sulphonic acid ester group, e.g. a methanesulphonyloxy or p-toluenesulphonyloxy group, or $Z_8$ together with an adjacent hydrogen atom of the group $R_{22}$ represents an oxygen atom.

The alkylation-with a compound of formula XXII, wherein $Z_8$ denotes a nucleophilic leaving group, is appropriately carried out in a solvent such as methylene chloride, tetrahydrofuran, dioxane, dimethylsulphoxide or dimethylformamide, optionally in the presence of a base such as sodium carbonate, potassium carbonate or sodium hydroxide solution or in the presence of a tertiary organic base such as N-ethyl-diisopropylamine or N-methyl-morpholine, which may simultaneously be used as solvents, at temperatures between −30° and 100° C., but preferably at temperatures between −10° and 80° C.

The reductive alkylation with a carbonyl compound of general formula XXII is carried out in the presence of a complex metal hydride such as sodium borohydride, lithium borohydride or sodium cyanoborohydride, conveniently at a pH of 6 to 7 and at ambient temperature or in the presence of a hydrogenation catalyst, e.g. with hydrogen in the presence of palladium/charcoal, at a hydrogen pressure of 1 to 5 bar. However, methylation is preferably carried out in the presence of formic acid as a reducing agent at elevated temperatures, e.g. at temperatures between 60° and 120° C.

o) In order to prepare compounds of general formula I wherein at least one of the groups B, C, D or E denotes a cyclohexylene group optionally substituted by an alkyl group:
Hydrogenation of a compound of general formula

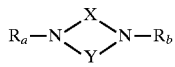 (XXIII)

wherein
$R_a$, $R_b$, X and Y are as hereinbefore defined, with the proviso that at least one of the groups B, C, D or E denotes a phenylene group optionally substituted by an alkyl group.

The catalytic hydrogenation is preferably carried out in a suitable solvent such as methanol, methanol/water, acetic acid, ethyl acetate, ethanol, ether, tetrahydrofuran, dioxane or dimethylformamide, optionally with the addition of an acid such as hydrochloric acid, in the presence of catalytically activated hydrogen, e.g. hydrogen in the presence of Raney-nickel, platinum, rhodium or palladium/charcoal, at temperatures between 0° and 100° C., preferably at temperatures between 20° and 80° C.

p) In order to prepare compounds of general formula I wherein A denotes a cyano group, B denotes a bond and C is an optionally alkyl-substituted 4 to 7 membered cycloalkylene group or B denotes an optionally alkyl-substituted cyclohexylene group:
Reacting a compound of general formula

 (XXIV)

(wherein
$R_a$, $R_b$, X and Y are as hereinbefore defined, with the proviso that one of the groups $R_a$ to $R_d$ denotes an A—B—C— group wherein A together with a CH group in one of the 4 to 7 membered cycloalkyl groups mentioned for B or C hereinbefore denotes a carbonyl group) with a compound of general formula

 (XXV)

wherein $Z_9$ denotes a nucleophilic leaving group such as a p-toluenesulphonyl group.

The reaction is preferably carried out in a solvent such as tetrahydrofuran, ethyleneglycol dimethylether, tert.butanol or ethyleneglycol dimethylether/tert.butanol in the presence of a base such as potassium tert.butoxide at temperatures between −25° and 50° C., preferably at temperatures between −20° C. and ambient temperature.

q) In order to prepare compounds of general formula I wherein F denotes a carbonyl group substituted by a $C_{1-6}$-alkoxy group, or by a phenylalkoxy or $R_8$—CO—O—$CHR_9$—O— group:
Reacting a compound of general formula

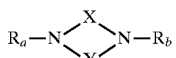 (XXVI)

(wherein
$R_a$, $R_b$, X and Y are as hereinbefore defined, with the proviso that one of the groups $R_a$ to $R_d$ denotes an F'''—E—D— group wherein E and D are as hereinbefore defined and F''' denotes a carboxyl group)
with a compound of general formula

 (XXVII)

wherein
$R_{23}$ denotes a $C_{1-6}$-alkyl group, a phenylalkyl or $R_8$—CO—O—$CHR_9$— group, wherein $R_8$ and $R_9$ are as hereinbefore defined, and
$Z_{10}$ denotes a nucleophilic leaving group such as a halogen atom or a sulphonic acid ester group, e.g. a chlorine or bromine atom or a methanesulphonyloxy or p-toluenesulphonyloxy group.

The reaction is preferably carried out in a solvent such as methylenechloride, tetrahydrofuran, dioxane, dimethylsulphoxide or dimethylformamide, optionally in the presence of a reaction accelerator such as sodium or potassium iodide and preferably in the presence of a base such as sodium carbonate, potassium carbonate or sodium hydroxide solution or in the presence of a tertiary organic base such as N-ethyl-diisopropylamine or N-methyl-morpholine, which may simultaneously also serve as solvent, or optionally in the presence of silver carbonate or silver oxide at temperatures between −30° and 100° C., but preferably at temperatures between −10 and 80° C.

r) In order to prepare compounds of general formula I, in which A together with B is a cyanoalkoxy group with 1 to 10 carbon atoms in the alkoxy moiety, which is bound to a carbon atom of group C via an oxygen atom: reaction of a compound of general formula

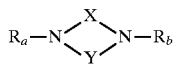 (XXVIII)

(wherein $R_a$, $R_b$, X and Y are as hereinbefore defined, with the proviso that one of groups $R_a$ to $R_d$ is a HO—C group in which the hydroxy group is bound to a carbon atom of the group C) with a compound of general formula

 (XXIX)

in which $R_{24}$ denotes a cyanoalkyl group with 1 to 10 carbon atoms in the alkyl moiety and $Z_{11}$ denotes a nucleophilic leaving group such as a halogen atom, e.g. a chlorine, bromine or iodine atom, or a sulphonate group, e.g. a methanesulphonyloxy or p-toluenesulphonyloxy group.

The reaction is appropriately carried out in a solvent such as methylene chloride, tetrahydrofuran, dioxane, dimethylsulphoxide or dimethylformamide preferably in the presence of a base such as sodium carbonate, potassium carbonate or sodium hydroxide solution or in the presence of a tertiary organic base such as N-ethyl-diisopropylamine or N-methyl-morpholine, which may also serve simultaneously as the solvent, at temperatures between −30° and 100° C., preferably however at temperatures between −10° and 80° C.

If according to the invention a compound of general formula I is obtained which contains a cyano group, this may be converted into an aminocarbonyl or carboxy group by treating with an aqueous acid or base, a compound of general formula I, which contains a double bond between two carbon atoms, may be converted to a corresponding saturated compound by reduction. The subsequent conversion of a cyano group into an aminocarbonyl group is preferably carried out in sulphuric acid in the presence of water or with sodium carbonate or potassium carbonate in the presence of aqueous hydrogen peroxide solution, optionally using a solvent such as dimethylsulphoxide, but preferably in 85% sulphuric acid at ambient temperature.

The subsequent conversion of a cyano group into a carboxy group is conveniently carried out with aqueous sulphuric acid or sodium or potassium hydroxide solution at elevated temperatures, but preferably with aqueous sulphuric acid at temperatures between 80° C. and the boiling temperature of the reaction mixture.

The subsequent reduction of a carbon-carbon double bond is preferably effected by catalytic hydrogenation in a suitable solvent such as methanol, methanol/water, acetic acid, ethyl acetate, ethanol, ether, tetrahydrofuran, dioxane or dimethylformamide, optionally with the addition of an acid such as hydrochloric acid, in the presence of catalytically activated hydrogen, e.g. hydrogen in the presence of Raney-nickel, platinum, rhodium or palladium/charcoal, or in the presence of a hydrogen donor such as 1,3-cyclohexadiene or ammonium formate in the presence of a catalyst such as palladium/charcoal, platinum oxide or Raney-nickel in a solvent such as methanol, ethanol, water, dioxane, acetic acid or ethyl acetate, at temperatures between 0° and 100° C., preferably at temperatures between 20° and 80° C.

In the reaction described hereinbefore, any reactive groups present such as hydroxy, carboxy, phosphono, O-alkylphosphono, amino, alkylamino, imino or amidino groups may optionally be protected during the reaction by means of conventional protecting groups which are cleaved again after the reaction.

For example, the protective group for a hydroxy group may be a trimethylsilyl, acetyl, benzoyl, tert.butyl, trityl, benzyl or tetrahydropyranyl group, the protecting group for a carboxyl group may be a trimethylsilyl, methyl, ethyl, tert.butyl, benzyl or tetrahydropyranyl group, the protecting groups for a phosphono group may be an alkyl group such as methyl, ethyl, isopropyl or n-butyl group or a phenyl or benzyl group, the protecting group for an optionally alkyl-substituted amidino group may be a benzyloxycarbonyl group, the protecting group for an amino, alkylamino or imino group may be a formyl, acetyl, trifluoroacetyl, ethoxycarbonyl, tert.butoxycarbonyl, benzyloxycarbonyl, benzyl, methoxybenzyl or 2,4-dimethoxybenzyl group and for the amino group a phthalyl group may also be considered, and the protecting group for the nitrogen atom of a 1-aza-bicycloalkyl group, such as the quinuclidinyl group, may be the benzyl group or borane.

The optional subsequent cleaving of a protecting group may, for example, be carried out hydrolytically in an aqueous solvent, e.g. in water, isopropanol/water, acetic acid/water, tetrahydrofuran/water or dioxane/water, in the presence of an acid such as trifluoroacetic acid, hydrochloric acid or sulphuric acid, or in the presence of an alkali metal base such as sodium hydroxide or potassium hydroxide, or aprotically, e.g. in the presence of iodotrimethylsilane, at temperatures between 0° and 120° C., preferably at temperatures between 10° and 100° C.

However a benzyl, methoxybenzyl or benzyloxycarbonyl group may be cleaved hydrogenolytically, for example, using hydrogen in the presence of a catalyst such as palladium/charcoal in a solvent such as methanol, ethanol, ethyl acetate or glacial acetic acid, optionally with the addition of an acid such as hydrochloric acid, at temperatures between 0° and 100° C., but preferably at temperatures from 20° to 60° C., under a hydrogen pressure of 1 to 7 bar, preferably 3 to 5 bar. However, a 2,4-dimethoxybenzyl group is preferably cleaved in trifluoroacetic acid in the presence of anisole.

A tert.butyl or tert.butyloxycarbonyl group is preferably cleaved by treating with an acid such as trifluoroacetic acid or hydrochloric acid, or by treating with iodotrimethylsilane, optionally using a solvent such as methylene chloride, dioxane, methanol or ether.

A trifluoroacetyl group is preferably cleaved by treating with an acid such as hydrochloric acid, optionally in the presence of a solvent such as acetic acid, at temperatures between 50° and 120° C., or by treating with sodium hydroxide solution, optionally in the presence of a solvent such as tetrahydrofuran, at temperatures between 0° and 50° C.

A phthalyl group is preferably cleaved in the presence of hydrazine or a primary amine such as methylamine, ethylamine or n-butylamine, in a solvent such as methanol, ethanol, isopropanol, toluene/water or dioxane, at temperatures between 20° and 50° C.

The cleaving of the complex of a 1-aza-bicycloalkyl group such as the quinuclidinyl group, with borane is preferably carried out by treating with an acid such as hydrochloric acid and optionally in the presence of a solvent such as methanol, ethanol, acetic acid or dioxane, at temperatures between 0° C. and the boiling temperature of the reaction mixture. During this reaction, any ester group present may simultaneously be converted into the corresponding carboxy group.

The cleaving of only an alkyl group from an O,O'-dialkylphosphono group is carried out, for example, with sodium iodide in a solvent such as acetone, ethylmethylketone, acetonitrile or dimethylformamide, at temperatures between 40° and 150° C., but preferably at temperatures between 60° and 100° C.

The cleaving of both alkyl groups from an O,O-dialkylphosphono group is carried out, for example, with iodotrimethylsilane, bromotrimethylsilane or chlorotrimethylsilane/sodium iodide in a solvent such as methylene chloride, chloroform or acetonitrile, at temperatures between 0° C. and the boiling temperature of the reaction mixture, but preferably at temperatures between 20° and 60° C.

Furthermore, the compounds of general formula I obtained may be resolved into their enantiomers and/or diastereomers as mentioned hereinbefore. Thus, for example, cis/trans mixtures may be resolved into their cis and trans isomers, and compounds having at least one optically active carbon atom may be resolved into their enantiomers.

Thus, for example, the cis/trans mixtures obtained may be resolved by chromatography into the cis and trans isomers thereof and the compounds of general formula I which occur in racemate form may be separated by methods known per se (cf. Allinger N. L. and Eliel E. L. in "Topics in Stereochemistry", Vol. 6, Wiley Interscience, 1971) into their optical antipodes, and compounds of general formula I having at least 2 asymmetric carbon atoms may be separated on the basis of their physical-chemical differences using known methods, e.g. by chromatography and/or fractional crystallisation, into the diastereomers thereof which, if they occur in recemic form, may subsequently be separated into the enantiomers as mentioned above.

The separation of enantiomers is preferably effected by column separation on chiral phases or by recrystallisation from an optically active solvent or by reacting with optically active substances, especially acids or activated derivatives thereof or alcohols, which form salts or derivatives thereof such as for example, esters or amides with the racemic compound, and separation of the diastereomeric salt mixture or derivative thus obtained, e.g. on the basis of their different solubilities, whilst the free antipodes may be released from the pure diastereomeric salts or derivatives by the action of suitable agents. Particularly common, optically active acids include, for example, the D- and L-forms of tartaric acid and malic acid, mandelic acid, camphorsulphonic acid, glutamic acid, aspartic acid and quinic acid. The optically active alcohol may be (+) or (−)-menthol, for example, and the optically active acyl group in amides may be, for example, (+)- or (−)-menthyloxycarbonyl.

Moreover, the compounds of formula I obtained may be converted into the salts thereof, particularly for pharmaceutical use into the physiologically acceptable salts thereof with inorganic or organic acids. Examples of suitable acids include hydrochloric acid, hydrobromic acid, sulphuric acid, phosphoric acid, fumaric acid, succinic acid, lactic acid, citric acid, tartaric acid or maleic acid.

In addition, the new compounds of formula I thus obtained, if they contained a carboxyl, phosphono, O-alkylphosphono or 5-tetrazolyl group, may subsequently, if desired, be converted into the addition salts thereof with inorganic or organic bases, more particularly, for pharmaceutical use, into the physiologically acceptable addition salts thereof. Examples of suitable bases include sodium hydroxide, potassium hydroxide, arginine, cyclohexylamine, ethanolamine, diethanolamine and triethanolamine.

The compounds used as starting materials are known from the literature in some cases or may be obtained by methods known from the literature, as described in the Examples.

Thus, for example, in "The Organic Chemistry of Heterocyclic Compounds", Volume 37, by C. Temple, Jr., published by John Wiley & Sons, 1981, Chapters 13, 14 and 19 describe the preparation of corresponding triazole compounds.

In Houben-Weyl, "Methoden der Organischen Chemie", Volume E4, by H. Hagemann, published by Georg Thieme, 1983, there is a description starting on page 368 of the preparation of corresponding cyclic urea compounds. The same volume, from page 355, also describes, for example, the preparation of corresponding open-chained urea compounds which may be required as starting compounds.

Thus, for example, a corresponding cyclic urea derivative is obtained by cyclising a correspondingly substituted urea, which is in turn obtained by reacting a corresponding amine with a suitable isocyanate, or by reacting a correspondingly substituted diamine with a carbonic acid derivative such as phosgene or a corresponding triazalone derivative is obtained by cyclising a corresponding semicarbazide, which is in turn obtained by reacting a corresponding isocyanate with a suitable hydrazide.

In the resulting cyclic urea derivatives, a carbonyl group may subsequently, if desired, be converted into a corresponding thiocarbonyl or-carbimino group using known methods.

In the resulting cyclic starting compounds or in the starting compounds required for the preparation thereof, any ester group present may optionally be converted by hydrolysis into a carboxy group, any carboxy group present may be converted into an ester or amide group, any aminocarbonyl group present may be converted by dehydration into a cyano group, any cyano group present may be converted into an amidino group, any carbonyl group present may be converted into the oxime thereof, any functional group present such as a hydroxy, amino or 5-tetrazolyl group may be converted by alkylation, sulphonylation, acylation or tritylation into the corresponding derivative, any cyano group present may be converted into a tetrazolyl group or any reactive bromine atom present may be converted by means of a metal cyanide into a cyano group.

As already mentioned hereinbefore, the new cyclic urea derivatives of general formula I and the salts thereof, particularly the physiologically acceptable salts thereof, with inorganic or organic acids or bases, have valuable properties. Thus, the new compounds of general formula I wherein A, A together with B, A together with C, or A together with B and C contains a basic group or a group which may optionally be converted in vivo into a basic group, and F denotes a carboxyl, phosphono, O-alkylphosphono or 5-tetrazolyl group or a group which can optionally be converted in vivo into a carboxyl, phosphono, O-alkylphosphono or 5-tetrazolyl group, e.g. a carbonyl group substituted by an alkoxy or cycloalkoxy group, have valuable pharmacological properties, in addition to having an inhibitory effect on inflammation and bone degradation, they have in particular antithrombotic, antiaggregatory and tumour- or metastases-inhibiting effects.

The compounds of general formula I wherein A represents a cyano or cyanoalkyl group are valuable intermediates in the preparation of the corresponding aminoalkyl and amidino compounds of general formula I. Moreover, the compounds of general formula I wherein A denotes a benzyl group optionally substituted in the phenyl moiety by 1 to 2 methoxy groups, or A denotes a formyl, acetyl, trifluoroacetyl, benzyloxycarbonyl or alkoxycarbonyl group, are valuable intermediates for preparing the corresponding imino compounds of general formula I wherein A denotes a hydrogen atom.

Furthermore, compounds of general formula I wherein A together with B, or A together with B and C represent an azabicycloalkyl group complexed by borane at the nitrogen atom or quaternised by a benzyl group optionally substituted by 1 or 2 methoxy groups in the phenyl nucleus, are valuable intermediate products for preparing the corresponding compounds of general formula I which are not complexed at the nitrogen atom and not quaternised.

By way of example, the compounds of general formula I were investigated for their biological effects as follows:
1. Inhibition of Binding of $^3$H-BIBU 52 to Human Thrombocytes A suspension of human thrombocytes in plasma is incubated with $^3$H-BIBU 52 [=(3S,5S)-5-[(4'-amidino-4-biphenylyl)oxymethyl]-3-[(carboxyl)methyl]-2-pyrrolidinone[$^3$-$^3$H-4-biphenylyl]] (see the German Patent application P 42 14 245.8 by the same applicant dated 30.04.1992, internal reference: Case 5/1-93-FL), which replaces the ligand $^{125}$I-fibrinogen known from the literature and various concentrations of the substance to be tested. The free and bound ligand is separated by centrifuging and quantitatively determined by scintillation counting. From the measurements obtained, the inhibition of $^3$H-BIBU 52 binding by the test substance is determined.

In order to do this, donor blood is taken from an anticubital vein and anticoagulated by trisodium citrate (final concentration 13 mM). The blood is centrifuged for 10 minutes at 170×g and the supernatant platelet-rich plasma (PRP) is removed. The remaining blood is vigorously centrifuged once more in order to obtain plasma. The PRP is diluted 1:10 with autologous plasma. 750 µl are incubated with 50 µl of physiological saline solution, 100 µl of test substance solution, 50 µl of $^4$C-sucrose (3,700 Bq) and 50 µl of $^3$H-BIBU 52 (final concentration: 5 nM) at ambient temperature for 20 minutes. In order to measure non-specific binding, instead of the test substance, 5 µl of BIBU 52 are put in (final concentration: 30 µM). The samples are centrifuged for 20 seconds at 10,000×g and the supernatant is drawn off. 100 µl therof are measured in order to determine the free ligand. The pellet is dissolved in 500 µl of 0.2N NaOH, 450 µl are mixed with 2 ml of scintillator and 25 µl of 5N HCl and measured. The residual plasma remaining in the pellet is determined from the $^{14}$C content, the bound ligand from the $^3$H measurement. After subtracting the non-specific binding, the pellet activity is plotted against the concentration of the test substance and the concentration for a 50% inhibition of binding is determined.

2. Antithrombotic effect:

Method

The thrombocyte aggregatrion is measured using the Born and Cross method (J. Physiol. 170: 397 (1964)) in platelet-rich plasma taken from health volunteers. To inhibit coagulation the blood is mixed with 3.14% sodium citrate in a ratio by volume of 1:10.

Collagen-induced agaregation

The pattern of the decrease in optical density of the platelet suspension is photometrically measured and recorded after the addition of the aggregation-triggering substance. The rate of aggregation is concluded from the angle of inclination of the density curve. The point on the curve where there is maximum light transmittance is used to calculate the optical density.

The amount of collagen used is as small as possible but sufficient to produce an irreversible reaction curve. Standard commercial collagen produced by Hormonchemie of Munich is used.

Before the addition of the collagen the plasma is incubated for 10 minutes with the substance at 37° C.

From the measurements obtained an $EC_{50}$ is determined graphically, indicating a 50% change in the optical density in terms of the inhibition of aggregation.

The following table shows the results which were obtained:

| Substance (Example No.) | Fibrinogen-binding test $IC_{50}$[nM] | Inhibition of platelet aggregation $EC_{50}$[nM] |
|---|---|---|
| 1(1) | 0.8 | 30 |
| 1(2) | 1.2 | 70 |
| 1(3) | 64.0 | 270 |
| 1(4) | 280.0 | 500 |
| 1(6) | 18.0 | 100 |
| 1(8) | 760.0 | 1200 |
| 1(21) | 1.0 | 36 |
| 1(39) | 25.0 | 86 |
| 1(44) | — | 380 |
| 1(50) | 65.0 | 170 |
| 2(5) | 3500.0 | 3200 |
| 4 | 94.0 | 130 |
| 4(4) | 2.9 | 30 |
| 4(5) | 4100.0 | 3300 |
| 4(13) | 250.0 | 300 |
| 5(2) | 720.0 | 840 |
| 6(14) | 250.0 | 40 |
| 6(34) | 21000.0 | 350 |
| 6(35) | 5700.0 | 630 |
| 6(37) | 7100.0 | 380 |
| 6(40) | 2500.0 | 240 |
| 15 | 12000.0 | 4300 |
| 17 | 16.0 | 43 |
| 18(2) | — | 110 |
| 24(1) | 150.0 | 940 |
| 24(2) | — | 71 |
| 26 | 26.0 | 84 |
| 30(4) | 200.0 | 490 |

Moreover, the compound of Example 6(14), for example, inhibits the collagen-induced aggregation of thrombocytes in the rhesus monkey ex vivo after the oral administration of 1 mg/kg for up to four hours.

The compounds according to the invention are well tolerated because after intravenous administration of 30 mg/kg of the compounds of Examples 1(1), 1(4), 1(6), 1(39), 17 and 26 to mice, none of the three animals tested died.

In the light of their inhibitory effect on cell-to-cell or cell-to-matrix interactions, the new cyclic urea derivatives of general formula I and the physiologically acceptable addition salts thereof are suitable for treating or preventing diseases in which smaller or greater cell aggregates occur or in which cell-to-matrix interactions play a part, e.g. in treating or preventing venous and arterial thrombosis, cerebrovascular diseases, lung embolism, cardiac infarction, arteriosclerosis, osteoporosis and the metastasis of tumours and the treatment of genetically caused or acquired disorders of cell interactions with one another or with solid structures. They are also suitable for parallel therapy in thrombolysis with fibrinolytics or vascular interventions such as transluminal angioplasty or in the treatment of shock, psoriasis, diabetes and inflammation.

For treating or preventing the diseases mentioned above the dosage is between 0.1 μg and 30 mg/kg of body weight, preferably 1 μg to 15 mg/kg of body weight, given in up to 4 doses per day. For this purpose the compounds of formula I produced according to the invention, optionally in conjunction with other active substances, such as thromboxane receptor antagonists and thromboxane synthesis inhibitors or combinations thereof, serotonin antagonists, α-receptor antagonists, alkylnitrates such as glycerol trinitrate, phosphodiesterase inhibitors, prostacyclin and the analogues thereof, fibrinolytics such as tPA, prourokinase, urokinase, streptokinase, or anticoagulants such as heparin, dermatane sulphate, activated protein C, vitamin K antagonists, hirudine, inhibitors of thrombin or other activated clotting factors, may be incorporated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/ polyethyleneglycol, propyleneglycol, stearylalcohol, carboxymethyl-cellulose or fatty substances such as hard fat or suitable mixtures thereof, into conventional galenic preparations such as plain or coated tablets, capsules, powders, suspensions, solutions, sprays or suppositories.

The Examples which follow are intended to illustrate the invention:

EXAMPLE I

1-Acetyl-2-(4-cyanophenyl)-4-[4-(1-ethoxycarbonyl-2-propyl)-phenyl]-semicarbazide 2.79 g of 1-acetyl-2-(4-cyanophenyl)-hydrazine and 4.13 g of [4-(1-ethoxycarbonyl-2-propyl)phenyl]isocyanate are stirred for 2 hours at 100° C. under nitrogen. Then the mixture is cooled. The product is further reacted in Example 3 without any further purification.

Yield: 6.5 g (94% of theory); $R_f$ value: 0.37 (Silica gel; methylene chloride/ethyl-acetate/cyclohexane=20:1:1)

The following compounds are obtained analogously to Example I:

(1) 1-acetyl-2-(4-cyanophenyl)-4-[4-(2-ethoxycarbonyl-1-propyl)phenyl]-semicarbazide $R_f$ value: 0.32 (Silica gel; methylene chloride/ethyl-acetate=20:1)

(2) 1-acetyl-2-(4-cyanophenyl)-4-[cis-4-[2-(methoxycarbonyl)-ethyl]cyclohexyl]-semicarbazide Melting point: 138°–140° C.; $R_f$ value: 0.54 (Silica gel; methylene chloride/ethyl acetate=4:1)

(3) 1-acetyl-2-(4-cyanophenyl)-4-[trans- 4-[2-(methoxycarbonyl)ethyl]cyclohexyl]-semicarbazide Melting point: 132°–134° C.; $R_f$ value: 0.54 (Silica gel; methylene chloride/ethyl acetate=4:1)

(4) 1-Acetyl-2-(4-cyanophenyl)-4-[3-[2-(methoxycarbonyl)-ethyl]phenyl]-semicarbazide $R_f$ value: 0.55 (Silica gel; methylene chloride/ethyl acetate=9:1)

(5) 1-trifluoroacetyl-2-(4-cyanophenyl)-4-[4-[2-(methoxycarbonyl)ethyl]phenyl]-semicarbazide $R_f$ value: 0.60 (Silica gel; methylene chloride/methanol=20:1)

(6) 1-acetyl-2-(4-cyanophenyl)-4-[4-[2-(methoxy-carbonyl)-ethyl]phenyl]-semicarbazide $R_f$ value: 0.42 (Silica gel; methylene chloride/ethyl acetate=9:1)

(7) 1-benzoyl-2-(4-cyanophenyl)-4-[4-[2-(methoxy-carbonyl)-ethyl]phenyl]-semicarbazide Melting point: 76°–81° C.; $R_f$ value: 0.32 (Silica gel; methylene chloride/ethyl acetate=20:1)

(8) 1-acetyl-4-[4-[2-(methoxycarbonyl)ethyl]phenyl]-semicarbazide

Melting point: 159°–165° C.; $R_f$ value: 0.37 (Silica gel; Methylene chloride/Methanol=9:1)

(9) 2-(4-cyanophenyl)-1-formyl-4-[trans-4-[2-(methoxycarbonyl)ethyl]cyclohexyl]-semicarbazide Melting point: 140°–142° C.; $R_f$ value: 0.57 (Silica gel; methylene chloride/ethyl acetate=4:1)

(10) 1-acetyl-4-[4-[2-(methoxycarbonyl)- 1-pentyl]-phenyl]-semicarbazide

Melting point: 109°–111° C.; Calculated: C 60.88 H 7.51 N 12.53; Found: 60.81 7.51 12.30

(11) 1-acetyl-4-[4-[2-(methoxycarbonyl)-3-methyl-1-butyl]-phenyl]-semicarbazide

(12) 1-acetyl-4-[4-[2-(methoxycarbonyl)-1-butyl]phenyl]-semicarbazide

(13) 1-acetyl-4-[4-[2-(methoxycarbonyl)-1-propyl]-phenyl]-semicarbazide

(14) 1-acetyl-2-(4-cyanophenyl)-4-[4-[2-(methoxy-carbonyl)-1-pentyl]phenyl]-semicarbazide

(15) 1-formyl-4-[4-[2-(methoxycarbonyl)ethyl]phenyl]-semicarbazide

Melting point: 146°–148° C.; $R_f$ value: 0.34 (Silica gel; methylene chloride/methanol=100:5)

(16) 1-formyl-4-[trans-4-(methoxycarbonyl)cyclohexyl]-semicarbazide

Melting point: 183° C.; $R_f$ value: 0.48 (Silica gel; methylene chloride/methanol=5:1)

(17) 1-acetyl-4-[trans-4-(methoxycarbonyl)cyclohexyl]-semicarbazide

Melting point: 191° C.; $R_f$ value: 0.50 (Silica gel; methylene chloride/methanol=5:1)

EXAMPLE II 3-(4-Bromophenyl)-1-[4-(2-carboxyethyl)phenyl]-imidazolidin-2-one 12.7 g of 3-(4-bromophenyl)-1-[4-[2-(ethoxycarbonyl)-ethyl]-phenyl]-imidazolidin-2-one, 300 ml of tetrahydrofuran, 100 ml of water and 23.6 ml of 4N sodium hydroxide solution are stirred overnight at ambient temperature. The precipitate is suction filtered, suspended in 1 litre of water, acidified with concentrated hydrochloric acid and stirred for 2 hours. It is then suction filtered, washed with water and dried at 60° C.

Yield: 7.8 g (66% of theory); Melting point: 244°–246° C.; Calulated: C 55.54 H 4.40 N 7.20 Br 20.53; Found: 55.65 4.48 7.24 20.37

EXAMPLE III 1-(4-Bromophenyl)-3-[4-[2-(ethoxycarbonyl)ethyl]phenyl]-imidaz olidin-2-one To a solution of 13.5 g of N-(4-bromophenyl)-N'-[4-[2-(ethoxycarbonyl)ethyl]phenyl]-N'-(2-hydroxyethyl)-urea in 40 ml of methylene chloride are added 3.7 g of methane sulphonyl chloride and then, whilst cooling in an ice/methanol bath, 3.8 g of triethylamine in 10 ml of methylene chloride are added dropwise. After 1 hour's stirring without cooling, water is added, the phases are separated and the aqueous phase is extracted with methylene chloride. The combined organic phases are washed with water, dried and concentrated by evaporation. The residue is refluxed for 3 hours with 9.3 g of sodium iodide in 250 ml of acetone. The mixture is evaporated to dryness, the residue is dissolved in 100 ml of dimethylformamide and 3.7 g of potassium tert.butoxide in 25 ml of dimethylformamide are added whilst cooling with ice. After 30 minutes' stirring at ambient temperature, the mixture is evaporated down, the residue is distributed between water and methylene chloride and the aqueous phase is extracted with methylene chloride. The combined organic phases are washed with water, dried and concentrated by rotary evaporation. The residue is stirred overnight with ethanol, cooled and the product is suction filtered, washed with ethanol and dried.

Yield: 8.9 g (69% of theory); $R_f$ value: 0.40 (Silica gel; methylene chloride); Calculated: C 57.57 H 5.07 N 6.71 Br 19.15; Found: 57.34 4.99 6.83 19.27

EXAMPLE IV
1-[4-[2-(Methoxycarbonyl)ethyl]phenyl]-imidazolidin-2-one

To 11.3 g of N-(2-chloroethyl)-N'-[4-[2-(methoxycarbonyl)ethyl]-phenyl]-urea in 15 ml of dimethylformamide is added, dropwise without cooling, a solution of 4.5 g of potassium tert.butoxide in 15 ml of dimethylformamide. After 2 hours stirring the reaction mixture is poured onto 600 ml of water. The precipitate is suction filtered, washed with water and dried at 100° C.

Yield: 8.84 g (89% of theory); Melting point: 171°–172° C.; $R_f$ value: 0.46 (Silica gel; methylene chloride/methanol= 20:1)

The following compounds are obtained analogously to Example IV:
(1) 1-[4-[2-(methoxycarbonyl)-1-pentyl]phenyl]-imidazolidin-2-one
(2) 1-[4-(1-trifluoroacetyl-4-piperidinyl)phenyl]-imidazolidin-2-one Melting point: 198°–201° C.; $R_f$ value: 0.51 (Silica gel; ethyl acetate)
(3) 1-[4-(4-cyano-1-trifluoroacetyl-4-piperidinyl)-phenyl]-imidazolidin-2-one $R_f$ value: 0.45 (Silica gel; cyclohexane/ethyl acetate=3:2)
(4) 1-(4-bromo-2-fluoro-phenyl)-imidazolidin-2-one Melting point: 134°–136° C.
(5) 1-(4-bromo-2-trifluoromethyl-phenyl)-imidazolidin-2-one Melting point: 139°–141° C.
(6) 1-(4-bromo-2-methyl-phenyl)-imidazolidin-2-one Melting point: 184°–186° C.
(7) 1-(4-[2-(methoxycarbonyl)ethenyl]phenyl]-imidazolidin-2-one Melting point: 233°–234° C.
(8) 1-[4-[2-(ethoxycarbonyl)-1-phenyl-ethyl]-phenyl]-imidazolidin-2-one Melting point: 167°–169° C.

EXAMPLE V
4-[2-(n-Butylsulfonylamino)-2-(methoxycarbonyl)-ethyl)]-N-(2-hydroxyethyl)-aniline 5.0 g of 4-[2-(n-butylsulfonylamino)-2-(methoxycarbonyl)-ethyl]-aniline in 50 ml of acetonitrile are mixed with 1N hydrochloric acid until a pH of 6–7 is obtained. 1.02 g of glycolaldehyde (dimer) are dissolved in this mixture and 1.13 g of sodium cyanoborohydride are added in batches thereto. After 1 hours' stirring at ambient temperature the mixture is evaporated down and the residue is distributed between ice water and ethyl acetate. The aqueous phase is made alkaline and extracted with ethyl acetate. The combined organic phases are washed with saline solution, dried and evaporated down. The residue is purified by chromatography over a silica gel column with cyclohexane/ethyl acetate (1:1 to 3:7).

Yield: 1.6 g (29% of theory); $R_f$ value: 0.31 (Silica gel; cyclohexane/ethyl acetate=3:7)

The following compound is obtained analogously to Example V:
(1) 1-benzyl-4-[(2-hydroxyethyl)amino]-piperidine $R_f$ value: 0.33 (Silica gel; methylene chloride/methanol/cyclohexane/conc. aqueous ammonia=7:1.5:1.5:0.2)

EXAMPLE VI
1-(1-Hydroxyimino-1,2,3,4-tetrahydronaphthalin-6-yl)-3-[4-[2-(methoxycarbonyl)ethyl]phenyl]-imidazolidin-2-one To a boiling solution of 2.35 g of 1-(1-oxo-1,2,3,4-tetrahydronaphthalin-6-yl)-3-[4-[2-(methoxycarbonyl)-ethyl]phenyl]-imidazolidin-2-one in a mixture of 100 ml of methanol, 50 ml of.dioxane and 1.5 ml of pyridine, are added 460 mg of hydroxylamine-hydrochloride and the mixture is refluxed for 2 hours. After cooling overnight it is suction filtered, washed with methanol, water and methanol again and dried.

Yield: 2.3 g (94% of theory); $R_f$ value: 0.42 (Silica gel; methylene chloride/methanol=95:5) Calculated: C 67.80 H 6.18 N 10.31; Found: 67.70 6.04 10.21

EXAMPLE VII
1-(1-Oxo-1,2,3,4-tetrahydronaphthalin-6-yl)-3-[4-[2-(methoxycarbonyl)ethyl]phenyl]-imidazolidin-2-one To a solution of 3.7 g of triphenylphosphine and 5.5 g of N-(1-oxo-1,2,3,4-tetrahydronaphthalin-6-yl)-N'-(2-hydroxyethyl)-N'-[4-[2-(methoxycarbonyl)ethyl]phenyl]-urea in 40 ml acetonitrile, are added, dropwise at 40°–45° C., 2.84 g of diethyl azodicarboxylate in 10 ml of acetonitrile. After 1.5 hours the mixture is cooled, the product is suction filtered and washed with a little acetone and diethylether.

Yield: 4.27 g (81% of theory); Melting point: 180°–182° C.; Calculated: C 70.39 H 6.16 N 7.14; Found: 70.43 6.13 7.14

The following compound is obtained analogously to Example VII:
(1) 1-[4-[2-(methoxycarbonyl)ethyl]phenyl]-4-methyl-imidazolidin-2-one $R_f$ value: 0.16 (Silica gel; cyclohexane/ethyl acetate=1:1)

EXAMPLE VIII
4-[2-(n-Butylsulfonylamino)-2-(methoxycarbonyl)-ethyl]-aniline 19 g of 4-[2-(n-butylsulfonylamino)-2-(methoxycarbonyl)-ethyl]-nitrobenzene (melting point 102°–104° C.; prepared from β-(4-nitrophenyl)-D,L-alanine-methylester by reacting with n-butylsulfonic acid chloride in the presence of N-ethyl-diisopropylamine) are hydrogenated in 200 ml of ethyl acetate at ambient temperature under a hydrogen pressure of 3.4 bar in the presence of 2 g of palladium on activated charcoal (10% palladium) for 1.5 hours. The catalyst is suction filtered and the filtrate is evaporated down.

Yield: 17.8 g (100% of theory); $R_f$ value: 0.45 (Silica gel; cyclohexane/ethyl acetate=1:1)

The following compounds are obtained analogously to Example VIII:
(1) 4-(4-cyano-1-trifluoroacetyl-4-piperidinyl)-aniline $R_f$ value: 0.28 (Silica gel; cyclohexane/ethyl acetate=2:1)
(2) 4-(1-trifluoroacetyl-4-piperidinyl)-aniline Melting point: 111°–112° C.; R_f value: 0.25 (Silica gel; cyclohexane/ethyl acetate=2:1)

(3) 2-[[4-[2-(methoxycarbonyl)ethyl]phenyl]amino]-aniline

The starting material 2-[[4-[2-(methoxycarbonyl)-ethyl]phenyl]-amino]-nitrobenzene (melting point: 68°–70° C.) is obtained by reacting 2-fluoro-nitrobenzene with methyl 3-(4-aminophenyl)propionate.

R_f value: 0.25 (Silica gel; methylene chloride/ethyl acetate=100:1)

(4) 4-[2-(O,O'-diethylphosphono)ethyl]-aniline

The starting material 4-[2-(O,O'-diethylphosphono)-ethenyl]-nitrobenzene (melting point: 102°–104° C.) is obtained by reacting tetraethyl methanediphosphonate/potassium tert.butoxide with 4-nitrobenzaldehyde.

R_f value: 0.55 (Silica gel; ethyl acetate/ethanol=15:1)

(5) 4-(4-aminophenyl)-quinuclidine

Carried out in 1N hydrochloric acid, isolation of the base.

R_f value: 0.89 (Reversed Phase Silica gel; methanol/5% saline=6:4)

(6) 4-(4-aminophenyl)-4-methyl-1-trifluoroacetyl-piperidine

R_f value: 0.33 (Silica gel; cyclohexane/ethyl acetate=7:3)

(7) ethyl 3-(4-aminophenyl)-3-phenyl-propionate-hydrochloride

Carried out in ethanol in the presence of ethanolic hydrochloric acid. The starting material ethyl 3-(4-nitrophenyl)-3-phenyl-acrylate [R_f value: 0.36 (Silica gel; cyclohexane/methylene chloride=1:1)] is obtained by reaction of 4-nitrobenzophenone with triethyl phosphonoacetate.

R_f value: 0.40 (Reversed Phase Silica gel; methanol/5% saline=6:4)

EXAMPLE IX

4-[4-[2-(Methoxycarbonyl)ethyl]phenyl]-5-methyl-4H-1,2,4-triazol-3-one 8.1 g of 1-acetyl-4-[4-[2-(methoxycarbonyl)ethyl]phenyl]-semicarbazide are heated with 60 ml of 1N sodium hydroxide solution over a steam bath for 1.5 hours. Then the mixture is cooled somewhat, filtered and the filtrate is acidified slightly with citric acid. It is filtered and the filtrate is mixed with concentrated hydrochloric acid. The precipitate is filtered, washed with water and dried. The intermediate product is stirred overnight in methanol with some methanolic hydrochloric acid. The reaction mixture is evaporated down and the residue is triturated with tert.-butyl-methylether, suction filtered and dried.

Yield: 4.98 g (65% of theory); R_f value: 0.40 (Silica gel; toluene/dioxane/ethanol/ethyl acetate=90:10:10:6); Calculated: C 59.76 H 5.79 N 16.08; Found: 59.54 5.86 16.05

The following compounds are obtained analogously to Example IX:

(1) 4-[4-[2-(methoxycarbonyl)-1-pentyl]phenyl]-5-methyl-4H-1,2,4-triazol-3-one

Melting point: 135°–137° C.; Calculated: C 63.35 H 6.98 N 13.85; Found: 63.39 7.04 13.83

(2) 4-[4-[2-(methoxycarbonyl)-3-methyl-1-butyl]phenyl]-5-methyl-4H-1,2,4-triazol-3-one (3) 4-[4-[2-(methoxycarbonyl)-1-butyl]phenyl]-5-methyl-4H-1,2,4-triazol-3-one (4) 4-[4-[2-(methoxycarbonyl)-1-propyl]phenyl]-5-methyl-4H-1,2,4-triazol-3-one (5) 4-[4-[2-(methoxycarbonyl)ethyl]phenyl]-4H-1,2,4-triazol-3-one Melting point: 174°–176° C.; R_f value: 0.57 (Silica gel; toluene/dioxane/ethanol/ethyl acetate=90:10:10:6)

(6) 4-[trans-4-(methoxycarbonyl)cyclohexyl]-4H-1,2,4-triazol-3-one

Melting point: 204°–206° C.; Calculated: C 53.32 H 6.71 N 18.66; Found: 53.29 6.66 18.83

(7) 4-[trans-4-(methoxycarbonyl)cyclohexyl]-5-methyl-4H-1,2,4-triazol-3-one

Melting point: 203°–204° C.; Calculated: C 55.22 H 7.15 N 17.56; Found: 55.14 7.23 17.32

Example X 1-tert.Butyloxycarbonyl-4-[2-(methanesulfonyloxy)ethyl]-piperidine

A solution of 1.3 g of 1-tert.butyloxycarbonyl-4-(2-hydroxyethyl)-piperidine in 30 ml methylene chloride is mixed 710 mg of methanesulfonyl chloride and cooled in an ice bath. 640 mg of triethylamine are slowly added dropwise thereto. After 1 hours' stirring, ice water is added, the mixture is stirred for 15 minutes and then the organic phase is separated off and evaporated down. The residue is stirred with a little diisopropylether and petroleum ether, the product is suction filtered, washed with petroleum ether and dried.

Yield: 1.37 g (80% of theory); Melting point: 81°–84° C.; R_f value: 0.43 (Silica gel; cyclohexane/ethyl acetate=1:1)

The following compounds are obtained analogously to Example X:

(1) 1-tert.butyloxycarbonyl-4-[2-(methanesulfonyloxy)-ethyl]-1-azacycloheptane

The 1-tert.butyloxycarbonyl-4-(2-hydroxyethyl)-1-azacycloheptane used as starting material is obtained starting from ethyl 1-aza-4-cycloheptyl-acetate by reacting with di-tert.butyl pyrocarbonate and subsequent reduction with lithium borohydride.

R_f value: 0.48 (Silica gel; cyclohexane/ethyl acetate=1:1)

(2) 4-[2-(methansulfonyloxy)ethyl]-quinclidine×BH_3

Melting point: 83°–86° C.; R_f value: 0.44 (Silica gel; cyclohexane/ethyl acetate=3:7)

(3) 1-tert.butyloxycarbonyl-3-[2-(methane-sulphonyloxy)-ethyl]pyrrolidine

The starting material, 1-tert.butyloxycarbonyl-3-(2-hydroxyethyl)pyrrolidine [R_f value: 0.30 (Silica gel; cyclohexane/ethyl acetate=1:1)], is obtained by reaction of 3-(2-hydroxymethyl)pyrrolidine with di-tert.butyl pyrocarbonate.

R_f value: 0.36 (Silica gel; cyclohexane/ethyl acetate=1:1)

EXAMPLE XI

N-(1-oxo-1,2,3,4-tetrahydronaphthalin-6-yl)-N'-(2-hydroxyethyl)-N'-[4-[2-(methoxycarbonyl)ethyl]phenyl]-urea To 4.1 g of N-(2-hydroxyethyl)-4-[2-(methoxycarbonyl)ethyl]-aniline in 10 ml of dioxane are added 3.9 g of (1-oxo-1,2,3,4-tetrahydronaphthalin-6-yl)-isocyanate in 10 ml of dioxane and the mixture is stirred overnight. The reaction mixture is evaporated down, the residue is taken up in ethyl acetate and washed with dilute citric acid solution and saline solution. The organic phase is evaporated down and purified by chromatography over a silica gel column using cyclohexane/ethyl acetate (3:7).

Yield: 5.6 g (73% of theory); R_f value: 0.21 (Silica gel; cyclohexane/ethyl acetate=3:7)

The following compounds are obtained analogously to Example XI:

(1) N-(2,2-diethoxyethyl)-N-(1,4-dioxaspiro[4.5]decan-8-yl)-N'-[4-[2-(methoxycarbonyl)ethyl]phenyl]-urea R_f value: 0.34 (Silica gel; cyclohexane/ethyl acetate=1:1)

(2) N-(4-cyanophenyl)-N'-(2-hydroxyethyl)-N'-[4-[2-(methoxycarbonyl)ethyl]phenyl]-urea Melting point: 98°–101° C.

(3) N-(4-bromophenyl)-N'-[4-[2-(ethoxycarbonyl)ethyl]phenyl]-N'-(2-hydroxyethyl)-urea R_f value: 0.38 (Silica gel; cyclohexane/ethyl acetate=6:4)

(4) N-(4-cyanophenyl)-N-(methoxycarbonylmethyl)-N'-[trans-4-[2-(methoxycarbonyl)ethyl]cyclohexyl]-urea Melting point: 108°–110° C.; $R_f$ value: 0.62 (Silica gel; methylene chloride/ethyl acetate=4:1)

(5) N-(2-chloroethyl)-N'-[4-[2-(methoxycarbonyl)ethyl]phenyl]-urea

Melting point: 124°–125° C.

(6) N-(2-chloroethyl)-N'-[4-[2-(methoxycarbonyl)-1-pentyl]-phenyl]-urea (7) N-(1-benzyl-4-piperidinyl)-N-(2-hydroxyethyl)-N'-[4-[4-(me thoxycarbonyl)butyl]phenyl]-urea Melting point: 118°–120° C.; $R_f$ value: 0.67 (Silica gel; methylene chloride/cyclohexane/methanol/conc. aqueous ammonia=7:1.5:1.5:0.2)

(8) N-[trans-4-(ethoxycarbonyl)cyclohexyl]-N-(2-hydroxyethyl)-N'-[4-(1-trifluoroacetyl-4-piperidinyl)phenyl]-urea Reaction of the isocyanate with the cis/trans mixture of the amino compound and isolation of the trans compounds by chromatography over silica gel.

Melting point: 158°–160° C.; $R_f$ value: 0.32 (Silica gel; cyclohexane/ethyl acetate=1:1)

(9) N-(2-chloroethyl)-N'-[4-(1-trifluoroacetyl-4-piperidinyl)-phenyl]-urea $R_f$ value: 0.68 (Silica gel; ethyl acetate/cyclohexane=7:3)

(10) N-[4-[2-(n-butylsulfonylamino)-2-(methoxycarbonyl)-ethyl]phenyl]-N'-4-(cyanophenyl)-N-(2-hydroxyethyl)-urea $R_f$ value: 0.26 (Silica gel; cyclohexane/ethyl acetate=3:7)

(11) N-[4-(ethoxycarbonyl)phenyl]-N-(2-hydroxyethyl)-N'-[4-(1-trifluoroacetyl-4-piperidinyl)phenyl]-urea Melting point: 105°–108° C.; $R_f$ value: 0.23 (Silica gel; cyclohexane/ethyl acetate=1:1)

(12) N-[4-(4-cyano-1-trifluoroacetyl-4-piperidinyl)-phenyl]-N'-(2-hydroxyethyl)-N'-[trans-4-(methoxycarbonyl)cyclohexyl]-urea The 4-(4-cyano-1-trifluoroacetyl-4-piperidinyl)phenyl-isocyanate used as starting material is prepared from the corresponding amine by treatment with phosgene.

Melting point: from 189° C. (decomp.); $R_f$ value: 0.58 (Silica gel; ethyl acetate/cyclohexane=1:1)

(13) N-(2-chloroethyl)-N'-4-[4-(4-cyano-1-trifluoro-acetyl-4-piperidinyl)phenyl]-urea $R_f$ value: 0.66 (Silica gel; methylene chloride/methanol=96:4)

(14) N-(2-hydroxyethyl)-N-[trans-4-(methoxycarbonyl)-cyclohexyl]-N'-[4-(1-trifluoroacetyl-4-piperidinyl)-phenyl]-urea The 4-(1-trifluoroacetyl-4-piperidinyl)phenylisocyanate used as starting material is prepared from the corresponding amine by treatment with phosgene.

Melting point: 162°–163° C.; $R_f$ value: 0.50 (Silica gel; ethyl acetate/cyclohexane=5:1)

(15) N-[2-(1-tert.butyloxycarbonyl-1-aza-4-cycloheptyl)-ethyl]-N-(2-hydroxyethyl)-N'-[4-[2-(methoxycarbonyl)-ethyl]-phenyl]-urea The N-[2-(1-tert.butyloxycarbonyl-1-aza-4-cycloheptyl)-ethyl]-ethanolamine used as amine component is obtained by reacting 1-tert.butyloxycarbonyl-4-[2-(methane-sulfonyloxy)-ethyl]-1-azacycloheptane with ethanolamine. $R_f$ value: 0.27 (Silica gel; cyclohexane/ethyl acetate=3:7)

(16) N-[(ethoxycarbonyl)methyl]-N'-[4-[2-(methoxycarbonyl)-ethyl]phenyl]-urea

Melting point: 142°–144° C.; $R_f$ value: 0.71 (Silica gel; cyclohexane/ethyl acetate=2:8)

(17) N-[4-[2-(methoxycarbonyl)ethyl]phenyl]-N'-(1-hydroxy-2-propyl)-urea

Melting point: 132°–134° C.; $R_f$ value: 0.42 (Silica gel; ethyl acetate)

(18) N-(4-bromo-2-fluoro-phenyl)-N'-(2-chloroethyl)-urea

Melting point: 165°–167° C.

(19) N-(4-bromo-2-trifluoromethyl-phenyl)-N'-(2-chloroethyl)-urea

Melting point: 175°–177° C.

(20) N-(4-bromo-2-methyl-phenyl)-N'-(2-chloroethyl)-urea

Melting point: 180°–1820° C.

(21) N-(2-chloroethyl)-N'-[4-[2-(methoxycarbonyl)ethenyl]phenyl]-urea $R_f$ value: 0.41 (Silica gel; cyclohexane/ethyl acetate=1:1)

(22) N-(4-cyano-bicyclo[2.2.2]octan-1-yl)-N'-(2,2-dimethoxyethyl)-N'-[4-[2-(methoxycarbonyl)-ethyl]phenyl-urea The (4-cyano-bicyclo[2.2.2]octan-1-yl)isocyanate used as starting material is prepared from the corresponding amine-hydrochloride by reaction with phosgene. The N-[4-[2-(methoxycarbonyl)-ethyl]phenyl]aminoacetaldehyde-dimethyl acetal [$R_f$ value: 0.63 (Silica gel; cyclohexane/ethyl acetate=3:2)] used as amine component is obtained by reaction of methyl 3-(4-aminophenyl)-propionate with bromoacetaldehyde-dimethyl acetal in the presence of N-ethyl-diisopropylamine.

Melting point: 93°–94° C.; $R_f$ value: 0.40 (Silica gel; cyclohexane/ethyl acetate=1:1)

(23) N-(2-chloroethyl)-N'-[4-[2-(ethoxycarbonyl)-1-phenyl-ethyl]phenyl]-urea

Melting point: 109°–111° C.; $R_f$ value: 0.37 (Silica gel; cyclohexane/ethyl acetate=6:4)

(24) N-[2-(1-benzyl-1-azoniabicyclo[2.2.2]octan-4-yl)ethyl]-N-(2,2-dimethoxyethyl)-N'-[4-[2-(methoxycarbonyl)ethyl]phenyl]urea-chloride The N-[2-(1-benzyl-1-azoniabicyclo[2.2.2]-octan-4-yl)ethyl]aminoacetaldehyde-dimethylacetal-chloride-hydrochloride [melting point: 202°–204° C. (decomp.); $R_f$-value: 0.62 (Reversed Phase Silica gel, methanol/5% aqueous saline solution=6:4)]1 used as amine component is obtained by reaction of 1-benzyl-4-(2-chloroethyl)-1-azoniabicyclo[2.2.2]octane-chloride with aminoacetaldehyde-dimethylacetal.

$R_f$ value: 0.43 (Reversed Phase Silica gel; methanol/5% aqueous saline solution=6:4)

(25) N-[2-(1-tert.butyloxycarbonyl-4-piperidinyl)ethyl]-N-(2-hydroxyethyl)-N'-[2-cyano-4-[2-(methoxycarbonyl)ethyl]phenyl]urea The [2-cyano-4-[2-(methoxycarbonyl)ethyl]phenyl]-isocyanate used as starting material is obtained by reaction of the corresponding amine with phosgene.

$R_f$ value: 0.36 (Silica gel; ethyl acetate/cyclohexane=2:1)

EXAMPLE XII 1-(4-Cyanophenyl)-3-[4-[2-(N-trityl-5-tetrazolyl)ethyl]-phenyl]-imidazolidin-2-one Under nitrogen, 0.9 g of 1-(4-bromophenyl)-3-[4-[2-(N-trityl-5-tetrazolyl)ethyl]phenyl]-imidazolidin-2-one, 140 mg of potassium cyanide, 62 mg of palladium(II)-acetate, 142 mg of triphenylphosphine, 18 mg of calcium hydroxide and 7 ml of dry dimethylformamide are stirred for 1 hour at 100° C.

After cooling, ice water is added and the mixture is extracted several times with ethyl acetate. The combined organic phases are washed with saline solution, dried and evaporated down. The residue is purified by chromatography over a silica gel column using cyclohexane/ethyl acetate (1:1).

Yield: 270 mg (32% of theory); Melting point: 192°–194° C. (decomp.); $R_f$ value: 0.65 (Silica gel; cyclohexane/ethyl acetate=3:7)

EXAMPLE XIII 1-(4-Bromophenyl)-3-[4-[2-(N-trityl-5-tetrazolyl)ethyl]phenyl]-imidazolidin-2-one To 3.1 g of 1-(4-bromophenyl)-3-[4-[2-(5-tetrazolyl)-ethyl]phenyl]-imidazolidin-2-one in 80 ml of methylene chloride are added 0.91 g of triethylamine and 2.51 g of tritylchloride and the mixture is stirred for 1.5 hours at ambient temperature. The reaction mixture is washed with water, the organic phase is separated off, dried and evaporated down. The residue is briefly boiled with 70 ml of ethyl acetate, cooled somewhat and the product is suction filtered, washed with ethyl acetate and dried.

Yield: 3.38 g (68% of theory); Melting point: 194°–197° C. (decomp.); $R_f$ value: 0.67 (Silica gel; cyclohexane/ethyl acetate=1:1)

EXAMPLE XIV 1-(4-Bromophenyl)-3-[4-[2-(5-tetrazolyl)ethyl]phenyl]-imidazolidin-2-one 7.12 g of 1-(4-bromophenyl)-3-[4-[2-(2-cyanoethyl)phenyl)-imidazolidin-2-one and 7.7 g of tributyltin azide are stirred in 33 ml of dimethylformamide for 9 hours at 120°–130° C. A further 3 g of tributyltin azide are added and the mixture is heated for a further 50 hours. The reaction mixture is poured onto ice water and the mixture is stirred. The precipitate is suction filtered, washed with methanol and taken up in methylene chloride. This solution is washed with potassium fluoride solution, the organic phase is separated off, dried and evaporated down. The residue is purified by chromatography over a silica gel column with methylene chloride/methanol (95:5). The product is stirred again with methanol, suction filtered and dried.

Yield: 4.15 g (52% of theory); Melting point: 232°–236° C. (decomp.); $R_f$ value: 0.29 (Silica gel; methylene chloride/methanol=95:5)

EXAMPLE XV 1-(4-Bromophenyl)-3-[4-(2-cyanoethyl)phenyl]-imidazolidin-2-one

To 750 mg of 1-(4-bromophenyl)-3-[4-[2-(aminocarbonyl)-ethyl]-phenyl]-imidazolidin-2-one and 320 mg of pyridine in 10 ml of tetrahydrofuran are added dropwise at −10° C., with stirring, 460 mg of trifluoroacetic acid anhydride in 1 ml of tetrahydrofuran. After stirring overnight at ambient temperature the reaction mixture is diluted with ice water and the precipitate obtained is suction filtered, washed and dried.

Yield: 700 mg (98% of theory); Melting point: 188°–192° C.

EXAMPLE XVI

3-[4-(2-(Methoxycarbonyl)ethyl]phenyl]-1-(4-oxocyclohexyl)-3H-imidazol-2-one

To a solution of 12.8 g of N-(2,2-diethoxyethyl)-N-(1,4-dioxa-spiro[4.5]decan-8-yl)-N'-[4-[2-(methoxycarbonyl)ethyl]-phenyl]-urea in 20 ml of dioxane are added 5.6 ml of 3N hydrochloric acid and the mixture is stirred overnight at ambient temperature. The reaction mixture is evaporated down and the residue is distributed between methylene chloride and water. The aqueous phase is separated off and extracted with methylene chloride. The combined organic phases are washed with water, dried and evaporated down. The residue is purified by chromatography over a silica gel column using cyclohexane/ethyl acetate (35:65).

Yield: 2.3 g (25% of theory); Melting point: 113°–115° C.; $R_f$ value: 0.25 (Silica gel; cyclohexane/ethyl acetate=25:75)

EXAMPLE XVII

1-[4-(2-(Aminocarbonyl)ethyl]phenyl]-3-(4-bromophenyl)imidazolidin-2-one 9.2 g of 3-(4-bromophenyl)-1-[4-(2-carboxyethyl)phenyl]imidazolidin-2-one are mixed with 3.8 g of N,N'-carbonyldiimidazole in a mixture of 50 ml of tetrahydrofuran and 25 ml of dimethylformamide and the resulting mixture is stirred for 2.5 hours at 80° C. After cooling, it is poured onto a mixture of 20 ml of concentrated aqueous ammonia and loog-of ice and stirred for 15 minutes. The product is suction filtered and dried.

Yield: 8.8 g (97% of theory); Melting point: 248°–253° C.

EXAMPLE XVIII 4-(4-Cyano-1-trifluoroacetyl-4-piperidinyl)-nitrobenzene

To 1.6 g of 4-cyano-4-phenyl-1-trifluoroacetyl-piperidine (prepared by reacting 4-cyano-4-phenyl-piperidine with trifluoroacetic acid anhydride in the presence of N-ethyl-diisopropylamine) in 5 ml of conc. sulfuric acid, with cooling in an ice/acetone cooling bath, are added dropwise 590 mg of potassium nitrate dissolved in 5 ml of conc. sulfuric acid. After 1.5 hours stirring at ambient temperature the mixture is poured onto ice, the precipitate is suction filtered, dissolved in ethyl acetate and the ethyl acetate solution is washed with water and saline solution, then dried and evaporated down. The residue is stirred with tert.butylmethylether, suction filtered and washed with tert.butylmethylether.

Yield: 500 mg (26% of theory); Melting point: 135°–138° C.

The following compounds are obtained analogously to Example XVIII (1) 4-(1-trifluoroacetyl-4-piperidinyl)-nitrobenzene The nitration is carried out in glacial acetic acid/acetic anhydride with fuming nitric acid.

Melting point: 96°–100° C.; $R_f$ value: 0.50 (Silica gel, cyclohexane/ethyl acetate=2:1).

(2) 4-(4-nitrophenyl)-quinuclidine

Melting point: 130°–135° C.; $R_f$ value: 0.38 (Silica gel; methylene chloride/methanol/conc. aqueous ammonia=9:1:0.3)

(3) 4-methyl-4-(4-nitrophenyl)-1-trifluoroacetyl-piperidine

The nitration is carried out in glacial acetic acid/acetic anhydride with fuming nitric acid. The starting material [$R_f$ value: 0.72 (Silica gel; cyclohexane/ethyl acetate=2:1)] is obtained by reaction of 4-methyl-4-phenyl-piperidine with trifluoroacetic acid anhydride in the presence of N-ethyl-diisopropylamine.

$R_f$ value: 0.52 (Silica gel; cyclohexane/ethyl acetate=7:3).

EXAMPLE XIX

Methyl trans-4-[(2-hydroxyethyl)amino]-cyclohexanecarboxylate 13 g of methyl trans-4-[N-benzyl-N-(2-hydroxyethyl)amino]-cyclohexanecarboxylate are hydrogenated in 150 ml of methanol with 3.5 g of palladium on activated charcoal (10% palladium) under a hydrogen pressure of 50 psi for 20 minutes at 50° C. The catalyst is suction filtered and the filtrate is evaporated to dryness. (The starting material is obtained from methyl trans-4-amino-cyclohexanecarboxylate by reacting with benzaldehyde and hydrogen in the presence of Raney-nickel and subsequently reacting with 2-bromoethanol in the presence of N-ethyl-diisopropylamine).

Yield: 8.3 g (93% of theory); Melting point: 66°–68° C. $R_f$ value: 0.60 (Silica gel, methylene chloride/methanol/conc. aqueous ammonia=4:1:0.2).

The following compounds are obtained analogously to Example XIX:

(1) methyl trans-4-[(2,2-diethoxyethyl)amino]-cyclohexanecarboxylate

The starting material is obtained by reacting methyl trans-4-amino-cyclohexanecarboxylate with benzaldehyde and hydrogen in the presence of Raney-nickel and subsequently reacting with bromoacetaldehyde-diethylacetal in the presence of N-ethyl-diisopropylamine.

$R_f$ value: 0.65 (Silica gel; methylene chloride/methanol/conc. aqueous ammonia=9:1:0.1)

(2) 4-methyl-4-phenyl-piperidine

The debenzylation is carried out in the presence of palladium hydrochloride on charcoal.

$R_f$ value: 0.60 (Reversed Phase Silica gel; methanol/5% aqueous saline solution=6:4)

(3) 1-(4-hydroxyphenyl)-3-[trans-4-(methoxycarbonyl) cyclohexyl]-imidazolidin-2-one Carried out in dioxane.

The starting material, 1-[4-(benzyloxy)phenyl]-3-[trans-4-(methoxycarbonyl)cyclohexyl]-3H-imidazol-2-one [melting point: 183°–185° C., $R_f$ value=0.49; (Silica gel; cyclohexane/ethyl acetate=1:1)], is obtained by treating N-[4-(benzyloxy)phenyl]-N'-(2,2-diethoxyethyl)-N'-[trans-4-(methoxycarbonyl)cyclohexyl]-urea with trifluoroacetic acid in methylene chloride at ambient temperature.

Melting point: 184°–186 ° C. $R_f$ value: 0.26 (Silica gel; cyclohexane/ethyl acetate=1:1)

(4) tert.butyl (trans-4-aminocyclohexyl)-oxyacetate

The starting material, tert.butyl [trans-4(-dibenzylamino) cyclohexyl]-oxyacetate [$R_f$ value: 0.51; (Silica gel; cyclohexane/ethyl acetate=4:1)], is obtained by reacting trans-4-(dibenzylamino)cyclo-hexanol with tert.butyl bromoacetate in toluene/50% sodium hydroxide solution in the presence of tetrabutylammonium-hydrogen sulphate.

$R_f$ value: 0.56 (Reversed Phase Silica gel; methanol/5% aqueous saline solution=6:4)

EXAMPLE XX

N-[2-(1-tert.butyloxycarbonyl-4-piperidinyl)ethyl]-N'-[4-[2-(n-butylsulfonylamino)-2-(methoxycarbonyl)-ethyl]-phenyl]-N-(2-hydroxyethyl)-urea 3.25 g of N,N'-carbonyldiimidazole and 2.3 g of imidazole are dissolved in 60 ml of tetrahydrofuran and cooled to 0° C. under nitrogen. 6.15 g of 4-[2-(n-butylsulfonylamino)-2-(methoxycarbonyl)-ethyl]-aniline in 30 ml of tetrahydrofuran are rapidly added dropwise with stirring and the mixture is stirred for a further 4 minutes with cooling. Then 6 g of N-[2-(1-tert.butyloxycarbonyl-4-piperidinyl)ethyl]-ethanolamine (prepared by reacting 1-tert.butyloxycarbonyl-4-[2-(methanesulfonyloxy)ethyl]-piperidine with ethanolamine) in 30 ml of tetrahydrofuran are added dropwise. After stirring overnight at ambient temperature the mixture is evaporated down, taken up in tert.butyl-methylether and washed with dilute citric acid and saline solution. The organic phase is dried, concentrated by evaporation and the residue is purified by chromatography over a silica gel column.

Yield: 1.6 g (13% of theory); $R_f$ value: 0.31 (Silica gel; methylene chloride/methanol=95:5).

The following compounds are obtained analogously to Example XX:

(1) N-[2-(1-tert.butyloxycarbonyl-4-piperidinyl)ethyl]-N-(2-hydroxyethyl)-N'-[4-[2-(O,O'-diethylphosphono)ethyl] phenyl]-urea $R_f$ value: 0.28 (Silica gel; ethyl acetate/methanol=15:1).

(2) N-(2-cyano-1,2,3,4-tetrahydro-6-naphthyl)-N'-(2,2-diethoxyethyl)-N'-[trans-4-(methoxycarbonyl)cyclohexyl]-urea $R_f$ value: 0.55 (Silica gel; cyclohexane/ethyl acetate=1:1).

(3) N-[2-(1-tert.butyloxycarbonyl-4-piperidinyl)ethyl]-N-(2,2-dimethoxyethyl)-N'-(2-methoxycarbonyl-6-naphthyl)-urea The N-[2-(1-tert.butyloxycarbonyl-4-piperidinyl)ethyl]-aminoacetaldehyde-dimethylacetal used as starting material is obtained by reacting 1-tert.butyloxy-carbonyl-4-[2-(methanesulphonyloxy)ethyl]-piperidine with aminoacetaldehydedimethylacetal.

$R_f$ value: 0.33 (Silica gel; cyclohexane/ethyl acetate=1:1)

(4) N-[2-(1-tert.butyloxycarbonyl-4-piperidinyl)ethyl]-N-(2,2-dimethoxyethyl)-N'-(2-methoxycarbonyl-1,2,3,4-tetrahydro-6-naphthyl)-urea The 6-amino-2-methoxycarbonyl-1,2,3,4-tetrahydro-naphthalenehydrochloride (Melting point: 260°–261° C.) used as starting material is obtained by refluxing 2-cyano-6-amino-1,2,3,4-tetrahydronaphthalene in semi-concentrated hydrochloric acid and subsequent esterification with thionylchloride/methanol.

$R_f$ value: 0.40 (Silica gel; cyclohexane/ethyl acetate=1:1).

(5) N-[4-(4-quinuclidinyl)phenyl]-N'-(2,2-diethoxyethyl)-N'-[trans-4-(methoxycarbonyl)cyclohexyl]-urea $R_f$ value: 0.22 (Reversed Phase Silica gel; methanol/5% aqueous saline solution=6:4).

(6) N-(2,2-diethoxyethyl)-N-[trans-4-(methoxycarbonyl) cyclohexyl]-N'-[4-(4-methyl-1-trifluoroacetyl-4-piperidinyl)phenyl]-urea $R_f$ value: 0.70 (Silica gel; methylene chloride/ethyl acetate=4:1).

(7) N-[4-(benzyloxy)phenyl]-N'-(2,2-diethoxyethyl)-N'-[trans-4-(methoxycarbonyl)cyclohexyl]-urea $R_f$ value: 0.35 (Silica gel; methylene chloride/ethyl acetate=100:5).

EXAMPLE XXI

1-Cyano-3-[2-(1-tert.butyloxycarbonyl-4-piperidinyl)ethyl]-3-(2-hydroxyethyl)-4-[4-[2-(methoxycarbonyl)-ethyl] phenyl]-quanidine 7.1 g of cyanimino-[4-[2-(methoxycarbonyl) ethyl] phenyl]-phenoxy-methane and 7.2 g of N-[2-(1-tert.butyloxycarbonyl-4-piperidinyl) ethyl]-ethanolamine (prepared by reacting 1-tert.butyloxycarbonyl-4-[2-(methanesulfonyloxy)ethyl]-piperidine with ethanolamine) are ref luxed in 150 ml of isopropanol for 20 hours. The reaction mixture is evaporated down and the residue is purified by chromatography over a silica gel column with methylene chloride/ethyl acetate (4:6).

Yield: 4.6 g (46% of theory); $R_f$ value: 0.26 (Silica gel, methylene chloride/ethyl acetate=4:6).

EXAMPLE XXII

Cyanimino-[4-[2-(methoxycarbonyl)ethyl]phenyl]-phenoxymethane 7.3 g of diphenyl cyanocarbimidate and 5.0 g of methyl 3-(4-aminophenyl)propionate are stirred in 100 ml of isopropanol at ambient temperature for 20 hours. The solid matter is suction filtered, washed with isopropanol and petroleum ether and dried at 50° C.

Yield: 7.3 g (81% of theory); Melting point: 156°–158° C.; $R_f$ value: 0.62 (Silica gel, methylene chloride/ethyl acetate=9:1).

EXAMPLE XXIII 4-(2-Hydroxyethyl)-quinuclidine×BH$_3$ 7 g of 70% perchloric acid are added dropwise, with stirring, to 2.65 g of 4-(2-methoxyvinyl)-quinuclidine in 20 ml of toluene. After 1.5 hours stirring at ambient temperature the mixture is diluted with toluene and made alkaline with saturated potassium carbonate solution. The organic phase is decanted off and the aqueous phase is stirred 3 times with tert.butyl-methylether. The combined organic phases are evaporated down. The residue is dissolved in 20 ml of water and mixed with 360 mg of sodium borohydride. After standing overnight the mixture is acidified with citric acid, made alkaline once more and extracted several times with tert.butyl-methylether, ethyl acetate and methyl-ethyl-ketone. The combined organic phases are dried and evaporated down. The residue is dissolved in 20 ml of tetrahydrofuran and mixed with 15 ml of 1M borane in tetrahydrofuran under nitrogen in a dry ice bath. After standing at ambient temperature overnight 1 ml of methanol is added dropwise and the mixture is evaporated down. The residue is taken up in tert.butyl-methylether, washed with water and saline solution, dried and evaporated down. The residue is purified by chromatography over a silica gel column with cyclohexane/ethyl acetate (1:1).

Yield: 0.80 g (30% of theory); $R_f$ value: 0.15 (Silica gel; cyclohexane/ethyl acetate=1:1).

EXAMPLE XXIV 4-(2-Methoxyvinyl)-quinuclidine

To 9.93 g of methoxymethyl-triphenylphosphonium chloride in 45 ml of tetrahydrofuran 17.6 ml of 1.6M n-butyllithium in hexane are added dropwise, with stirring at ambient temperature. After 10 minutes a solution of 3.4 g of quinuclidine-4-aldehyde in 20 ml of tetrahydrofuran is added dropwise at 0° C. After 3 hours stirring at ambient temperature the mixture is evaporated down, the residue is cooled in an ice bath and mixed with 20 ml of 2N citric acid solution and some ice water. It is extracted 3 times with chloroform. The aqueous phase is evaporated down somewhat, made alkaline and extracted with tert.butylmethylether. The combined extracts are dried and evaporated down.

Yield: 2.4 g (58% of theory); $R_f$ value: 0.27 and 0.36 (Silica gel; methylene chloride/methanol/conc. aqueous ammonia=80:20:3)

EXAMPLE XXV 4-(4-Iodophenyl)-1-trifluoroacetyl-piperidine 24.6 g of 4-phenyl-1-trifluoroacetyl-piperidine (prepared by reacting 4-phenylpiperidine with trifluoroacetic acid anhydride in the presence of N-ethyl-diisopropylamine), 9.7 g of iodine, 4.5 g of periodic acid-dihydrate, 47.9 ml of glacial acetic acid, 9.6 ml of water and 1.4 ml of conc. sulfuric acid are stirred for 6 hours at 70° C. After standing overnight at ambient temperature the mixture is evaporated to dryness, mixed with toluene and evaporated down once more. The residue is stirred vigorously with 600 ml of tert.butylmethylether and 300 ml of 15% sodium disulphite solution for 5 minutes. It is suction filtered, the organic phase is separated off and extracted twice with sodium disulphite solution. The organic phase is separated off, dried and evaporated down. The residue is purified by chromatography over a silica gel column using cyclohexane/ethyl acetate (3:1).

Yield: 18.3 g (50% of theory, contains about 10% starting material); $R_f$ value: 0.43 (Silica gel; cyclohexane/ethyl acetate=4:1)

EXAMPLE XXVI

3-[4-[2-(Methoxycarbonyl)ethyl]phenyl]-hydantoin 22.1 g of N-[(ethoxycarbonyl)methyl]-N'-[4-[2-(methoxycarbonyl)-ethyl]phenyl]-urea in 200 ml of toluene are mixed with 100 mg of potassium tert.butoxide at boiling temperature and then refluxed. After 30 minutes 200 mg of potassium tert.butoxide are added and the mixture is heated for a further 30 minutes. The reaction mixture is cooled, mixed with 0.3 ml of glacial acetic acid and evaporated down. The residue is distributed between water and ethyl acetate, the organic phase is separated off, washed with saline solution, dried and evaporated down. The residue is purified by chromatography over a silica gel column with cyclohexane/ethyl acetate (3:7).

Yield: 14.4 g (77% of theory); Melting point: 110°–112° C.; $R_f$ value: 0.37 (Silica gel; cyclohexane/ethyl acetate=2:8)

The following compound is obtained analogously to Example XXVI:

(1) 1-[4-[2-(methoxycarbonyl)ethyl]phenyl]-hydantoin

Prepared from N-[(aminocarbonyl)methyl]-N-(methoxycarbonyl)-4-[2-(methoxycarbonyl)ethyl]-aniline in the presence of 1 molar equivalent of potassium tert.butoxide.

Melting point: 228°–233° C.; $R_f$ value: 0.42 (Silica gel; methylene chloride/methanol=95:5)

EXAMPLE XXVII

1-[4-[2-(Methoxycarbonyl)ethyl]phenyl]-4,5-dimethyl-3H-imidazol-2-one 2.4 g of N-[4-[2-(methoxycarbonyl)ethyl]phenyl]-urea [melting point: 152°–154° C. (sintering from 145° C.); prepared from methyl 3-(4-aminophenyl)propionate by reacting with potassium cyanate in the presence of glacial acetic acid] and 2.9 g of acetoin are heated to 180° C. for 1 hour under nitrogen. The reaction mixture is cooled stirred with ice water and the solid substance is suction filtered. The product is washed with water and diethylether and dried at 100° C.

Yield: 1.6 g (54% of theory); Melting point: 176°–181° C.; $R_4$ value: 0.11 (Silica gel; cyclohexane/ethyl acetate= 2:8)

EXAMPLE XXVIII

N-[(Aminocarbonyl)methyl]-N-(methoxycarbonyl)-4-[2-(methoxycarbonyl)ethyl]-aniline To 21.8 g of N-(carboxymethyl)-N-(methoxycarbonyl)-4-[2-(methoxycarbonyl)ethyl]-aniline [$R_f$ value: 0.57 (silica gel; toluene/dioxane/ethanol/glacial acetic acid= 90:10:10:6), prepared by hydrogenating N-[(benzyloxycarbonyl)methyl]-N-(methoxycarbonyl)-4-(2-(methoxycarbonyl)ethyl]-aniline in the presence of. palladium/activated charcoal] in 70 ml of methylene chloride, 7.3 ml of thionyl chloride are rapidly added dropwise and one drop dimethylformamide is added. The mixture is refluxed for 4 hours, cooled, left to stand overnight and then evaporated down. It is mixed with toluene and again concentrated by rotary evaporation. The residue is taken up in 200 ml of dioxane and ammonia is passed over the solution until an ammonical reaction is obtained. The reaction mixture is evaporated down, the residue is stirred with ice water and the solid matter is suction filtered. The product is washed with water and tert.butyl-methylether and dried.

Yield: 16.2 g (75% of theory); $R_f$ value: 0.30 (Silica gel; toluene/dioxane/ethanol/glacial acetic acid=90:10:10:6)

EXAMPLE XXIX

N-[(Benzyloxycarbonyl)methyl]-N-(methoxycarbonyl)-4-[2-(methoxycarbonyl)ethyl]-aniline To 29.5 g of N-[(benzyloxycarbonyl)methyl]-4-[2-(methoxycarbonyl)ethyl]-aniline [$R_f$ value: 0.42 (Silica gel; cyclohexane/ethyl acetate=7:3), prepared by reacting methyl 3-(4-aminophenyl)propionate with benzyl bromoacetate in the presence of N-ethyl-diisopropyl-amine] and 0.3 g of 4-dimethylaminopyridine in 200 ml of pyridine, 27 ml of methyl chloroformate are added dropwise whilst cooling with ice. Then the mixture is stirred overnight at ambient temperature. A further 14 ml of methyl chloroformate are added dropwise and again the mixture is stirred overnight. The reaction mixture is evaporated down, the residue is distributed between water and ethyl acetate and the organic phase is separated off. After washing with citric acid solution, water and saline solution, the mixture is dried and evaporated down. The residue is purified by chromatography over a silica gel column with cyclohexane/ethyl acetate (75:25).

Yield: 31.0 g (89% of theory); $R_f$ value: 0.31 (Silica gel; cyclohexane/ethyl acetate=7:3)

EXAMPLE XXX

1-[4-[2-(Methoxycarbonyl)ethyl]phenyl]-3H-benzimidazol-2-one

To a solution of 1.2 g of 2-[[4-[2-(methoxycarbonyl)ethyl]-phenyl]amino]-aniline in 5 ml of methylene chloride are added 0.94 g of N,N'-carbonyldiimidazole and the mixture is stirred overnight at ambient temperature. The reaction mixture is diluted with methylene chloride, washed with citric acid solution and water, dried and concentrated by rotary evaporation. The residue is purified by chromatography over a silica gel column with methylene chloride/ethyl acetate (75:25).

Yield: 0.9 g (69% of theory); Melting point: 168°–170° C. $R_f$ value: 0.31 (Silica gel; cyclohexane/ethyl acetate=1:1)

EXAMPLE XXXI

1-[2-(1-tert.Butyloxycarbonyl-4-piperidinyl)ethyl]imidazolidin-2-one

To 8.9 g of imidazolidin-2-one in 150 ml of dimethylformamide are added 10.4 g of potassium tert.-butoxide and the mixture is heated to 70° C. for 30 minutes. To this are added 3.5 g of 1-tert.butyloxycarbonyl-4-(2-iodo-ethyl)-piperidine in 5 ml of dimethylformamide and the mixture is stirred overnight at ambient temperature. Then 5.3 ml of glacial acetic acid are added dropwise, the reaction mixture is evaporated down and the residue is twice evaporated down with toluene. The residue is distributed between ethyl acetate and water, the aqueous phase is extracted four more times with ethyl acetate and the combined organic phases are washed with water, dried and concentrated by rotary evaporation. The residue is purified by chromatography over a silica gel column with ethyl acetate/methanol (100:3).

Yield: 1.9 g (61% of theory); Melting point: 111°–113° C.; $R_f$ value: 0.30 (Silica gel; methylene chloride/methanol=100:4)

EXAMPLE XXXII

2-Cyano-6-amino-1,2,3,4-tetrahydronaphthalene 0.92 ml of bromine are added slowly, dropwise, to 4.0 g of sodium hydroxide in 25 ml water on ice. The mixture is stirred for 10 minutes, then, 3.0 g of finely pulverized 2-cyano-6-aminocarbonyl-1,2,3,4-tetrahydro-napthalene (Melting point: 180°–182° C., produced by reacting 2-cyano-1,2,3,4-tetrahydro-napthalene-6-carbonic acid with thionyl chloride followed by treatment with concentrated aqueous ammonia in the presence of dioxane) are added, and the mixture is removed from the cooling bath. After 4 hours, 2.5 g of sodium disulphite are added, and the mixture is adjusted to a pH of 1–2, on ice, with hydrochloric acid. The mixture is stirred for 15 minutes, warmed to ambient temperature and filtered. On ice, the mother liquor is made alkaline with sodium hydroxide, the precipitate is suction filtered, washed with ice-cold water and dried.

Yield: 0.87 g (34% of theory), Melting point: 120°–122 ° C.; $R_f$ value: 0.50 (Silica gel; cyclohexane/ethyl acetate=1:1)

EXAMPLE XXXIII

1-[4-[2-(Methoxycarbonyl)ethenyl]-2-fluoro-phenyl]-imidazolidin-2-one 19.55 g of 1-(4-bromo-2-fluoro-phenyl)-imidazolidin-2-one, 1.96 g of palladium(II)acetate, 2.61 g of tri-o-tolylphosphine, 21.7 ml of methyl acrylate, 54.5 ml of triethylamine and 32.6 ml of dimethylformamide are stirred together for 2.5 days at a bath temperature of 100° C. The mixture is cooled, evaporated down and the residue is purified by chromatography over a silica gel column with methylene chloride/methanol (100:1).

Yield: 9.07 g (46% of theory), Melting point: 182°–184° C.; $R_f$ value: 0.58 (Silica gel; methylene chloride/methanol 20:1)

The following compounds are obtained analogously to Example XXXIII:

(1) 1-[4-[2-(methoxycarbonyl)ethenyl]-2-trifluoromethyl-phenyl]-imidazolidin-2-one Melting point: 145°–150° C.

(2) 1-[4-[2-(methoxycarbonyl)ethenyl]2-methyl-phenyl]-imidazolidin-2-one

Melting point: 149°–151° C.

(3) methyl 3-(4-amino-3-cyano-phenyl)acrylate

The starting material, 4-bromo-2-cyano-aniline-hydrobromide, is obtained by reacting 2-cyano-aniline with bromine in glacial acetic acid.

$R_f$ value: 0.48 (Silica gel; cyclohexane/ethyl acetate=2:1)

The product is converted into methyl 3-(4-amino-3-cyano-phenyl)-propionic acid by hydrogenation in ethyl acetate in the presence of palladium on activated charcoal.

$R_f$ value: 0.55 (Silica gel; cyclohexane/ethyl acetate=2:1)

EXAMPLE XXXIV

1-Benzyl-4-methyl-4-phenyl-piperidine 38.4 ml of 1.6M butyl lithium in hexane are added dropwise to 15.3 g of 1-benzyl-4-phenyl-1,2,3,6-tetrahydro-pyridine in 160 ml of tetrahydrofuran at −10° to −15° C. The mixture is stirred for 15 minutes, cooled to −50° C. and at this temperature, a solution of 10.7 g of methyl iodide in 140 ml of tetrahydrofuran is added, dropwise. The mixture is warmed to 15° C. within an hour, 80 ml of water are added and the phases are separated. The organic phase is washed with water and saturated saline solution, dried and evaporated down. The residue is hydrogenated for 8 hours in 150 ml of ethanol in the presence of 2.0 g of palladium on charcoal (10% palladium) at ambient temperature and under a hydrogen pressure of 50 psi. The mixture is filtered and the filtrate is evaporated down. The residue is purified by chromatography over a silica gel column with methylene chloride/ethanol/conc. aqueous ammonia (100:3:0.4).

Yield: 4.1 g (23% of theory); $R_f$ value: 0.37 (Silica gel; methylene chloride/ethanol/conc. aqueous ammonia=100:3:0.4)

EXAMPLE XXXXV

1-Amino-4-cyano-bicyclo[2.2.2]octane-hydrochloride 2.6 ml of ethylchloroformate are rapidly added, dropwise, to a solution of 4.9 g of 1-carboxy-4-cyano-bicyclo[2.2.2]-octane and 3.8 ml of triethylamine in 130 ml of chloroform at −10° C. After 15 minutes of stirring, ammonia gas is introduced to the mixture for 10 minutes. The mixture is stirred for 10 minutes at 0° C., warmed to ambient temperature and after an hour, evaporated to dryness. The residue is stirred with water under heating, cooled, suction filtered, washed with water and dried. The 1-aminocarbonyl-4-cyano-bicyclo[2.2.2]octane [4.2 g (86% of theory); $R_f$ value: 0.78 (Silica gel; methylene chloride/methanol/conc. aqueous ammonia=4:1:0.2)] obtained is suspended in 100 ml of acetonitrile/water (1:1), combined with 15.0 g of bis(trifluoroacetoxy)iodobenzene and stirred for 18 hours at ambient temperature. The reaction mixture is evaporated down to half its volume, shaken twice with ehtyl acetate and the aqueous phase is adjusted to a pH of 12 to 13. The aqueous phase is extracted 3 times with ethyl acetate and the combined organic phases are washed with saturated saline solution and dried. The residue is dissolved in ethyl acetate acid and a little acetone and ethereal hydrochloric acid are added. The mixture is cooled in an ice-bath, suction filtered and the product is washed with ethyl acetate.

Yield: 2.5 g (58% of theory); Melting point: >250° C.; $R_f$ value: 0.85 (Reversed Phase Silica gel; methanol/5% aqueous saline solution=6:4)

EXAMPLE XXXVI

Methyl (trans-4-aminocyclohexyl) oxyacetate-hydrochloride

To a solution of 59.4 g of tert.butyl(trans-4-aminocyclohexyl)oxyacetate in 500 ml of methanol cooled in an ice-bath, hydrochloric acid gas is introduced for 1 hour and the mixture is stirred overnight at ambient temperature. The mixture is evaporated to dryness and the residue is triturated with acetone and the solid material is suction filtered and dried.

Yield 34.3 g (59% of theory), Melting point: 157°–160° C.

EXAMPLE XXXVII 3-(2-Hydroxyethyl)-pyrrolidine a) 1-Benzyloxycarbonyl-2-pyrrolidinone Prepared by the treatment of 2-pyrrolidinone with potassium tert.butoxide followed by reaction with benzylchloroformate.

Boiling point: 148°–155° C. (0.2 mbar); $R_f$ value: 0.36 (Silica gel; cyclohexane/ethyl acetate=1:1)

b) 1-Benzyloxycarbonyl-3-(tert.butyloxycarbonylmethyl)-2-pyrrolidinone

Prepared by the treatment of 1-benzyloxycarbonyl-2-pyrrolidinone with lithium-bis-(trimethylsilylamide), followed by reaction with tert.butyl bromoacetate at −70° C.

$R_f$ value: 0.64 (Silica gel; cyclohexane/ethyl acetate=1:1)

c) 3-(tert.Butyloxycarbonylmethyl)-2-pyrrolidinone

Prepared by the catalytic hydrogenation of 1-benzyloxycarbonyl-3-(tert.butyloxycarbonylmethyl)-2-pyrrolidinone in ethyl acetate in the presence of palladium/activated charcoal.

$R_f$ value: 0.20 (Silica gel; cyclohexane/ethyl acetate=1:1)

d) 3-(2-Hydroxyethyl)-pyrrolidine

Prepared by reacting 3-(tert.butyloxycarbonylmethyl)-2-pyrrolidinone with lithium aluminium hydride.

$R_f$ value: 0.89 (Reversed Phase Silica gel; methanol/15% aqueous saline solution=6:4)

EXAMPLE XXXVIII

1-Benzyl-4-(2-chloroethyl)-1-azoniabicyclo[2.2.2]octanechloride a) 1-Benzyl-4,4-bis-(ethoxycarbonYlmethyl)-piperidine Prepared analogously to S. M. McElvain and R. E. Lyle, Jr., J. Am. Chem. Soc. 72, 384 (1950) from 1-benzyl-4-piperidinone.

$R_f$ value: 0.48 (Silica gel; methylene chloride/methanol=95:5)

b) 1-Benzyl-4,4-bis-(2-hydroxyethyl)-piperidine

Prepared analogously to M. E. Freed and L. M. Rice, J. Heterocyclic Chem. 2, 214 (1965) from 1-benzyl-4,4-bis-(ethoxycarbonylmethyl)-piperidine $R_f$ value: 0.18 (Silica gel; methylene chloride/methanol=9:1)

c) 1-Benzyl-4,4-bis-(2-chloroethyl)-piperidine-hydrochloride

Prepared analogously to M. E. Freed and L. M. Rice, J. Heterocyclic Chem. 2, 214 (1965) from 1-benzyl-4,4-bis-(2-hydroxyethyl)-piperidine.

Melting point: 168°–170° C.

$R_f$ value: 0.45 (Reversed Phase Silica gel; methanol/5% aqueous saline solution=6:4)

d) 1-Benzyl-4-(2-chloroethyl)-1-azoniabicyclo[2.2.2]octane-chloride 10.5 g of 1-benzyl-4,4-bis-(2-chloroethyl)-piperidine-hydrochloride in 50 ml of tert.butyl-methylether are added to 31 ml of 1N sodium hydroxide solution with vigorous stirring. After stirring for 15 minutes, the organic phase is evaporated down. The residue is taken up in 30 ml of acetonitrile and heated at 80° C. for 15 minutes, cooled and evaporated down. The residue is stirred overnight in acetone, the solid material is suction filtered, washed with acetone and ether and dried in a desiccator.

Yield: 7.16 g (77% of theory), Melting point: 199°–201 ° C.; $R_f$ value: 0.55 (Reversed Phase Silica gel; methanol/5% aqueous saline solution=6:4)

EXAMPLE 1

2-(4-Amidinophenyl)-4-[4-(1-carboxy-2-propyl)phenyl]-5-methyl-4H-1,2,4-triazol-3-one×0.25 water 0.5 g of 2-(4-amidinophenyl)-4-[4-(1-methoxycarbonyl-2-propyl)-phenyl]-5-methyl-4H-1,2,4-triazol-3-one-hydrochloride are stirred in a mixture of 5 ml of semi-concentrated hydrochloric acid and 1 ml of glacial acetic acid at ambient temperature. After 30, 70 and 100 minutes, each time a further 1 ml of glacial acetic acid is added and the mixture is stirred overnight. It is evaporated to dryness, mixed with 5 ml of water and adjusted to a pH of 6 with 1N sodium hydroxide solution, with stirring. The precipitate is suction filtered, washed with a little ice water and dried.

Yield: 0.41 g (92% of theory); $R_f$ value: 0.55 (Reversed Phase Silica gel; methanol/10% aqueous saline solution=3:1); Calculated: C 62.57 H 5.65 N 18.24; Found: 62.70 5.71 18.00

The following compounds are obtained analogously to Example 1:

(1) 2-(4-amidinophenyl)-4-[4-(2-carboxy-1-propyl)phenyl]-5-methyl-4H-1,2,4-triazol-3-one×0.5 water $R_f$ value: 0.55 (Reversed Phase Silica gel; methanol/10% aqueous saline solution=3:1); Calculated: C 61.85 H 5.71 N 18.03; Found: 61.97 5.77 18.05

(2) 2-(4-amidinophenyl)-4-[4-(2-carboxyethyl)phenyl]-5-phenyl-4H-1,2,4-triazol-3-one×2 water $R_f$ value: 0.47 (Reversed Phase Silica gel; methanol/10% aqueous saline solution=3:1); Calculated: C 62.47 H 5.46 N 14.88; Found: 62.23 5.18 15.18

(3) 1-(1-amino-1,2,3,4-tetrahydronaphthalin-6-yl)-3-[4-(2-carboxyethyl)phenyl]-imidazolidin-2-one-hydrochloride Melting point: 236°–238° C.; $R_f$ value: 0.39 (Reversed Phase Silica gel; methanol/5% aqueous saline solution=6:4); Calculated: C 63.53 H 6.30 N 10.10 ° C.l 8.52; Found: 63.81 6.50 10.00 8.21

(4) 4-[4-(2-carboxyethyl)phenyl]-5-methyl-2-[2-(4-piperidinyl)ethyl]-4H-1,2,4-triazol-3-one-toluenesulphonate×water The starting material was present as toluenesulphonate.

$R_f$ value: 0.59 (Reversed Phase Silica gel; methanol/5% aqueous saline solution 6:4); Calculated,: C 56.92 H 6.61 N 10.21 S 5.84; Found: 56.82 6.74 9.95 5.88

(5) 1-(4-amidinophenyl)-3-[trans-4-(2-carboxyethyl)cyclohexyl]-imidazolidin-2,4-dione $R_f$ value: 0.45 (Reversed Phase Silica gel; methanol/5% aqueous saline solution=6:4)

(6) 1-[4-(2-carboxyethyl)phenyl]-3-[2-(4-piperidinyl)ethyl]-imidazolidin-2-one-hydrochloride×water Melting point: 216°–225° C.; $R_f$ value: 0.54 (Reversed Phase Silica gel; methanol/5% aqueous saline solution=6:4); Calculated: C 57.06 H 7.56 N 10.51 Cl 8.86; Found: 57.27 7.55 10.61 9.14

(7) 1-[4-(2-carboxy-1-pentyl)phenyl]-3-[2-(4-piperidinyl)-ethyl]-imidazolidin-2-one-hydrochloride (8) 4-[4-(2-carboxy-1-pentyl)phenyl]-5-methyl-2-(2-(4-piperidinyl)ethyl)-4H-1,2,4-triazol-3-one-hydrochloride $R_f$ value: 0.44 (Reversed Phase Silica gel; methanol/5% aqueous saline solution=6:4)

(9) 4-[4-(2-carboxy-3-methyl-1-butyl)phenyl]-5-methyl-2-[2-(4-piperidinyl)ethyl]-4H-1,2,4-triazol-3-one-hydrochloride

(10) 4-[4-(2-carboxy-1-butyl)phenyl]-5-methyl-2-[2-(4-piperidinyl)ethyl]-4H-1,2,4-triazol-3-one-hydrochloride

(11) 4-[4-(2-carboxy-1-propyl)phenyl]-5-methyl-2-[2-(4-piperidinyl)ethyl]-4H-1,2,4-triazol-3-one-hydrochloride

(12) 2-(4-amidinophenyl)-4-[4-(2-carboxy-1-pentyl)phenyl]-5-methyl-4H-1,2,4-triazol-3-one

(13) 4-(4-amidinophenyl)-2-[trans-4-(2-carboxyethyl)cyclohexyl]-4H-1,2,4-triazol-3-one

(14) 1-[4-(2-carboxyethyl)phenyl]-3-[2-(4-piperidinyl)-ethyl]-3,4,5,6-tetrahydro-1H-pyrimidin-2-one-hydrochloride $R_f$ value: 0.60 (Reversed Phase Silica gel; methanol/5% aqueous saline solution=6:4); Mass spectrum: $(M+H)^+=360$

(15) 1-(4-amidinophenyl)-3-[trans-4-[(carboxymethyl)oxy]-cyclohexyl]-imidazolidin-2-one

(16) 2-[4-(aminomethyl)phenyl]-4-[4-(2-carboxy-1-propyl)-phenyl]-5-methyl-4H-1,2,4-triazol-3-one-hydrochloride $R_f$ value: 0.69 (Reversed Phase Silica gel; methanol/10% aqueous saline solution=3:1)

(17) 4-[4-(2-carboxyethyl)phenyl]-5-methyl-2-[(1-piperazinyl)carbonylmethyl]-4H-1,2,4-triazol-3-one-hydrochloride

(18) 4-[4-(2-carboxyethyl)phenyl]-5-methyl-2-[2-(1-aza-4-cycloheptyl)ethyl]-4H-1,2,4-triazol-3-one-hydro-chloride

(19) 4-[4-(2-carboxyethyl)phenyl]-5-methyl-2-[2-(1,4-diaza-1-cycloheptyl)ethyl]-4H-1,2,4-triazol-3-one-dihydrochloride

(20) 1-[4-(4-carboxybutyl)phenyl]-3-(4-piperidinyl)imidazolidin-2-one-hydrochloride Melting point: 223°–225° C.; $R_f$ value: 0.46 (Reversed Phase Silica gel; methanol/5% aqueous saline solution=6:4)

(21) 1-(4-amidinophenyl)-3-[4-[2-(n-butylsulfonylamino)-2-carboxy-ethyl]phenyl]-imidazolidin-2-one-hydrochloride $R_f$ value: 0.43 (Reversed Phase Silica gel; methanol/5% aqueous saline solution=6:4)

(22) 4-[4-(2-(n-butylsulfonylamino)-2-carboxy-ethyl)phenyl]-5-methyl-2-[2-(4-piperidinyl)ethyl]-4H-1,2,4-triazol-3-one-hydrochloride

(23) 1-(4-amidinophenyl)-3-[4-[2-carboxy-2-(n-hexanoyl-amino)-ethyl]phenyl]-imidazolidin-2-one-hydrochloride

(24) 1-(4-amidinophenyl)-3-[4-[2-carboxy-2-(3-phenyl-propionylamino)-ethyl]phenyl]-imidazolidin-2-one-hydrochloride

(25) 1-(4-amidinophenyl)-3-[4-[2-(benzylsulfonylamino)-2-carboxy-ethyl]phenyl]-imidazolidin-2-one-hydrochloride

(26) 4-[4-[2-carboxy-2-(methanesulfonylamino)-ethyl]phenyl]-5-methyl-2-[2-(4-piperidinyl)ethyl]-4H-1,2,4-triazol-3-one-hydrochloride

(27) 4-[4-[2-(acetylamino)-2-carboxy-ethyl]phenyl]-5-methyl-2-[2-(4-piperidinyl)ethyl]-4H-1,2,4-triazol-3-one-hydrochloride

(28) 4-[4-(2-carboxy-1-octyl)phenyl]-5-methyl-2-[2-(4-piperidinyl)ethyl]-4H-1,2,4-triazol-3-one-hydrochloride

(29) 4-[4-(2-carboxyethyl)phenyl]-2-[2-(4-piperidinyl)ethyl]-4H-1,2,4-triazol-3-one×1.05 HCl×0.25 $H_2O$ Melting point: 252°–255° C.; $R_f$ value: 0.65 (Reversed Phase Silica gel; methanol/5% aqueous saline solution=6:4); Calculated: C 55.84 H 6.65 N 14.47 ° C.l 9.61; Found: 55.73 6.73 14.49 9.60

(30) 2-[4-(2-carboxyethyl)phenyl]-5-[2-(4-piperidinyl)ethyl]-3,4-dihydro-2H,5H-1,2,5-thiadiazole-1,1-dioxide $R_f$ value: 0.71 (Reversed Phase Silica gel; methanol/5% aqueous saline solution=6:4)

(31) 1-[4-(2-carboxyethyl)phenyl]-3-[(1-piperazinyl)carbonylmethyl]-imidazolidin-2-one-hydrochloride $R_f$ value: 0.58 (Reversed Phase Silica gel; methanol/5% aqueous saline solution=6:4);
Mass spectrum: $M^+=360$

(32) 1-[4-[2-(n-butylsulfonylamino)-2-carboxy-ethyl]phenyl]-3-[2-(4-piperidinyl)ethyl]-imidazolidin-2-one-hydrochloride $R_f$ value: 0.51 (Reversed Phase Silica gel; methanol/5% aqueous saline solution=6:4)

(33) 4-[4-(2-carboxyethyl)phenyl]-2-[2-(1-piperazinyl)ethyl]-4H-1,2,4-triazol-3-one×2.1 HCl×0.15 $H_2O$ $R_f$ value: 0.69 (Reversed Phase Silica gel; methanol/5% aqueous saline solution=6:4); Calculated: C 48.08 H 6.03 N 16.49 ° C.l 17.53; Found: 48.28 6.11 16.45 17.40 Mass spectrum: $M^+=345$

(34) 1-[4-(2-carboxyethyl)phenyl]-3-[2-(4-piperidinyl)ethyl]-3H-benzimidazol-2-one×1.1 HCl×0.4 $H_2O$ $R_f$ value: 0.38 (Reversed Phase Silica gel; methanol/5% aqueous saline solution=6:4); Calculated: C 62.67 H 6.61 N 9.53 Cl 8.85; Found: 63.06 6.58 9.48 8.51

(35) 1-[4-(aminomethyl)-bicyclo[2.2.2]octan-1-yl]-3-[4-(2-carboxyethyl)phenyl]-imidazolidin-2-one-hydrochloride Melting point: 334°–336° C.; $R_f$ value: 0.43 (Reversed Phase Silica gel; methanol/5% aqueous saline=6:4)

(36) 1-[4-(trans-4-carboxycyclohexyl)phenyl]-3-(4-piperidinyl)-imidazolidin-2-one-hydrochloride

(37) 2-[4-(2-carboxyethyl)phenyl]-5-methyl-4-[2-(4-piperidinyl)ethyl]-4H-1,2,4-triazol-3-one-hydrochloride

(38) 1-[2-(1-aza-4-cycloheptyl)ethyl]-3-[4-(2-carboxyethyl)-phenyl]-imidazolidin-2-one-hydrochloride Melting point: 205°–207° C.; $R_f$ value: 0.52 (Reversed Phase Silica gel; methanol/5% aqueous saline solution=6:4); Calculated: C 60.67 H 7.64 N 10.61 Cl 8.96; Found: 60.37 7.85 10.73 9.05

(39) 1-[trans-4-(2-carboxyethyl)cyclohexyl]-3-[2-(4-piperidinyl)ethyl]-imidazolidin-2-one-hydrochloride $R_f$ value: 0.55 (Reversed Phase Silica gel; methanol/5% aqueous saline solution=6:4); Calculated: C 58.82 H 8.83 N 10.83 Cl 9.14; Found: 58.52 9.04 10.65 9.02

(40) 1-[4-(2-carboxyethyl)phenyl]-3-[2-(2,2,6,6-tetramethyl-4-piperidinyl)ethyl]-imidazolidin-2-one-hydrochloride Melting point: >250° C.; $R_f$ value: 0.44 (Reversed Phase Silica gel; methanol/5% aqueous saline solution=6:4)

(41) 1-[4-(2-carboxyethyl)phenyl]-3-[2-( 4-piperidinyl)ethyl]-hydantoin-hydrochloride×0.6 $H_2O$ Melting point: 226°–230° C. (sintering from 220° C.) $R_f$ value: 0.56 (Reversed Phase Silica gel; methanol/5% aqueous saline solution=6:4); Calculated: C 56.11 H 6.74 N 10.33 Cl 8.71; Found: 55.72 6.71 10.32 9.11

(42) 3-[4-(2-carboxyethyl)phenyl]-1-[2-(4-piperidinyl)ethyl]-hydantoin-hydrochloride Melting point: 186°–189° C. $R_f$ value: 0.66 (Reversed Phase Silica gel; methanol/5% aqueous saline solution=6:4);

Calculated: C 57.64 H 6.62 N 10.61 Cl 8.96; Found: 57.52 6.81 10.39 8.86

(43) 1-[4-(2-carboxyethyl)phenyl]-3-[2-(4-piperidinyl)ethyl]-cis-4,5-dimethyl-imidazolidin-2-one-hydro-chloride Melting point: 157°–163° C. $R_f$ value: 0.53 (Reversed Phase Silica gel; methanol/5% aqueous saline solution=6:4)

(44) 1-(2-aminomethyl-1,2,3,4-tetrahydro-6-naphthyl)-3-(trans-4-carboxycyclohexyl)-imidazolidin-2-one-hydrochloride $R_f$ value: 0.55 (Reversed Phase Silica gel; methanol/5% aqueous saline solution=6:4); Calculated: C 61.83 H 7.41 N 10.30 Cl 8.69; Found: 61.86 7.44 10.30 8.80

(45) 1-(trans-4-carboxycyclohexyl)-3-[4-(3-oxo-4-quinuclidinyl)phenyl]-imidazolidin-2-one-hydrochloride

(46) 1-(5-aminopentyl)-3-[4-(2-carboxyethyl)phenyl]-imidazolidin-2-one-hydrochloride×0.2 $H_2O$ Calculated: C 56.80 H 7.40 N 11.69 Cl 9.86; Found: 56.62 7.42 11.98 9.46

(47) 1-[3-(cis-1-amino-2-cyclopentyl)propyl]-3-[4-(2-carboxyethyl)phenyl]-imidazolidin-2-one-hydrochloride

(48) 1-[2-[(cis-1-amino-2-cyclopentyl)oxy]ethyl]-3-[4-(2-carboxyethyl)phenyl]-imidazolidin-2-one-hydrochloride

(49) 1-(2-carboxy-1,2,3,4-tetrahydro-6-naphthyl)-3-[2-(4-piperidinyl)ethyl]-imidazolidin-2-one-hydrochloride×1 $H_2O$ Melting point: 274°–278° C.; Calculated: C 59.21 H 7.57 N 9.86 Cl 8.32; Found: 59.23 7.49 9.87 8.27; Mass spectrum: $M^+$=371

(50) 1-(trans-4-carboxycyclohexyl)-3-[4-(4-quinuclidinyl)-phenyl]-imidazolidin-2-one-hydrochloride×1.2 $H_2O$ $R_f$ value: 0.55 (Reversed Phase Silica gel; methanol/5% aqueous saline 6:4); Calculated: C 60.63 H 7.61 N 9.22 Cl 7.78; Found: 60.47 7.60 9.36 7.95; Mass spectrum: $M^+$=397

(51) 1-(trans-4-carboxycyclohexyl)-3-[4-[(2-aminoethyl)oxy]phenyl]imidazolidin-2-one-hydrochloride $R_f$ value: 0.58 (Reversed Phase Silica gel; methanol/5% aqueous saline=6:4)

EXAMPLE 2

2-(4-Amidinophenyl)-4-[4-(1-methoxycarbonyl-2-propyl)phenyl]-5-methyl-4H-1,2,4-triazol-3-one-hydrochloride 3.2 g of 2-(4-cyanophenyl)-4-[4-(1-ethoxycarbonyl-2-propyl)phenyl]-5-methyl-4H-1,2,4-triazol-3-one, suspended in 75 ml of dry methanol, are added to 120 ml of dry methanol saturated with hydrochloric acid gas at 0° C. The mixture is saturated with hydrochloric gas at 0° C., some petroleum ether is added and the mixture is stirred overnight at ambient temperature. The reaction mixture is evaporated down, 50 ml of dry methanol are added and the mixture is evaporated down once more. The residue is dissolved in 120 ml of methanol, methanolic ammonia is added to give a pH of 8–9, 2.28 g of ammonium acetate are added and the mixture is refluxed for 2 hours. After concentration by evaporation the residue is purified by chromatography over a silica gel column with methylene chloride/methanol (4:1). The product is dissolved in methanol/methylene chloride and combined with 5 ml of methanolic hydrochloric acid with stirring. The solution is evaporated almost to dryness, some more toluene is added and it is again evaporated to dryness.

Yield: 2.01 g (57% of theory) $R_f$ value: 0.40 (Reversed Phase Silica gel; methanol/10% aqueous saline solution= 3:1) The following compounds are obtained analogously to Example 2:

(1) 2-(4-amidinophenyl)-4-[4-(2-methoxycarbonyl-1-propyl)phenyl]-5-methyl-4H-1,2,4-triazol-3-one×1.1 hydrogen chloride $R_f$ value: 0.40 (Reversed Phase Silica gel; methanol/10% aqueous saline solution=3:1); Calculated: C 58.18 H 5.37 N 16.15 Cl 9.00; Found: 57.90 5.65 16.24 9.14

(2) 1-(4-amidinophenyl)-3-[trans-4-[2-(methoxycarbonyl)ethyl]cyclohexyl]-3H-imidazol-2-one-hydrochloride $R_f$ value: 0.59 (Reversed Phase Silica gel; methanol/10% aqueous saline solution=3:1)

(3) 1-(4-amidinophenyl)-3-[cis-4-[2-(methoxycarbonyl)ethyl]-cyclohexyl]-3H-imidazol-2-one-hydrochloride $R_f$ value: 0.46 (Reversed Phase Silica gel; methanol/5% aqueous saline solution=6:4)

(4) 2-(4-amidinophenyl)-4-[4-[2-(methoxycarbonyl)ethyl]-phenyl]-5-phenyl-4H-1,2,4-triazol-3-one-hydrochloride $R_f$ value: 0.37 (Reversed Phase Silica gel; methanol/10% aqueous saline solution=3:1)

(5) 1-(4-amidinophenyl)-3-[4-[2-( 5-tetrazolyl)ethyl]phenyl]-imidazolidin-2-one $R_f$ value: 0.50 (Reversed Phase Silica gel; methanol/5% aqueous saline solution=6:4)

(6) 2-(4-amidinophenyl)-4-[trans-4-[2-(methoxycarbonyl)ethyl]cyclohexyl]-4H-1,2,4-triazol-3-one-hydrochloride× $H_2O$ Melting point: 247° C. (decomp.); $R_f$ value: 0.35 (Reversed Phase Silica gel; methanol/5% aqueous saline solution=6:4); Calculated: C 53.58 H 6.62 N 16.44 Cl 8.32; Found: 53.80 6.81 16.44 8.17

(7) 1-(4-amidinophenyl)-3-[trans-4-[2-(methoxycarbonyl)ethyl]cyclohexyl]-imidazolidin-2,4-dione-hydrochloride $R_f$ value: 0.32 (Reversed Phase Silica gel; methanol/5% aqueous saline solution=6:4)

(8) 2-(4-amidinophenyl)-4-[4-[2-(methoxycarbonyl)-1-pentyl]-phenyl]-5-methyl-4H-1,2,4-triazol-3-one-hydrochloride (9) 4-(4-amidinophenyl)-2-[trans-4-[2-(methoxycarbonyl)ethyl]cyclohexyl]-4H-1,2,4-triazol-3-one-hydrochloride

(10) 1-(4-amidinophenyl)-3-[trans-4-[(methoxycarbonylmethyl)-oxy]cyclohexyl]-imidazolidin-2-one-hydrochloride

(11) 1-(4-amidinophenyl)-3-[4-[2-(n-butylsulfonylamino)-2-(methoxycarbonyl)-ethyl]phenyl]-imidazolidin-2-one-acetate The product is isolated in the form of the acetate.

Melting point: 220° C. (decomp.); $R_f$ value: 0.34 (Reversed Phase Silica gel; methanol/5% aqueous saline solution=6:4); Calculated: C 55.60 H 6.28 N 12.47 S 5.71; Found: 55.64 6.26 12.31 5.61

(12) 1-(4-amidinophenyl)-3-[4-[2-(n-hexanoylamino)-2-(methoxycarbonyl)-ethyl]phenyl]-imidazolidin-2-one-hydrochloride

(13) 1-(4-amidinophenyl)-3-[4-[2-(methoxycarbonyl)-2-(3-phenyl propionylamino)-ethyl]phenyl]-imidazolidin-2-one-hydrochloride

(14) 1-(4-amidinophenyl)-3-[4-[2-(benzylsulfonylamino)-2-(methoxycarbonyl)-ethyl]phenyl]-imidazolidin-2-one-hydrochloride

(15) 1-(4-amidinophenyl)-3-[4-[2-(methoxycarbonyl)ethyl]phenyl]-imidazolidin-2-one-hydrochloride $R_f$ value: 0.45 (Reversed Phase Silica gel; methanol/5% aqueous saline solution=3:2); Calculated: C 59.63 H 5.75 N 13.91 Cl 8.80; Found: 59.59 5.85 13.70 8.55

(16) 2-(4-amidinophenyl)-4-[4-[2-(methoxycarbonyl)ethyl]phenyl]-5-methyl-4H-1,2,4-triazol-3-one-acetate The product is isolated in the form of the acetate.

$R_f$ value: 0.32 (Reversed Phase Silica gel; methanol/5% aqueous saline solution=3:2); Calculated: C 59.59 H 5.69 N 15.79; Found: 59.79 5.72 16.01

(17) 2-(4-amidinophenyl)-4-[4-[2-(methoxycarbonyl)ethyl]phenyl]-5-trifluoromethyl-4H-1,2,4-triazol-3-one-hydrochloride $R_f$ value: 0.37 (Reversed Phase Silica gel; methanol/5% aqueous saline solution=3:2)

EXAMPLE 3

2-(4-Cyanophenyl)-4-[4-(1-ethoxycarbonyl-2-propyl)-phenyl]-5-methyl-4H-1,2,4-triazol-3-one 6.5 g of 1-acetyl-2-(4-cyanophenyl)-4-[4-(1-ethoxycarbonyl-2-propyl)phenyl]-semicarbazide are heated for 1.5 hours in vacuo in an oil bath pre-heated to 200° C. After cooling, the reaction mixture is purified by chromatography over a silica gel column using methylene chloride/ethyl acetate/cyclohexane (20:1:1).

Yield: 3.2g (51% of theory);

Melting point: 134°–138° C.; $R_f$ value: 0.51 (Silica gel; methylene chloride/ethyl acetate/cyclohexane=20:1:1);

The following compounds are obtained analogously to Example 3:

(1) 2-(4-cyanophenyl)-4-[4-(2-ethoxycarbonyl-1-propyl)phenyl]-5-methyl-4H-1,2,4-triazol-3-one Melting point: 124°–128° C.; $R_f$ value: 0.77 (Silica gel; methylene chloride/ethyl acetate=20:1)

(2) 2-(4-cyanophenyl)-4-[cis-4-[2-(methoxycarbonyl)ethyl]-cyclohexyl]-5-methyl-4H-1,2,4-triazol-3-one Melting point: 92°–96° C.; $R_f$ value: 0.60 (Silica gel; methylene chloride/ethyl acetate=9:1)

(3) 2-(4-cyanophenyl)-4-[trans-4-[2-(methoxycarbonyl)ethyl]-cyclohexyl]-5-methyl-4H-1,2,4-triazol-3-one Melting point: 166°–167° C.; $R_f$ value: 0.55 (Silica gel; methylene chloride/ethyl acetate=9:1)

(4) 2-(4-cyanophenyl)-4-[3-[2-(methoxycarbonyl)ethyl]-phenyl]-5-methyl-4H-1,2,4-triazol-3-one Melting point: 134°–137° C.; $R_f$ value: 0.67 (Silica gel; methylene chloride/ethyl acetate=9:1)

(5) 2-(4-cyanophenyl)-4-[4-[2-(methoxycarbonyl)ethyl]-phenyl]-5-phenyl-4H-1,2,4-triazol-3-one Melting point: 190°–194° C.; $R_f$ value: 0.80 (Silica gel; methylene chloride/ethyl acetate=20:1); Calculated: C 70.74 H 4.75 N 13.20; Found: 70.61 4.81 13.41

(6) 2-(4-cyanophenyl)-4-[trans-4-[2-(methoxycarbonyl)ethyl]-cyclohexyl]-4H-1,2,4-triazol-3-one Melting point: 152°–153° C.

(7) 2-(4-cyanophenyl)-4-[4-[2-(methoxycarbonyl)-1-pentyl]-phenyl]-5-methyl-4H-1,2,4-triazol-3-one (8) 2-(4-cyanophenyl)-4-[4-[2-(methoxycarbonyl)ethyl]-phenyl]-5-methyl-4H-1,2,4-triazol-3-one Melting point: 162°–165° C.

(9) 2-(4-cyanophenyl)-4-[4-[2-(methoxycarbonyl)ethyl]-phenyl]-5-trifluoromethyl-4H-1,2,4-triazol-3-one Carried out in boiling trifluoroacetic acid.

$R_f$ value: 0.46 (Silica gel; cyclohexane/ethyl acetate=2:1)

EXAMPLE 4

2-(4-Amidinophenyl)-4-[cis-4-(2-carboxyethyl)cyclohexyl]-5-methyl-4H-1,2,4-triazol-3-one To a solution of 400 mg of 2-(4-amidinophenyl)-4-[cis-4-[2-(methoxycarbonyl)ethyl]cyclohexyl]-5-methyl-4H-1,2,4-triazol-3-one×1.2 hydrogen chloride×1 water in 4 ml of methanol are added 0.71 ml of 4N sodium hydroxide solution and the mixture is stirred for 4 hours at ambient temperature. Then 178 mg of ammonium chloride are added and the mixture is stirred for 1 hour. The precipitate is suction filtered, washed with a little cold methanol and dried at 50° C. in vacuo.

Yield: 230 mg (65% of theory); $R_f$ value: 0.50 (Reversed Phase Silica gel; methanol/5% aqueous saline solution=6:4); Calculated: C 61.44 H 6.78 N 18.85; Found: 61.21 6.87 18.76

The following compounds are obtained analogously to Example 4:

(1) 2-(4-amidinophenyl)-4-[trans-4-(2-carboxyethyl)cyclohexyl]-5-methyl-4H-1, 2, 4-triazol-3-one $R_f$ value: 0.50 (Reversed Phase Silica gel; methanol/5% aqueous saline solution=6:4); Calculated: C 61.44 H 6.78 N 18.55; Found: 61.38 6.93 18.66

(2) 1-(4-amidinophenyl)-3-[trans-4-(2-carboxyethyl)cyclohexyl]-imidazolidin-2-one×0.4 $H_2O$ $R_f$ value: 0.64 (Reversed Phase Silica gel; methanol/10% aqueous saline solution=3:1); Calculated: C 62.41 H 7.39 N 15.32; Found: 62.50 7.37 15.00

(3) 1-(4-amidinophenyl)-3-[cis-4-(2-carboxyethyl)cyclohexyl]-imidazolidin-2-one×0.25 water $R_f$ value: 0.64 (Reversed Phase Silica gel; methanol/10% aqueous saline solution=3:1); Calculated: C 62.88 H 7.36 N 15.44; Found: 63.00 7.32 15.19

(4) 2-(4-amidinophenyl)-4-[trans-4-(2-carboxyethyl)-cyclohexyl]-4H-1,2, 4-triazol-3-one $R_f$ value: 0.44 (Reversed Phase Silica gel; methanol/5% aqueous saline solution=6:4)

(5) 1-[4-(aminomethyl)cyclohexyl]-3-[4-(2-carboxyethyl)phenyl]-imidazolidin-2-one $R_f$ value: 0.55 (Reversed Phase Silica gel; methanol/5% aqueous saline solution=6:4)

(6) 1-[4-[2-(n-butylsulfonylamino)-2-carboxy-ethyl]phenyl]-3-(4-cyanophenyl)-imidazolidin-2-one Worked up with hydrochloric acid.

$R_f$ value: 0.36 (Silica gel; toluene/dioxane/ethanol/glacial acetic acid=90:10:10:6); Calculated: C 58.71 H 5.57 N 11.91; Found: 58.73 5.69 11.82

(7) 2-[4-(benzyloxycarbonylamidino)phenyl]-4-[4-(2-carboxyethyl)phenyl]-5-methyl-4H-1,2,4-triazol-3-one (8) 2-(4-amidinophenyl)-4-[4-(2-carboxyethyl)phenyl]-5-methyl-4H-1,2,4-triazol-3-one $R_f$ value: 0.61 (Reversed Phase Silica gel; methanol/5% aqueous saline solution=3:2); Calculated: C 62.46 H 5.24 N 19.17; Cound: 62.21 5.33 19.39

(9) 2-(4-amidinophenyl)-4-[4-(2-carboxyethyl)phenyl]-5-trifluoromethyl-4H-1 ,2,4-triazol-3-one $R_f$ value: 0.52 (Reversed Phase Silica gel; methanol/5% aqueous saline solution=6:4); Calculated: C 54.42 H 3.85 N 16.70; Found: 54.29 3.86 17.06

(10) 1-[4-(2-carboxyethyl)phenyl]-2-cyanimino-3-[2-(4-piperidinyl)ethyl]-imidazolidine×0.95 HCl×0.3 $H_2O$ $R_f$ value: 0.44 (Reversed Phase Silica gel; methanol/5% aqueous saline solution=6:4); Calculated: C 58.52 H 7.24 N 17.06 Cl 8.21; Found: 58.84 7.05 16.89 8.05

(11) 1-[4-(2-carboxyethyl)phenyl]-3-[2-(4-piperidinyl)ethyl]-4,5-dimethyl-3H-imidazol-2-one-hydrochloride $R_f$ value: 0.43 (Reversed Phase Silica gel; methanol/5% aqueous saline solution=6:4)

(12) 1-[(4-carboxy-1-piperidinyl)carbonylmethyl]-3-[2-(4-piperidinyl)ethyl-imidazolidin-2-one $R_f$ value: 0.71 (Reversed Phase Silica gel; methanol/5% aqueous saline solution=6:4); Mass spectrum: $M^+$=366

(13) 1-[4-(2-carboxyethenyl)-2-fluoro-phenyl]-3-[2-(4-piperidinyl)ethyl]-imidazolidin-2-one×1.1 HCl×1 $H_2O$ Melting point: 253°–255° C. (decomp.); Calculated: C 54.39 H 6.51 N 10.02 Cl 9.29; Found: 54.15 6.43 10.03 9.02

(14) 1-(trans-4-carboxycyclohexyl)-3-[4-(1-benzyloxycarbonyl-4-piperidinyl)phenyl]-imidazolidin-2-one Melting point: 194°–195° C. $R_f$ value: 0.54 (Silica gel; methylene chloride/methanol=9:1)

(15) 1-(2-carboxy-6-naphthyl)-3-[2-(4-piperidinyl)ethyl]-imidazolidin-2-one×0.9 HCl×1 $H_2O$ $R_f$ value: 0.36 (Reversed Phase Silica gel; methanol/5% aqueous saline solution=6:4); Calculated: C 60.25 H 6.72 N 10.05 Cl 7.62; Found: 60.15 6.69 10.11 7.77; Mass spectrum: $M^+$=367

EXAMPLE 5

2-(4-Amidinophenyl)-4-[cis-4-[2-(methoxycarbonyl)ethyl]-cyclohexyl]-5-methyl-4H-1,2,4-triazol-3-one×1.2 hydrogen chloride×1 water 0.9 g of 2-(4-cyanophenyl)-4-[cis-4-[2-(methoxycarbonyl)ethyl]-cyclohexyl]-5-methyl-4H-1,2,4-triazol-3-one in 10 ml of dry methanol are added to 30 ml of dry methanol which has been saturated with hydrochloric acid gas. The mixture is saturated with hydrochloric acid gas at 0° C. and left to stand overnight at ambient temperature. It is evaporated to dryness, mixed with dry methanol and evaporated down once more. The residue is taken up in 20 ml of methanol and mixed with 10 ml of concentrated aqueous ammonia and stirred overnight at ambient temperature. It is evaporated to dryness and the residue is purified by chromatography over a silica gel column using methylene chloride/methanol (6:1).

Yield: 600 mg (60% of theory); $R_f$ value: 0.37 (Reversed Phase Silica gel; methanol/5% aqueous saline solution=6:4); Calculated: C 53.71 H 6.80 N 15.65 Cl 9.51; Found: 53.74 6.87 15.78 9.01

The following compounds are obtained analogously to Example 5:

(1) 2-(4-amidinophenyl)-4-[trans-4-[2-(methoxycarbonyl)ethyl]cyclohexyl]-5-methyl-4H-1,2,4-triazol-3-one×1.1 hydrogen chloride×0.3 water $R_f$ value: 0.37 (Reversed Phase Silica gel; methanol/5% aqueous saline solution=6:4); Calculated: C 55.12 H 6.63 N 16.07 Cl 8.95; Found: 55.33 6.74 15.97 8.88

(2) 2-(4-amidinophenyl)-4-[3-(2-carboxyethyl)phenyl]-5-methyl-4H-1,2,4-triazol-3-one (amidino acid obtained directly)

$R_f$ value: 0.62 (Reversed Phase Silica gel; methanol/5% aqueous saline solution=6:4)

EXAMPLE 6

2-(4-Amidinophenyl)-4-[4-[2-(ethoxycarbonyl)ethyl]phenyl]-5-methyl-4H-1,2,4-triazol-3-one-hydrochloride 750 mg of 2-(4-amidinophenyl)-4-[4-(2-carboxyethyl)-phenyl]-5-methyl-4H-1,2,4-triazol-3-one are stirred for 3 hours in ethanolic hydrochloric acid. The reaction mixture is evaporated down, mixed with toluene and evaporated down once more. This procedure is repeated several times, then the residue is stirred with acetone, the product is suction filtered and washed with acetone.

Yield: 770 mg (87% of theory);

Melting point: 279°–283° C. (decomp.); $R_f$ value: 0.39 (Reversed Phase Silica gel; methanol/5% aqueous saline solution=6:4)

The following compounds are obtained analogously to Example 6:

(1) 2-(4-amidinophenyl)-4-[4-[2-[(3-pentyl)oxycarbonyl]-ethyl]phenyl]-5-methyl-4H-1,2,4-triazol-3-one-hydrochloride $R_f$ value: 0.27 (Reversed Phase Silica gel; methanol/5% aqueous saline solution=6:4)

(2) 2-(4-amidinophenyl)-4-[4-[2-(neopentyloxycarbonyl)-ethyl]-phenyl]-5-methyl-4H-1,2,4-triazol-3-one-hydrochloride Melting point: 295°–297° C. (decomp.); $R_f$ value: 0.25 (Reversed Phase Silica gel; methanol/5% aqueous saline solution=6:4)

(3) 2-(4-amidinophenyl)-4-[4-[2-(isopropyloxycarbonyl)-ethyl]-phenyl]-5-trifluoromethyl-4H-1,2,4-triazol-3-one-hydrochloride Melting point: 319°–320° C.; $R_f$ value: 0.30 (Reversed Phase Silica gel; methanol/5% aqueous saline solution=6:4)

(4) 2-(4-amidinophenyl)-4-[trans-4-[2-(isopropyloxy-carbonyl)-ethyl]cyclohexyl]-5-methyl-4H-1,2,4-triazol-3-one-hydrochloride $R_f$ value: 0.29 (Reversed Phase Silica gel; methanol/5% aqueous saline solution=6:4)

(5) 2-(4-amidinophenyl)-4-[cis-4-[2-(isopropyloxy-carbonyl)-ethyl]cyclohexyl]-5-methyl-4H-1,2,4-triazol-3-one-hydrochloride $R_f$ value: 0.29 (Reversed Phase Silica gel; methanol/5% aqueous saline solution=6:4)

(6) 1-(4-amidinophenyl)-3-[trans-4-[2-(isopropyloxy-carbonyl)-ethyl]cyclohexyl]-imidazolidin-2-one-hydrochloride $R_f$ value: 0.52 (Reversed Phase Silica gel; methanol/10% aqueous saline solution=3:1)

(7) 1-(4-amidinophenyl)-3-[trans-4-[2-(ethyloxycarbonyl)-ethyl]cyclohexyl]-imidazolidin-2-one-hydrochloride×0.5 water $R_f$ value: 0.55 (Reversed Phase Silica gel; methanol/10% aqueous saline solution=3:1); Calculated: C 58.39 .H 7.47 N 12.97; Found: 58.58 7.41 12.94

(8) 1-(4-amidinophenyl)-3-[cis-4-[2-(isopropyloxy-carbonyl)-ethyl]cyclohexyl]-imidazolidin-2-one×1.05 hydrogen chloride×0.2 water $R_f$ value: 0.52 (Reversed Phase Silica gel; methanol/10% aqueous saline solution=3:1); Calculated: C 59.72 H 7.62 N 12.66 Cl 8.41; Found: 59.81 7.67 12.83 8.59

(9) 1-(4-amidinophenyl)-3-[cis-4-[2-(ethoxycarbonyl)ethyl]-cyclohexyl]-imidazolidin-2-one×1.1 hydrogen chloride× 0.5 water $R_f$ value: 0.55 (Reversed Phase Silica gel; methanol/10% aqueous saline solution=3:1); Calculated: C 58.14 H 7.45 N 12.91 Cl 8.99; Found: 58.37 7.39 13.08 9.03

(10) 4-[4-[2-(methoxycarbonyl)ethyl]phenyl]-5-methyl-2-[2-(1-methyl-4-piperidinyl)ethyl]-4H-1,2,4-triazol-3-one-hydrochloride

(11) 1-[4-[2-(methoxycarbonyl)ethyl]cyclohexyl]-3-[2-(4-piperidinyl)ethyl]-imidazolidin-2-one-hydrochloride

(12) 1-[trans-4-(methoxycarbonyl)cyclohexyl]-3-[4-(4-piperidinyl)phenyl]-imidazolidin-2-one-hydrochloride Using thionyl chloride instead of hydrochloric acid gas.

$R_f$ value: 0.38 (Reversed Phase Silica gel; methanol/10% aqueous saline solution=6:4); Mass spectrum: M$^+$=385

(13) 1-[4-(methoxycarbonyl)butyl]-3-[4-(4-piperidinyl)phenyl]-imidazolidin-2-one-hydrochloride

(14) 2-(4-amidinophenyl)-4-[4-[2-(cyclohexyloxycarbonyl)-ethyl]phenyl]- 5-methyl-4H-1,2,4-triazol-3-one-hydrochloride $R_f$ value: 0.16 (Reversed Phase Silica gel; methanol/5% aqueous saline solution=6:4); Calculated: C 62.04 H 6.25 N 14.47 Cl 7.33; Found: 61.87 6.24 14.50 7.60

(15) 2-(4-amidinophenyl)-4-[4-[2-(cyclohexylmethyloxycarbonyl)ethyl]phenyl]-5-methyl-4H-1,2,4-triazol-3-one-hydrochloride Melting point: 273°–275° C. (decomp.) $R_f$ value: 0.10 (Reversed Phase Silica gel; methanol/5% aqueous saline solution=6:4); Calculated: C 62.70 H 6.48 N 14.06 Cl 7.12; Found: 62.43 6.61 14.00 7.27

(16) 2-(4-amidinophenyl)-4-[4-[2-(cyclopentyloxycar-bonyl)-ethyl]phenyl]-5-methyl-4H-1,2,4-triazol-3-one-hydrochloride $R_f$ value: 0.22 (Reversed Phase Silica gel; methanol/5% aqueous saline solution=6:4); Calculated: C 61.34 H 6.01 N 14.90 Cl 7.54; Found: 61.13 6.03 14.79 7.84

(17) 2-(4-amidinophenyl)-4-[4-[2-(cycloheptyloxycar-bonyl)-ethyl]phenyl]-5-methyl-4H-1,2,4-triazol-3-one-hydrochloride

(18) 2-(4-amidinophenyl)-4-[4-[2-(cyclooctyloxycarbonyl)-ethyl]phenyl]-5-methyl-4H-1,2,4-triazole-3-one-hydrochloride

(19) 2-(4-amidinophenyl)-4-[4-[2-[(2-cyclohexylethyl) oxycarbonyl]ethyl]phenyl]-5-methyl-4H-1,2,4-triazol-3-one-hydrochloride

(20) 2-(4-amidinophenyl)-4-[4-(2-((cyclopentylmethyl) oxycarbonyl]ethyl]phenyl]-5-methyl-4H-1,2,4-triazol-3-one-hydrochloride

(21) 2-(4-amidinophenyl)-4-[4-[2-[(4-methylcyclohexyl) oxycarbonyl]ethyl]phenyl]-5-methyl-4H-1,2,4-triazol-3-one-hydrochloride

(22) 2-(4-amidinophenyl)-4-[4-[2-[(3,5-dimethylcyclohexyl)oxycarbonyl]ethyl]phenyl]-5-methyl-4H-1,2,4-triazol-3-one-hydrochloride

(23) 2-(4-amidinophenyl)-4-[4-[2-[(4-ethylcyclohexyl) oxycarbonyl]ethyl)phenyl]-5-methyl-4H-1,2,4-triazol-3-one-hydrochloride

(24) 2-(4-amidinophenyl)-4-[4-[2-(menthyloxycarbonyl) ethyl]-phenyl]-5-methyl-4H-1,2,4-triazol-3-one-hydrochloride

(25) 2-(4-amidinophenyl)-4-[4-[2-[(4-methoxycyclohexyl) oxycarbonyl]ethyl]phenyl]-5-methyl-4H-1,2,4-triazol-3-one-hydrochloride

(26) 2-(4-amidinophenyl)-4-[4-[2-[(2-norbornyl) oxycarbonyl]-ethyl]phenyl]-5-methyl-4H-1,2,4-triazol-3-one-hydrochloride

(27) 2-(4-amidinophenyl)-4-[4-[2-[(3-pinanyl)oxycarbonyl] -ethyl]phenyl]-5-methyl-4H-1,2,4-triazol-3-one-hydrochloride

(28) 2-(4-amidinophenyl)-4-[4-[2-(fenchyloxycarbonyl) ethyl]-phenyl]-5-methyl-4H-1,2,4-triazol-3-one-hydrochloride

(29) 2-(4-amidinophenyl)-4-[4-[(2-indanyl)oxycarbonyl) ethyl]-phenyl]-5-methyl-4H-1,2,4-triazol-3-one-hydrochloride

(30) 2-(4-amidinophenyl)-4-[4-[2-(isopropyloxycarbonyl)-1-propyl]phenyl]-5-methyl-4H-1,2,4-triazol-3-one-hydrochloride Melting point: 260°–262° C.; $R_f$ value: 0.36 (Reversed Phase Silica gel; methanol/5% aqueous saline solution=6:4)

(31) 2-(4-amidinophenyl)-4-[4-[2-(isopropyloxycarbonyl) ethyl]phenyl]-5-phenyl-4H-1,2,4-triazol-3-one-hydrochloride Melting point: 295°–297° C.; $R_f$ value: 0.24 (Reversed Phase Silica gel; methanol/5% aqueous saline solution=6:4)

(32) 1-[4-[2-(cyclohexyloxycarbonyl)ethyl]phenyl]-3-[2-(4-piperidinyl)ethyl]-imidazolidin-2-one-hydrochloride×H$_2$O Melting point: 185°–188° C.; $R_f$ value: 0.24 (Reversed Phase Silica gel; methanol/5% aqueous saline solution=6:4); Calculated: C 62.29 H 8.36 N 8.72 Cl 7.35; Found: 62.34 8.38 8.74 8.04

(33) 1-[2-(4-piperidinyl)ethyl]-3-[4-[2-(isopropyloxycarbonyl)ethyl]phenyl]-imidazolidin-2-one-hydrochloride Melting point: 185°–188° C.; $R_f$ value: 0.32 (Reversed Phase Silica gel; methanol/5% aqueous saline solution=6:4); Calculated: C 62.32 H 8.08 N 9.91 Cl 8.36; Found: 62.10 8.04 9.96 8.20

(34) 1-[4-[2-(ethoxycarbonyl)ethyl]phenyl]-3-(2-(4-piperidinyl)ethyl]-imidazolidin-2-one-hydrochloride Using thionyl chloride instead of hydrochloric acid gas.

Melting point: 177°–180° C.; $R_f$ value: 0.33 (Reversed Phase Silica gel; methanol/5% aqueous saline solution=6:4); Calculated: C 61.53 H 7.87 N 10.25 Cl 8.65; Found: 61.30 7.92 10.28 8.83

(35) 1-[trans-4-[2-(ethoxycarbonyl)ethyl]cyclohexyl]-3-[2-(4-piperidinyl)ethyl]-imidazolidin-2-one-hydrochloride Using thionyl chloride instead of hydrochloric acid gas.

Melting point: 188°–196° C.; $R_f$ value: 0.34 (Reversed Phase Silica gel; methanol/5% aqueous saline solution=6:4); Calculated: C 60.63 H 9.21 N 10.10 Cl 8.52; Found: 60.32 9.17 9.99 8.79

(36) 1-[trans-4-[2-(isopropyloxycarbonyl)ethyl]cyclohexyl] -3-(2-(4-piperidinyl)ethyl]-imidazolidin-2-one×1.05 HCl Using thionyl chloride instead of hydrochloric acid gas.

Melting point: 194°–199° C.; $R_f$ value: 0.26 (Reversed Phase Silica gel; methanol/5% aqueous saline solution=6:4); Calculated: C 61.15 H 9.39 N 9.73 Cl 8.67; Found: 61.00 9.33 9.77 8.75

(37) 1-[2-(4-quinuclidinyl)ethyl]-3-[4-[2-(ethoxycarbonyl)-ethyl]phenyl]-imidazolidin-2-one-hydro-chloride Using thionyl chloride instead of hydrochloric acid gas.

Melting point: 217°–220° C.; $R_f$ value: 0.29 (Reversed Phase Silica gel; methanol/5% aqueous saline solution=6:4)

(38) 1-[2-(4-quinuclidinyl)ethyl]-3-[4-[2-(isopropyloxycarbonyl)ethyl]phenyl]-imidazolidin-2-one-hydrochloride Using thionyl chloride instead of hydrochloric acid gas.

$R_f$ value: 0.25 (Reversed Phase Silica gel; methanol/5% aqueous saline solution=6:4)

(39) 1-[4-(4-cyano-4-piperidinyl)phenyl]-3-[trans-4-(methoxycarbonyl)cyclohexyl]-imidazolidin-2-one-hydrochloride×H$_2$O Melting point: >240° C.; $R_f$ value: 0.54 (Reversed Phase Silica gel; methanol/5% aqueous saline solution=6:4); Calculated: C 59.41 H 7.15 N 12.05 Cl 7.62; Found: 59.71 7.21 11.95 7.94; Mass spectrum: M$^+$=410

(40) 1-[trans-4-(ethoxycarbonyl)cyclohexyl]-3-[4-(4-piperidinyl)phenyl]-imidazolidin-2-one-hydrochloride Using thionyl chloride instead of hydrochloric acid gas.

$R_f$ value, 0.39 (Reversed Phase Silica gel; methanol/5% aqueous saline solution=6:4); Calculated: C 63.36 H 7.86 N 9.64 Cl 8.13; Found: 62.91 7.86 9.62 8.65

(41) 1-[4-(4-quinuclidinyl)phenyl]-3-[trans-4-(ethoxycarbonyl)cyclohexyl]-imidazolidin-2-one-hydrochloride×0.5 H$_2$O $R_f$ value: 0.27 (Reversed Phase Silica gel; methanol/5% aqueous saline solution=6:4); Calculated: C 63.75 H 7.92 N 8.92 Cl 7.52; Found: 63.69 7.93 8.82 7.38; Mass spectrum: M$^+$=425

(42) 1-[trans-4-(ethoxycarbonyl)cyclohexyl]-3-[4-(4-piperidinyl)phenyl]-3H-imidazol-2-one-hydrochloride Melting point: 260°–270° C.; $R_f$ value: 0.50 (Reversed Phase Silica gel; methanol/5% aqueous saline solution=6:4); Calculated: C 63.65 H 7.43 N 9.68; Found: 63.31 7.53 9.58; Mass.spectrum: M$^+$=397

(43) 1-[trans-4-(ethoxycarbonyl)cyclohexyl]-3-[4-(4-methyl-4-piperidinyl)phenyl]-imidazolidin-2-one-hydrochloride $R_f$ value: 0.43 (Reversed Phase Silica gel; methanol/5% aqueous saline solution=6:4); Calculated: C 64.05 H 8.06 N 9.34 Cl 7.88; Found: 63.80 8.28 9.24 7.89

EXAMPLE 7

1-(4-Amidinophenyl)-3-[trans-4-[2-(methoxycarbonyl) ethyl]cyclohexyl]-imidazolidin-2-one-hydrochloride 1.1 g of 1-(4-amidinophenyl) -3-[trans-4-[2-(methoxycarbonyl)-ethyl]cyclohexyl]-3H-imidazol-2-one-hydrochloride in 55 ml of methanol are hydrogenated for 3 hours with 1 g of palladium on activated charcoal at ambient temperature under a hydrogen pressure of 51 psi. The catalyst is removed by suction filtering, the filtrate is evaporated down and the residue is stirred with methylene chloride. The product is suction filtered and dried.

Yield: 870 mg (79% of theory); $R_f$ value: 0.52 (Reversed Phase Silica gel; methanol/10% aqueous saline solution= 3:1); Calculated: C 58.74 H 7.15 N 13.70; Found: 58.54 7.31 13.53

The following compounds are obtained analogously to Example 7:

(1) 1-(4-amidinophenyl)-3-[cis-4-[2-(methoxycarbonyl)ethyl]-cyclohexyl]-imidazolidin-2-one-hydrochloride×1 water $R_f$ value: 0.52 (Reversed Phase Silica gel; methanol/10% aqueous saline solution=3:1); Calculated: C 56.27 H 7.32 N 13.12; Found: 56.46 7.16 13.45

(2) 1-[2-(1-tert.butyloxycarbonyl-4-piperidinyl)ethyl]-3-[trans-4-[2-(methoxycarbonyl)ethyl]cyclohexyl] imidazolidin-2-one Melting point: 92°–94° C.; $R_f$ value: 0.58 (Silica gel; ethyl acetate)

(3) 1-[2-(1-tert.butyloxycarbonyl-4-piperidinyl)ethyl]-3-[4-[2-(methoxycarbonyl)ethyl]phenyl]-cis-4,5-dimethylimidazolidin-2-one Carried out in ethyl acetate at 80° C.

Rf value: 0.51 (Silica gel; cyclohexane/ethyl acetate=1:1)

(4) 1-[2-(methoxycarbonyl)-6-naphthyl]-3-[2-(4-piperidinyl)ethyl]-imidazolidin-2-one-hydrochloride Carried out in methanol/aqueous hydrochloric acid Rf value: 0.25 (Reversed Phase Silica gel; methanol/5% aqueous saline solution=6:4)

(5) 1-[2-(methoxycarbonyl-1,2,3,4-tetrahydro-6-naphthyl]-3-[2-(4-piperidinyl)ethyl]-imidazolidin-2-one-hydrochloride Carried out in methanol/aqueous hydrochloric acid $R_f$ value: 0.50 (Silica gel; methylene chloride/methanol/conc. aqueous ammonia=5:1:0.2)

(6) 1-[trans-4-(methoxycarbonyl)cyclohexyl]-3-[4-(1-trifluoroacetyl-4-piperidinyl)phenyl]-imidazolidin-2-one Melting point: 183°–185° C.; $R_f$ value: 0.59 (Silica gel; cyclohexane/ethyl acetate=2:3)

(7) 1-[trans-4-(methoxycarbonyl)cyclohexyl]3-[4-(4-quinuclidinyl)phenyl]-imidazolidin-2-one-hydrochloride Carried out in methanol/aqueous hydrochloric acid R value: 0.38 (Reversed Phase Silica gel; methanol/5% aqueous saline solution=6:4)

(8) 1-[trans-4-(methoxycarbonyl)cyclohexyl]-3-[4-(4-methyl-1-trifluoroacetyl-4-piperidinyl)phenyl]-imidazolidin-2-one Carried out in ethyl acetate Melting point: 158°–161° C.; $R_f$ value: 0.50 (Silica gel; cyclohexane/ethyl acetate=1:1)

(9) 1-[2-(1-tert.butyloxycarbonyl-4-piperidinyl)ethyl]-3-[trans-4-[[(methoxycarbonyl)methyl]oxy]cyclohexyl]-imidazolidin-2-one $R_f$ value: 0.42 (Silica gel; ethyl acetate)

EXAMPLE 8

1-(4-Cyanophenyl)-3-[trans-4-[2-(methoxycarbonyl)ethyl]-cyclohexyl]-3H-imidazol-2-one 6.8 g of 4-[(2,2-diethoxyethyl)amino]benzonitrile (melting point: 75°–78° C., prepared from 4-aminobenzonitrile by reacting with bromoacetaldehyde-diethylacetal in the presence of N-ethyl-diisopropylamine) and 6.81 g of [trans-4-[2-(methoxycarbonyl)-ethyl]cyclohexyl]-isocyanate (prepared from the corresponding amine hydrochloride by reacting with phosgene) are stirred for 8 hours at 65° C. and then for 2 hours at 100° C. After cooling, the reaction mixture is purified by chromatography over a silica gel column using cyclohexane/ethyl acetate (1:1). The product is stirred overnight in a mixture of 15 ml of dioxane and 10 ml of 2N hydrochloric acid. The precipitate is suction filtered and dried.

Yield: 1.9 g (19% of theory); Melting point: 136°–142° C.

The following compounds are obtained analogously to Example 8:

(1) 1-(4-cyanophenyl)-3-[cis-4-[2-(methoxycarbonyl)ethyl]-cyclohexyl]-3H-imidazol-2-one $R_f$ value: 0.40 (Silica gel; cyclohexane/ethyl acetate=1:1)

(2) 1-[2-(1-tert.butyloxycarbonyl-4-piperidinyl)ethyl]-3-[trans-4-[2-(methoxycarbonyl)ethyl]cyclohexyl]-3H-imidazol-2-one The N-[2-(1-tert.butyloxycarbonyl-4-piperidinyl)-ethyl]-N-(2,2-diethoxyethyl)-amine used as amine is obtained by reacting 1-tert.butyloxycarbonyl-4-[2-(methanesulfonyloxy)ethyl]-piperidine with aminoacetaldehyde- diethylacetal. The urea formation is carried out at ambient temperature, cyclisation by dry heating to 145° C.

$R_f$ value: 0.34 (Silica gel; ethyl acetate)

(3) 1-[trans-4-(methoxycarbonyl)cyclohexyl]-3-[4-(1-trifluoroacetyl-4-piperidinyl)phenyl]-3H-imidazol-2-one The N-(2,2-diethoxyethyl)-4-(1-trifluoroacetyl-4-piperidinyl)-aniline use as amine [$R_f$ value: 0.90 (silica gel; cyclohexane/ethyl acetate=1:3] is obtained by reacting 4-(1-trifluoroacetyl-4- piperidinyl)-aniline with bromoacetaldehyde-diethylacetal in the presence of N-ethyl-diisopropylamine. The trans-4-(methoxycarbonyl) cyclohexyl-isocyanate used as isocyanate is obtained from the corresponding amine-hydrochloride by reacting with phosgene. Urea formation carried out at 100° C., cyclisation by dry heating to 125° C.

Melting point: 178°–179° C. $R_f$ value: 0.36 (silica gel; cyclohexane/ethyl acetate=2:3)

(4) 1-[2-(1-tert.butyloxycarbonyl-4-piperidinyl)ethyl]-3-[trans-4-[[(methoxycarbonyl)-methyl]oxy]cyclohexyl]-3H-imidazol-2-one The trans-4-[[(methoxycarbonyl)methyl]oxy]-cyclohexylisocyanate used as isocyanate is obtained by reaction of the corresponding amine-hydrochloride with phosgene. Urea formation effected at ambient temperature, cyclization by dry heating at 160° C.

EXAMPLE 9

1-(1-Amino-1,2,3,4-tetrahydronaphthalin-6-yl)-3-[4-[2-(methoxycarbonyl)ethyl]phenyl]-imidazolidin-2-one-hydrochloride 2.2 g of 1-(1-hydroxyimino-1,2,3,4-tetrahydronaphthalin-6-yl)-3-[4-[2-(methoxycarbonyl)ethyl phenyl]imidazolidin-2-one, in a mixture of 100 ml of methanol and 5 ml of methanolic hydrochloric acid, are hydrogenated for 5 hours at 50° C. under a hydrogen pressure of 3.4 bar in the presence of 0.3 g of palladium on activated charcoal (10% palladium). The catalyst is suction filtered, the filtrate is evaporated down and the residue is stirred with a little methanol. The product is suction filtered, washed with a little methanol and diethylether and dried.

Yield: 2.1 g (90% of theory); $R_f$ value: 0.73 (silica gel; toluene/dioxane/methanol/conc. aqueous ammonia=20:50:20:5)

EXAMPLE 10

4-[4-[2-(Methoxycarbonyl)ethyl]phenyl]-5-methyl-2-[2-(4-piperidinyl)ethyl]-4H-1,2,4-triazol-3-one-toluene-sulfonate×water 4 ml of trifluoroacetic acid are added to 1.3 g of 2-[2-(1-tert.butyloxycarbonyl-4-piperidinyl)ethyl]-4-[2-(methoxycarbonyl)ethyl]phenyl]-5-methyl-4H-1,2,4-triazol-3-one in 13 ml methylene chloride and the mixture is stirred for 2 hours at ambient temperature. The reaction mixture is evaporated down and the residue is taken up in methylene chloride. It is mixed with ice water, made slightly alkaline with sodium hydroxide solution and the organic phase is separated off. The organic phase is evaporated down, the residue is taken up in acetone and mixed with a solution of 500 mg of p-toluenesulphonic acid-hydrate in acetone. Then diethylether is added, the mixture is stirred whilst cooling with ice and the precipitate is suction filtered and washed with acetone.

Yield: 760 mg (49% of theory); $R_f$ value: 0.19 (silica gel; toluene/dioxane/methanol/conc. aqueous ammonia= 20:50:20:5); Calculated: C 57.63 H 6.81 N 9.96 S 5.70; Found: 57.84 6.77 9.78 6.04

The following compounds are obtained analogously to Example 10:

(1) 1-[4-[2-(methoxycarbonyl)ethyl]phenyl]-3-[2-(4-piperidinyl)ethyl]-imidazolidin-2-one-hydrochloride Isolated as hydrochloride $R_f$ value: 0.38 (Reversed Phase Silica gel; methanol/5% aqueous saline solution=6:4)

(2) 1-[4-[2-(methoxycarbonyl)-1-pentyl]phenyl]-3-[2-(4-piperidinyl)ethyl]-imidazolidin-2-one-hydrochloride (3) 4-[4-[2-(methoxycarbonyl)-1-pentyl]phenyl]-5-methyl-2-[2-(4-piperidinyl)ethyl]-4H-1,2,4-triazol-3-one-hydrochloride×0.5 water Melting point: 132°–140° C.; Calculated: C 60.05 H 7.89 N 12.18 Cl 7.71; Found: 60.04 7.82 12.16 8.25

(4) 4-[4-[2-(methoxycarbonyl)-3-methyl-1-butyl]phenyl]-5-methyl-2-[2-(4-piperidinyl)ethyl]-4H-1,2,4-triazol-3-one-hydrochloride (5) 4-[4-[2-(methoxycarbonyl)-1-butyl]phenyl]-5-methyl-2-[2-(4-piperidinyl)ethyl]-4H-1,2,4-triazol-3-one-hydrochloride (6) 4-[4-[2-(methoxycarbonyl)-1-propyl]phenyl]-5-methyl-2-[2-(4-piperidinyl)ethyl]-4H-1,2,4-triazol-3-one-hydrochloride (7) 1-[4-[2-(methoxycarbonyl)ethyl]phenyl]-3-[2-(4-piperidinyl)ethyl]-3,4,5,6-tetrahydro-1H-pyrimidin-2-one-hydrochloride (8) 4-[4-[2-(methoxycarbonyl)ethyl]phenyl]-5-methyl-2-[(1-piperazinyl)carbonylmethyl]-4H-1,2,4-triazol-3-one-hydrochloride (9) 4-[4-[2-(methoxycarbonyl)ethyl]phenyl]-5-methyl-2-[2-(1-aza-4-cycloheptyl)ethyl]-4H-1,2,4-triazol-3-one-hydrochloride

(10) 4-[4-[2-(methoxycarbonyl)ethyl]phenyl]-5-methyl-2-[2-(1,4-diaza-1-cycloheptyl)ethyl]-4H-1,2,4-triazol-3-one-dihydrochloride

(11) 4-[4-[2-(n-butylsulfonylamino)-2-(methoxycarbonyl)ethyl]phenyl]-5-methyl-2-[2-(4-piperidinyl)ethyl]-4H-1,2,4-triazol-3-one-hydrochloride

(12) 4-[4-[2-(methansulfonylamino)-2-(methoxycarbonyl)ethyl]phenyl]-5-methyl-2-[2-(4-piperidinyl)ethyl]-4H-1,2,4-triazol-3-one-hydrochloride

(13) 4-[4-[2-(acetylamino)-2-(methoxycarbonyl)-ethyl]-phenyl]-5-methyl-2-[2-(4-piperidinyl)ethyl]-4H-1,2,4-triazol-3-one-hydrochloride

(14) 4-[4-[2-(methoxycarbonyl)-1-octyl]phenyl]-5-methyl-2-[2-(4-piperidinyl)ethyl]-4H-1,2,4-triazol-3-one-hydrochloride

(15) 4-[4-[2-(methoxycarbonyl)ethyl]phenyl]-2-[2-(4-piperidinyl)ethyl]-4H-1,2,4-triazol-3-one-hydrochloride×0.5 $H_2O$ Carried out with methanolic hydrochloric acid.

Melting point: 188°–191° C.; $R_f$ value: 0.52 (Reversed Phase Silica gel; methanol/5% aqueous saline solution=6:4); Calculated: C 56.50 H 6.99 N 13.87 Cl 8.78; Found: 56.79 6.93 13.76 8.83

(16) 2-[4-[2-(methoxycarbonyl)ethyl]phenyl]-5-[2-(4-piperidinyl)ethyl]-3,4-dihydro-2H,5H-1,2,5-thiadiazole-1,1-dioxide-hydrochloride Carried out with methanolic hydrochloric acid.

$R_f$ value: 0.63 (Reversed Phase Silica gel; methanol/5% aqueous saline solution=6:4)

(17) 1-[4-[2-(methoxycarbonyl)ethyl]phenyl]-3-[(1-piperazinyl)carbonylmethyl]-imidazolidin-2-one-hydrochloride Carried out with methanolic hydrochloric acid (the compound obtained was directly converted into the compound of Example 1(31)).

(18) 1-[4-[2-(n-butylsulfonylamino)-2-(methoxycarbonyl)-ethyl]phenyl]-3-[2-(4-piperidinyl)ethyl]-imidazolidin-2-one-hydrochloride Carried out with methanolic hydrochloric acid.

Melting point: 208° C. (decomp.); $R_f$ value: 0.43 (Reversed Phase Silica gel; methanol/5% aqueous saline solution=6:4)

(19) 4-[4-[2-(methoxycarbonyl)ethyl]phenyl]-2-[2-(1-piperazinyl)ethyl]-4H-1,2,4-triazol-3-one×2.1 HCl×0.3 $H_2O$ Carried out with methanolic hydrochloric acid.

Melting point: 210°–213° C.; $R_f$ value: 0.61 (Reversed Phase Silica gel; methanol/5% aqueous saline solution=6:4); Calculated: C 48.98 H 6.32 N 15.87 Cl 16.87; Found: 48.96 6.36 15.88 16.99; Mass spectrum: $M^+$=359

(20) 2-cyanimino-1-[4-[2-(methoxycarbonyl)ethyl]phenyl]-3-[2-(4-piperidinyl)ethyl]-imidazolidin×HCl×0.5 $H_2O$ Carried out with trimethyliodosilane in methylene chloride and isolated as the hydrochloride.

Melting point: 162°–165° C.; $R_f$ value: 0.34 (Reversed Phase Silica gel; methanol/5% aqueous saline solution=6:4); Calculated: C 58.80 H 7.28 N 16.33 Cl 8.27; Found: 58.70 7.22 16.18 8.51

(21) 1-[2-(1-aza-4-cycloheptyl)ethyl]-3-[4-[2-(methoxycarbonyl)ethyl]phenyl]-imidazolidin-2-one-hydrochloride× 0.15 water Carried out with methanolic hydrochloric acid.

Melting point: 134°–136° C.; $R_f$ value: 0.38 (Reversed Phase Silica gel; methanol/5% aqueous saline solution=6:4); Calculated: C 61.13 H 7.89 N 10.18 Cl 8.59; Found: 61.18 7.89 10.29 8.38

(22) 1-[trans-4-[2-(methoxycarbonyl)ethyl]cyclohexyl]-3-[2-(4-piperidinyl)ethyl]-imidazolidin-2-one-hydrochloride Carried out with methanolic hydrochloric acid in the presence of tetramethyl orthocarbonate.

Melting point: 190°–195° C. (decomp.); $R_f$ value: 0.36 (Reversed Phase Silica gel; methanol/5% aqueous saline solution=6:4); Calculated: C 59.76 H 9.03 N 10.45 Cl 8.82; Found: 59.47 9.11 10.58 8.84

(23) 3-[4-[2-(methoxycarbonyl)ethyl]phenyl]-1-[2-(4-piperidinyl)ethyl]-hydantoin-hydrochloride Carried out with methanolic hydrochloric acid.

Melting point: 203°–205° C. (decomp.); $R_f$ value: 0.57 (Reversed Phase Silica gel; methanol/5% aqueous saline solution=6:4); Calculated: C 58.60 H 6.88 N 10.25 Cl 8.65; Found: 58.40 6.95 10.14 8.55

(24) 1-[4-[2-(methoxycarbonyl)ethyl]phenyl]-3-[2-(4-piperidinyl)ethyl]-4,5-dimethyl-3H-imidazol-2-one-hydrochloride Carried out with methanolic hydrochloric acid.

$R_f$ value: 0.33 (Reversed Phase Silica gel; methanol/5% aqueous saline solution=6:4)

(25) 1-[4-[2-(methoxycarbonyl)ethyl]phenyl]-3-[2-(4-piperidinyl)ethyl]-cis-4,5-dimethyl-imidazolidin-2-one-hydrochloride Carried out with methanolic hydrochloric acid.

$R_f$ value: 0.30 (Reversed Phase Silica gel; methanol/5% aqueous saline solution=6:4)

(26) 1-[4-[2-(methoxycarbonyl)ethyl]phenyl]-3-[2-(4-piperidinyl)ethyl]-hydantoin-hydrochloride Carried out with methanolic hydrochloric acid.

Melting point: 186°–188° C.; $R_f$ value: 0.41 (Reversed Phase Silica gel; methanol/5% aqueous saline solution=6:4); Calculated: C 58.60 H 6.88 N 10.25 Cl 8.65; Found: 58.27 7.10 10.22 8.70

(27) 1-[4-[2-(methoxycarbonyl)ethyl]phenyl]-3-[2-(4-piperidinyl)ethyl]-3H-benzimidazol-2-one-hydrochloride Carried out with methanolic hydrochloric acid.

$R_f$ value: 0.33 (Reversed Phase Silica gel; methanol/5% aqueous saline solution=6:4)

(28) 1-[4-[2-(o-ethyl-phosphono)ethyl]phenyl]-3-[2-(4-piperidinyl)ethyl]-imidazolidin-2-one×0.9 HCl×1.1 $H_2O$ Carried out with ethanolic hydrochloric acid.

$R_f$ value: 0.42 (Reversed Phase Silica gel; methanol/5% aqueous saline solution=6:4); Calculated: C 51.98 H 7.65 N 9.09 Cl 6.90; Found: 51.74 7.43 9.08 6.51; Mass spectrum: $(M+H)^+=410$

(29) 1-[[4-(ethoxycarbonyl)-1-piperidinyl]carbonyl-methyl]-3-[2-(4-piperidinyl)ethyl]-imidazolidin-2-one-trifluoroacetate $R_f$ value: 0.57 (Reversed Phase Silica gel; methanol/5% aqueous saline solution=6:4)

(30) 1-[4-[2-(methoxycarbonyl)ethenyl]-2-fluoro-phenyl]-3-[2-(4-piperidinyl)ethyl]-imidazolidin-2-one-hydrochloride Carried out with methanolic hydrochloric acid.

Melting point: 175°–180° C.; $R_f$ value: 0.30 (Reversed Phase Silica gel; methanol/5% aqueous saline solution=6:4)

EXAMPLE 11

1-[4-(Aminomethyl)cyclohexyl]-3-[4-[2-(methoxycarbonyl)-ethyl]-phenyl]-imidazolidin-2-one-hydrochloride 500 mg of 1-(4-cyanocyclohexyl)-3-[4-[2-(methoxycarbonyl)ethyl]-phenyl]-3H-imidazol-2-one are hydrogenated in a mixture of 20 ml of methanol and 1 ml of methanolic hydrochloric acid in the presence of 500 mg of palladium on activated charcoal (10% palladium) at ambient temperature under a hydrogen pressure of 5 bar. The catalyst is filtered off and the filtrate is evaporated down. The residue is triturated with acetone, suction filtered and washed with acetone and petroleum ether.

Yield: 110 mg (20% of theory); $R_f$ value: 0.46 (Reversed Phase Silica gel; methanol/5% aqueous saline solution=6:4)

The following compounds are obtained analogously to Example 11:

(1) 2-[4-(aminomethyl)phenyl]-4-[4-[2-(ethoxycarbonyl)-1-propyl]phenyl]-5-methyl-4H-1,2, 4-triazol-3-one-hydrochloride Carried out in ethanol Melting point: 194°–197° C. $R_f$ value: 0.54 (Reversed Phase Silica gel; methanol/10% aqueous saline solution=3:1)

(2) 1-(2-aminomethyl-1,2,3,4-tetrahydro-6-naphthyl)-3-[trans-4-(methoxycarbonyl)cyclohexyl]-imidazolidin-2-one-hydrochloride Melting point: 323°–327° C. (decomp.); $R_f$ value: 0.35 (Reversed Phase Silica gel; methanol/5% aqueous saline solution=6:4)

(3) 1-[4-(aminomethyl-bicyclo[2.2.2]octan-1-yl]-3-[4-[2-(methoxycarbonyl)ethyl]phenyl]-imidazolidin-2-one-hydrochloride Melting point: 303°–306° C. (decomp.); $R_f$ value: 0.27 (Reversed Phase Silica gel; methanol/5% aqueous saline solution=6:4)

(4) 1-(5-aminopentyl)-3-[4-[2-(methoxycarbonyl)ethyl]phenyl]-imidazoldin-2-one-hydrochloride Melting point: 234°–236 C.; Calculated: C 58.45 H 7.63 N 11.36 Cl 9.58; Found: 58.17 7.58 11.50 9.66

(5) 1-[4-[(2-aminoethyl)oxy]phenyl]-3-[trans-4-(methoxycarbonyl)cyclohexyl]-imidazolidin-2-one-hydrochloride Carried out in methanol/0.1N HCl $R_f$ value: 0.47 (Reversed Phase Silica gel; methanol/5% aqueous saline solution=6:4)

EXAMPLE 12

1-(4-Cyanocyclohexyl)-3-[4-[2-(methoxycarbonyl)ethyl]phenyl]-3H-imidazol-2-one 1.8 g of potassium tert.butoxide in 50 ml of tert.butanol are added dropwise at −12° to −16° C. to 2.7 g of 3-[4-[2-(methoxycarbonyl)ethyl]phenyl]-1-(4-oxocyclohexyl)-3H-imidazol-2-one and 2.0 g of p-toluenesulfonyl-methyl-isocyanide in 60 ml of ethyleneglycol dimethylether. After 45 minutes the cooling bath is removed and stirring is continued for a further 2 hours. The reaction mixture is neutralised with hydrochloric acid and then evaporated down. The residue is dissolved in chloroform, washed 3 times with water, dried and the organic phase is evaporated down. The residue is purified by chromatography over a silica gel column using cyclohexane/ethyl acetate (1:1).

Yield: 500 mg (18% of theory); Melting point: 177°–180° C.; $R_f$ value: 0.24 (silica gel; cyclohexane/ethyl acetate=3:7)

EXAMPLE 13

1-(4-Amidinophenyl)-3-[4-[2-(isopropyloxycarbonyl)-ethyl]-phenyl]-imidazolidin-2-one×1.1 hydrogen chloride Hydrochoric gas is introduced into a mixture of 400 mg of 1-(4-amidinophenyl)-3-[4-[2-(methoxycarbonyl)ethyl]phenyl]-imidazolidin-2-one-hydrochloride and 300 ml of isopropanol and then refluxed for 1.5 hours. After cooling, the mixture is evaporated down and the residue is triturated with acetone and suction filtered. The product is washed with acetone and diethylether and dried.

Yield: 400 mg (92% of theory); $R_f$ value: 0.32 (Reversed Phase Silica gel; methanol/5% aqueous saline solution=3:2); Calculated: C 60.80 H 6.29 N 12.89 Cl 8.97; Found: 60.73 6.29 12.86 8.86

The following compounds are obtained analogously to Example 13:

(1) 1-(4-amidinophenyl)-3-[4-[2-(cyclohexyloxycarbonyl)ethyl]phenyl]-imidazolidin-2-one-hydrochloride $R_f$ value: 0.07 (Reversed Phase Silica gel; methanol/5% aqueous saline solution=6:4)

(2) 1-(4-amidinophenyl)-3-[trans-4-[2-(cyclohexyloxycarbonyl)ethyl]cyclohexyl]-imidazolidin-2,4-dione-hydrochloride×cyclohexanol $R_f$ value: 0.11 (Reversed Phase Silica gel; methanol/5% aqueous saline solution=6:4); Calculated: C 62.98 H 8.01 N 9.48 Cl 6.00; Found: 63.05 7.97 9.79 6.40

(3) 2-(4-amidinophenyl)-4-[4-[2-(cyclohexyloxycarbonyl)-1-propyl]phenyl]-5-methyl-4H-1,2,4-triazol-3-one-hydrochloride $R_f$ value: 0.12 (Reversed Phase Silica gel; methanol/5% aqueous saline solution=6:4)

(4) 1-(4-amidinophenyl)-3-[4-[2-(n-butylsulfonylamino)-2-(cyclohexyloxycarbonyl)-ethyl]phenyl]-imidazolidin-2-one-hydrochloride

EXAMPLE 14

1-(4-Cyanophenyl)-3-[trans-4-[2-(methoxycarbonyl)ethyl]cyclohexyl]-imidazolidin-2,4-dione 5.5 g of N-(4-cyanophenyl)-N-(methoxycarbonylmethyl)-N'-[trans-4-[2-(methoxycarbonyl)ethyl]cyclohexyl]-urea are heated to 180° C. for 4.5 hours in vacuo. After cooling, 10 ml of ethyl acetate are added, the mixture is briefly heated to boiling and then cooled in an ice bath. The solid matter is suction filtered and washed with a little ethyl acetate.

Yield: 3.8 g (75% of theory);

Melting point: 207°–208° C., $R_f$ value: 0.75 (Silica gel; methylene chloride/ethyl acetate=3:1)

EXAMPLE 15

1-[4-(2-Carboxyethyl)phenyl]-3-[2-(1-methyl-4-piperidinyl)-ethyll-imidazolidin-2-one×1.1 HCl 900 mg of 1-[4-[2-(methoxycarbonyl)ethyl]phenyl]-3-[2-(4-piperidinyl)ethyl]-imidazolidin-2-one-hydrochloride, 600 mg of formic acid and 250 mg of aqueous formaldehyde solution (37%) are stirred for 4 hours at 70°–80° C. 1.1 ml of 2N sodium hydroxide solution and 0.2.ml of aqueous formaldehyde solution (37%) are added and the mixture is stirred for a further 3 hours at 70°–80C. It is evaporated down, the residue is mixed with 3ml of hydrochloric acid and stirred for 1 hour at 70° C. It is cooled, acetone is added and the precipitate is filtered off. The filtrate is evaporated down and stirred with acetone. The solid substance is suction filtered and dried. The residue is decocted with 70 ml of methylene chloride, then filtered off and the filtrate is evaporated down. This procedure is repeated with 70 ml of chloroform. The combined evaporation residues are stirred with acetone, the solid matter is suction filtered, washed and dried.

Yield: 400 mg (46% of theory); Melting point: 220° C. (decomp.); $R_f$ value: 0.45 (Reversed Phase Silica gel; methanol/5% aqueous saline solution=6:4); Calculated: C 60.12 H 7.59 N 10.52 Cl 9.76; Found: 60.04 7.64 10.30 9.63

The following compounds are obtained analogously to Example 15:
(1) 4-[4-(2-carboxyethyl)phenyl]-5-methyl-2-[2-(1-methyl-4-piperidinyl)ethyl]-4H-1,2,4-triazol-3-one-hydrochloride
(2) 1-(trans-4-carboxycyclohexyl)-3-[4-(1-methyl-4-piperidinyl)phenyl]-imidazolidin-2-one×0.95 HCl×0.5 H$_2$O The reaction is carried out with the carboxylic acid.

$R_f$ value: 0.49 (Reversed Phase Silica gel; methanol/5% aqueous saline solution=6:4); Calculated: C 61.57 H 7.74 N 9.79 Cl 7.84; Found: 61.67 7.77 9.92 7.70

EXAMPLE 16

1-[4-[4-(Methoxycarbonyl)butyl]phenyl]-3-(4-piperidinyl)-imidazolidin-2-one-hydrochloride 1.7 g of 1-(1-benzyl-4-piperidinyl)-3-[4-[4-(methoxycarbonyl)-butyl]phenyl]-imidazolidin-2-one (also containing triphenylphosphineoxide and diethyl hydrazine-1,2-dicarboxylate) are hydrogenated in 50 ml of methanol in the presence of 0.5 g of palladium on activated charcoal (10% palladium) at ambient temperture under a hydrogen pressure of 50 psi. After 4.5 hours, a further 0.5 g of palladium catalyst are added and the mixture is hydrogenated for another 8 hours. The catalyst is filtered off, the filtrate is evaporated down, mixed with acetone and etherial hydrochloric acid and evaporated down once more. After stirring with acetone the product is suction filtered and dried.

Yield: 150 mg, $R_f$ value: 0.22 (Reversed Phase silica gel; Methanol/5% aqueous saline solution=6:4)

EXAMPLE 17

1-(trans-4-Carboxycyclohexyl)-3-[4-(4-piperidinyl)phenyl]-imidazolidin-2-one-hydrochloride 940 mg of 1-[trans-4-(ethoxycarbonyl)cyclohexyl]-3-[4-(1-trifluoroacetyl-4-piperidinyl)phenyl]-imidazolidin-2-one (also containing diethyl hydrazine-1,2-carboxylate), 10 ml of glacial acetic acid, 10 ml of water and 10 ml of concentrated hydrochloric acid are heated to 90° C. for 5.5 hours. Then the mixture is cooled, left to stand at ambient temperature for 2 days, evaporated down, mixed twice with water and again evaporated down and then stirred for 1.5 hours with 10 ml of water in an ice bath. The resulting precipitate is suction filtered, dried and stirred overnight with 20 ml of tert.butyl-methylether. The product is suction filtered, washed with tert.butyl-methylether and dried.

Yield: 47 mg, Melting point: 315°–320° C. (decomp.); $R_f$ value: 0.55 (Reversed Phase silica gel; Methanol/5% aqueous saline solution=6:4); Mass spectrum: M$^+$=371

The following compounds are obtained analogously to Example 17:
(1) 1-(4-carboxybutyl)-3-[4-(4-piperidinyl)phenyl] imidazolidine-2-one-hydrochloride Melting point: 245°–248° C. (decomp.); $R_f$ value: 0.49 (Reversed Phase Silica gel; methanol/5% aqueous saline solution 32 6:4); Calculated: C 59.75 H 7.39 N 11.00 Cl 9.28; Found: 59.38 7.41 10.84 9.02
(2) 1-(4-carboxyphenyl)-3-[4-(4-piperidinyl)phenyl] imidazolidin-2-one-hydrochloride×H$_2$O Melting point: >250° C.; Calculated: C 60.09 H 6.24 N 10.01 Cl 8.44; Found: 60.31 6.25 10.27 8.52; Mass spectrum: M$^+$=365

EXAMPLE 18

1-[4-(2-Carboxyethyl)cyclohexyl]-3-[2-(4-piperidinyl)ethyl]-imidazolidin-2-one-hydrochloride 400 mg of 1-[4-(2-carboxyethyl)phenyl]-3-[2-(4-piperidinyl)-ethyl]-imidazolidin-2-one-hydrochloride in 10 ml of glacial acetic acid are hydrogenated with 50 mg of platinum(IV) oxide under a hydrogen pressure of 3.4 bar for 13 hours at 60° C. The reaction mixture is filtered, the filtrate is evaporated down, taken up in a mixture of dilute hydrochloric acid and tetrahydrofuran, filtered and evaporated down again. The product is stirred with tetrahydrofuran and then with acetone and diethylether, suction filtered, washed with acetone and diethylether and dried.

Yield: 244 mg (58 % of theory), $R_f$ value: 0.49 (Reversed Phase Silica gel; methanol/5% aqueous saline solution=6:4)

The following compounds are obtained analogously to Example 18:
(1) 1-[4-(2-carboxyethyl)cyclohexyl]-3-[2-(4-piperidinyl)-ethyl]- 3a,4,5,6,7,7a-hexahydro-benzimidazol-2-one×1.6 HCl×1.8 H$_2$O $R_f$ value: 0.40 (Reversed Phase Silica gel; methanol/5% aqueous saline solution=6:4); Calculated: C 55.66 H 8.98 N 8.47 Cl 11.43; Found: 55.64 8.69 8.66 11.46
(2) 1-(trans)-4-carboxycyclohexyl-3-[4-(4-piperidinyl) cyclohexyl]-imidazolidin-2-one-hydrochloride Carried out in water with Rhodium/Platinum catalyst $R_f$ value: 0.55 (Reversed Phase Silica gel; methanol/5% aqueous saline solution=6:4); Mass spectrum: M$^+$=377

EXAMPLE 19

1-[4-[2-(n-Butylsulfonylamino)-2-(methoxycarbonyl)ethyl]-phenyl]-3-(4-cyanophenyl)-imidazolidin-2-one At ambient temperature, 495 mg of diethyl azodicarboxylate in 2 ml of acetonenitrile are rapidly added dropwise to 1.3 g of N-[4-[2-(n-butylsulfonylamino)-2-(methoxycarbonyl)-ethyl]phenyl]-N'-4-(cyanophenyl)-N-(2-hydroxyethyl)-urea and 0.71 g of triphenylphosphine in 8 ml of acetonitrile and then the mixture is stirred for 3.5 hours at ambient temperature. The precipitate is suction filtered, washed with a little acetonitrile and methanol and then dried.

Yield: 1.05 g (84% of theory), Melting point: 181°–183° C.

The following compounds are obtained analogously to Example 19:
(1) 1-(4-cyanophenyl)-3-[4-[2-(methoxycarbonyl)ethyl] phenyl]-imidazolidin-2-one Melting point: 162°–164° C.
(2) 1-[trans-4-(ethoxycarbonyl)cyclohexyl]-3-[4-(1-trifluoroacetyl-4-piperidinyl)phenyl]-imidazolidin-2-one Also contains diethyl hydrazine-1,2-dicarboxylate $R_f$ value: 0.60 (Silica gel; cyclohexane/ethyl acetate=2:1)
(3) 1-[4-(ethoxycarbonyl)phenyl]-3-[4-(1-trifluoroacetyl-4-piperidinyl)phenyl]-imidazolidin-2-one Melting point: 235°–239° C. (decomp.)
(4) 1-[4-(4-cyano-1-trifluoroacetyl-4-piperidinyl)phenyl]-3-[trans-4-(methoxycarbonyl)cyclohexyl]imidazolidin-2-one Carried out in dimethylformamide at 50° C.

$R_f$ value: 0.70 (Silica gel; ethyl acetate/cyclohexane=5:1)
(5) 1-[trans-4-(methoxycarbonyl)cyclohexyl]-3-[4-(1-trifluoroacetyl-4-piperidinyl)phenyl]-imidazolidin-2-one Carried out in dimethylformamide at 50° C.

$R_f$ value: 0.77 (Silica gel; ethyl acetate/cyclohexane=5:1)
(6) 1-[2-(1-tert.butyloxycarbonyl-4-piperidinyl)ethyl]-3-[4-[2-(n-butylsulfonylamino)-2-(methoxycarbonyl)ethyl]phenyl]-imidazolidin-2-one Melting point: 124°–126° C.; $R_f$ value: 0.42 (Silica gel; methylene chloride/ethyl acetate=7:3)
(7) 1-[2-(1-tert.butyloxycarbonyl-4-piperidinyl)ethyl]-2-cyanimino-3-[4-[2-(methoxycarbonyl)ethyl]phenyl]imidazolidine $R_f$ value: 0.27 (Silica gel; cyclohexane/ethyl acetate=3:7)
(8) 1-[2-(1-tert.butyloxycarbonyl-1-aza-4-cycloheptyl)ethyl]-3-[4-[2-(methoxycarbonyl)ethyl]phenyl]imidazolidin-2-one $R_f$ value: 0.38 (Silica gel; cyclohexane/ethyl acetate=1:1)
(9) 1-(1-benzyl-4-piperidinyl)-3-[4-[4-(methoxy-carbonyl)butyl]phenyl]-imidazolidin-2-one Also contains triphenylphosphine oxide and diethyl hydrazine-1,2-dicarboxylate.

$R_f$ value: 0.46 (Silica gel; methylene chloride/ethyl acetate/methanol=20:0.5:1.5)
(10) 1-[4-[2-(O,O'-diethylphosphono)ethyl]phenyl]-3-(2-(1-tert.butyloxycarbonyl-4-piperidinyl)ethyl]imidazolidin-2-one $R_f$ value: 0.35 (Silica gel; methylene chloride/ethylacetate/methanol=20:1:1)
(11) 1-[2-(1-tert.butyloxycarbonyl-4-piperidinyl)ethyl]-3-[2-cyano-4-[2-(methoxycarbonyl)ethyl]phenyl]-imidazolidine-2-one $R_f$ value: 0.63 (Silica gel; methylene chloride/ethyl acetate=1:1)

EXAMPLE 20

1-[4-[(1-Acetoxyethyl)oxycarbonylamidino]phenyl]-3-[4-[2-(isopropyloxycarbonyl)ethyl]phenyl]-imidazolidin-2-one 220 mg of 1-(4-amidinophenyl)-3-[4-[2-(isopropyloxycarbonyl)-ethyl]phenyl]-imidazolidin-2-one-hydrochloride, 190 mg of (1-acetoxyethyl)-(4-nitrophenyl)carbonate and 168 mg of N-ethyl-diisopropylamine are stirred in 20 ml of methylene chloride for 4 hours at ambient temperature. The reaction mixture is diluted with a little methylene chloride and then washed with ice water, twice with 0.2N sodium hydroxide solution and again with ice water. The organic phase is dried, evaporated down and the residue is stirred with tert.butylmethylether. The product is suction filtered, washed with a little tert.butylmethyl-ether and dried.

Yield: 250 mg (95 % of theory), $R_f$ value: 0.47 (Silica gel; methylene chloride/methanol=95:5); Calculated: C 61.82 H 6.15 N 10.68; Found: 61.69 6.21 10.63

The following compounds are obtained analogously to Example 20:
(1) 1-[4-[(acetoxymethyl)oxycarbonylamidino]phenyl]-3-[4-[2-(isopropyloxycarbonyl)ethyl]phenyl]-imidazolidin-2-one
(2) 2-[4-[(1-acetoxyethyl)oxycarbonylamidino]phenyl]-4-[4-[2-(cyclohexyloxycarbonyl)ethyl]phenyl]-5-methyl-4H-1,2,4-triazol-3-one
(3) 2-[4-[(acetoxymethyl)oxycarbonylamidino]phenyl]-4-[4-[2-(cyclohexyloxycarbonyl)ethyl]phenyl]-5-methyl-4H-1,2,4-triazol-3-one
(4) 4-[4-[2-(methoxycarbonyl)ethyl]phenyl]-5-methyl-2-[4-[(pivaloyloxymethyl)oxycarbonylamidino]phenyl]-4H-1,2,4-triazol-3-one
(5) 4-[4-[2-(cyclohexyloxycarbonyl)ethyl]phenyl]-2-[4-(methoxycarbonylamidino)phenyl]-5-methyl-4H-1,2,4-triazol-3-one
(6) 4-[4-[2-(cyclohexyloxycarbonyl)ethyl]phenyl]-2-[4-(ethoxycarbonylamidino)phenyl]-5-methyl-4H-1,2,4-triazol-3-one
(7) 2-[4-(benzyloxycarbonylamidino)phenyl]-4-[4-[2-(methoxycarbonyl)ethyl)phenyl]-5-methyl-4H-1,2,4-triazol-3-one
(8) 2-[4-[(1-acetoxyethyl)oxycarbonylamidino]phenyl]-4-[4-[2-(isopropyloxycarbonyl)ethyl]phenyl]-5-methyl-4H-1,2,4,triazol-3-one Melting point: from 167° C. (decomp.); $R_f$ value: 0.39 (Silica gel; methylene chloride/methanol=95:5); Calculated: C 60.33 H 5.81 N 13.03; Found: 60.25 5.86 13.25
(9) 2-[4-[(acetoxymethyl)oxycarbonylamidino]phenyl]-4-[4-[2-(isopropyloxycarbonyl)ethyl]phenyl]-5-methyl-4H-1,2,4,triazol-3-one Melting point: 152°–153° C. (decomp.); $R_f$ value: 0.45 (Silica gel; methylene chloride/methanol=95:5); Calculated: C 59.65 H 5.58 N 13.38; Found: 59.25 5.65 13.51
(10) 1-[trans-4-(methoxycarbonyl)cyclohexyl]-3-[4-(1-benzyloxycarbonyl-4-piperidinyl)phenyl]-imidazolidin-2-one Melting point: 145°–148° C.; $R_f$ value: 0.75 (Silica gel; methylene chloride/methanol=9:1)
(11) 1-(trans-4-carboxycyclohexyl)-3-[4-(1-benzyloxycarbonyl-4-cyano-4-piperidinyl)phenyl]-imidazolidin-2-one Carried out in water with sodium hydroxide solution as base.

Melting point: 238°–240° C.; $R_f$ value: 0.42 (Silica gel; methylene chloride/methanol=9:1)

EXAMPLE 21

1-[trans-4-[[1-(Cyclohexyloxycarbonyloxy)ethyl]oxycarbonyl]-cyclohexyl]-3-(4-(1-benzyloxycarbonyl-4-piperidinyl)phenyl]-imidazolidin-2-one 2.0 g of 1-(trans-4-carboxycyclohexyl)-3-[4-(1-benzyloxycarbonyl-4-piperidinyl)phenyl]-imidazolidin-2-one, 4.5 g of (1-chloroethyl)-cyclohexylcarbonate and 0.2 g of sodium iodide in 10 ml of dimethylsulfoxide are stirred for 1 hour at ambient temperature. 1.1 g of potassium carbonate are added and the mixture is stirred for 16 hours at 60° C. After cooling the reaction mixture is poured onto 100 ml of water, to which 1 ml of glacial acetic acid has been added. The mixture is extracted 3 times with ethyl acetate, the combined organic phases are washed with saline solution, dried and evaporated down. The residue is purified by chromatography over a silica gel column with cyclohexane/ethyl acetate (1:1).

Yield: 0.8 g (30 % of theory), $R_f$ value: 0.54 (Silica gel; cyclohexane/ethyl acetate=1:1); Mass spectrum: $M^+$=675

The following compounds are obtained analogously to Example 21:
(1) 2-[4-(benzyloxycarbonylamidino)phenyl]-5-methyl-4-[4-[2-[(pivaloyloxymethyl)oxycarbonyl]ethyl]phenyl]-4H-1,2,4-triazol-3-one Alkylating agent: chloromethyl pivalate
(2) 2-[4-(benzyloxycarbonylamidino)phenyl]-4-[4-[2-[[1-(cyclohexyloxycarbonyloxy)ethyl]oxycarbonyl]ethyl]phenyl]-5-methyl-4H-1,2,4-triazol-3-one (3) 1-[4-(1-benzyloxycarbonyl-4-piperidinyl)phenyl]-3-[trans-4-[(pivaloyloxymethyl)oxycarbonyl]cyclohexyl]imidazolidin-2-one Alkylating agent: chloromethyl pivalate
$R_f$ value: 0.50 (Silica gel; cyclohexane/ethyl acetate=1:1); Mass spectrum: M$^+$=619

(4) 1-[4-(1-benzyloxycarbonyl-4-piperidinyl)phenyl]-3-[trans-4-[[1-(ethyloxycarbonyloxy)ethyl]oxycarbonyl]-cyclohexyl]-imidazolidin-2-one Alkylating agent: (1-chloroethyl)-ethylcarbonate
$R_f$ value: 0.40 (Silica gel; cyclohexane/ethyl acetate=1:1)

EXAMPLE 22

1-[trans-4-(5-Indanyloxycarbonyl) cyclohexyl]-3-[4-(4-piperidinyl)phenyl]-imidazolidin-2-one×H$_2$O×0.85 HCl 1.0 g of 1-[trans-4-(5-indanyloxycarbonyl)cyclohexyl]-3-[4-(1-benzyloxycarbonyl-4-piperidinyl)phenyl]imidazolidin-2-one are hydrogenated for 2.5 hours in a mixture of 20 ml of tetrahydrofuran, 2 ml of water and 1.6 ml of 1N hydrochloric acid in the presence of 0.2 g of palladium on activated charcoal at ambient temperature under a hydrogen pressure of 50 psi. A further 0.2 g of catalyst and 1 mil of 1N hydrochloric acid are added and the mixture is hydrogenated for a further 2 hours. Then the catalyst is removed by suction filtering and the filtrate is washed several times with tetrahydrofuran/water/1N hydrochloric acid (20:1:1). The combined filtrates are adjusted to a pH of 7 with 1N sodium hydroxide solution and evaporated down. The resulting suspension is stirred for 1 hour in an ice bath. The solid matter is suction filtered, washed with a little ice water and dried.

Yield: 460 mg (54 % of theory), $R_f$ value: 0.40 (Silica gel; methylene chloride/methanol/conc. aqueous ammonia =4:1:0.2); Calculated: C 67.14 H 7.48 N 7.83 Cl 5.62; Found: 67.29 7.59 7.90 5.81; Mass spectrum: M$^+$=487

The following compounds are obtained analogously to Example 22:

(1) 2-(4-amidinophenyl)-5-methyl-4-[4-[2-[(pivaloyloxy methyl)oxycarbonyl]ethyl]phenyl]-4H-1, 2,4-triazol-3-one-hydrochloride (2) 2-(4-amidinophenyl)-4-[4-[2-[[1-(cyclohexyloxycarbonyloxy)ethyl]oxycarbonyl]ethyl]phenyl]-5-methyl-4H-1,2,4-triazol-3-one-hydrochloride (3) 1-[4-(4-piperidinyl)phenyl]-3-[trans-4-[(pivaloyloxymethyl)oxycarbonyl]cyclohexyl]-imidazolidin-2-one-hydrochloride $R_f$ value: 0.52 (Silica gel; methylene chloride/methanol/conc. aqueous ammonia=4:1:0.2); Mass spectrum: M$^+$=485

(4) 1-[trans-4-[[1-(ethyloxycarbonyloxy)ethyl]oxycarbonyl]-cyclohexyl]-3-[4-(4-piperidinyl)phenyl]imidazolidin-2-one-hydrochloride $R_f$ value: 0.50 (Silica gel; methylene chloride/methanol/conc. aqueous ammonia=4:1:0.2)

(5) 1-[trans-4-[[1-(cyclohexyloxycarbonyloxy)ethyl]oxycarbonyl]cyclohexyl]-3-[4-(4-piperidinyl)phenyl]imidazolidin-2-one-hydrochloride $R_f$ value: 0.45 (Silica gel; methylene chloride/methanol/conc. aqueous ammonia=4:1:0.2); Mass spectrum: M$^+$=541

(6) 1-[trans-4-(5-indanyloxycarbonyl)cyclohexyl]-3-[4-(4-cyano-4-piperidinyl)phenyl]-imidazolidin-2-one $R_f$ value: 0.30 (Silica gel; methylene chloride/methanol/conc. aqueous ammonia=4:1:0.2); Mass spectrum: M$^+$=512

EXAMPLE 23

2-[2-(1-tert.Butyloxycarbonyl-4-piperidinyl)ethyl]-4-[4-[2-(methoxycarbonyl)ethyl]phenyl]-5-methyl-4H-1,2,4-triazol-3-one To 1.1 g of 4-[4-[2-(methoxycarbonyl)ethyl]phenyl]-5-methyl-4H-1,2,4,-triazol-3-one in 6 ml of dimethylformamide are added 500 mg of potassium tert.butoxide and the mixture is stirred for 30 minutes at ambient temperature. It is then cooled in an ice bath and mixed with 1.3 g of 1-tert.butyloxycarbonyl-4-[2-(methane-sulfonyloxy)ethyl]piperidine. The mixture is then stirrred for 2 hours at ambient temperature. Ice water is added to the reaction mixture which is made neutral with citric acid solution. It is decanted off and the residue is digested with diethylether. The product is suction filtered, washed with water and dried.

Yield: 1.38 g (69% of theory), $R_f$ value: 0.61 (Silica gel; ethyl acetate)

The following compounds are obtained analogously to Example 23:

(1) 1-[2-(1-tert.butyloxycarbonyl-4-piperidinyl)ethyl]-3-[4-[2-(methoxycarbonyl)ethyl]phenyl]-imidazolidin-2-one Carried out in dimethylformamide with sodium hydride.
$R_f$ value: 0.41 (Silica gel; cyclohexane/ethyl acetate=1:1)

(2) 1-[2-(1-tert.butyloxycarbonyl-4-piperidinyl)ethyl]-3-[4-[2-(methoxycarbonyl)-1-pentyl]phenyl]-imidazolidin-2-one (3) 2-[2-(1-tert.butyloxycarbonyl-4-piperidinyl)ethyl]-4-[4-[2-(methoxycarbonyl)-1-pentyl]phenyll-5-methyl-4H-1,2,4-triazol-3-one $R_f$ value: 0.73 (Silica gel; ethyl acetate); Calculated: C 65.34 H 8.22 N 10.89; Found: 65.54 8.32 10.75

(4) 2-[2-(1-tert.butyloxycarbonyl-4-piperidinyl)ethyl]-4-[4-[2-(methoxycarbonyl)-3-methyl-1-butyl]phenyl]-5-methyl-4H-1,2,4-triazol-3-one (5) 2-[2-(1-tert.butyloxycarbonyl-4-piperidinyl)ethyl]-4-[4-[2-(methoxycarbonyl)-1-butyl]phenyl]-5-methyl-4H-1,2,4-triazol-3-one (6) 2-[2-(1-tert.butyloxycarbonyl-4-piperidinyl)ethyl]-4-[4-[2-(methoxycarbonyl)-1-propyl]phenyl]-5-methyl-4H-1,2,4-triazol-3-one (7) 1-[4-(methoxycarbonyl)butyl]-3-[4-(1-trifluoroacetyl-4-piperidinyl)phenyl]-imidazolidin-2-one Carried out in dimethylformamide with sodium hydride.
Melting point: 115°–117° C.; $R_f$ value: 0.73 (Silica gel; ethyl acetate/cyclohexane=4:1)

(8) 1-[4-(4-cyano-1-trifluoroacetyl-4-piperidinyl)phenyl]-3-[4-(methoxycarbonyl)butyl]-imidazolidin-2-one Carried out in dimethylformamide with sodium hydride.
$R_f$ value: 0.49 (Silica gel; ethyl acetate/cyclohexane=7:3)

(9) 2-[2-(1-tert.butyloxycarbonyl-4-piperidinyl)ethyl]-4-[4-[2-(methoxycarbonyl)ethyl]phenyl]-4H-1,2,4-triazol-3-one Melting point: 139°–141° C.; $R_f$ value: 0.58 (Silica gel; ethyl acetate/cyclohexane=7:3)

(10) 2-[2-(1-tert butyloxycarbonyl-4-piperidinyl)ethyl]-5-(4-[2-(methoxycarbonyl)ethyl]phenyl]-3,4-dihydro-2H,5H-1,2,5-thiadiazole-1,$_1$-dioxide Carried out in dimethylformamide with sodium hydride.
$R_f$ value: 0.41 (Silica gel; cyclohexane/ethyl acetate=1:1)

(11) 1-[(1-tert.butyloxycarbonyl-4-piperazinyl)carbonylmethyl]-3-[4-[2-(methoxycarbonyl)ethyl]phenyl]imidazolidin-2-one Carried out in dimethylforminamide with sodium hydride. (The (1-tert.butyloxycarbonyl-4-piperazinyl)-carbonylmethylchloride used as alkylating agent is obtained from 1-benzyl-piperazine by reacting with di-tert.butylpyrocarbonate, subsquently hydrogenating with palladium on activated charcoal and then reacting with chloroacetylchloride).

Melting point: 185°–187° C.; $R_f$ value: 0.44 (Silica gel; methylene chloride/ethyl acetate=1:1); Calculated: C 60.74 H 7.22 N 11.81; Found: 60.70 7.31 11.87

(12) 1-[2-(1-tert.butyloxycarbonyl-4-piperidinyl)ethyl]-3-[4-[2-(methoxycarbonyl)ethyl]phenyl]-3,4,5,6-tetrahydro-1H-pyrimidin-2-one Carried out in dimethylformamide with sodium hydride.

$R_f$ value: 0.36 (Silica gel; methylene chloride/methanol=200:3)

(13) 2-[2-(1-tert.butyloxycarbonyl-4-piperazinyl)ethyl]-4-[4-[2-(methoxycarbonyl)ethyl]phenyl]-4H-1,2,4-triazol-3-one The alkylating agent used (melting point: 238°–240° C.) is obtained from 1-(2-hydroxyethyl)piperazine by reacting with di-tert.butyl pyrocarbonate and subsequently reacting with methanesulphonic acid chloride in the presence of triethylamine.

Melting point: 128°–130° C.; $R_f$ value: 0.35 (Silica gel; ethyl acetate)

(14) 1-[4-[2-(methoxycarbonyl)ethyl]phenyl]-3-[2-(2,2,6,6-tetramethyl-4-piperidinyl)ethyl]-imidazolidin-2-one Carried out in dimethylformamide with sodium hydride.

Melting point: 127°–129° C.; $R_f$ value: 0.32 (Reversed Phase Silica gel; methanol/5% aqueous saline solution=6:4); Calculated: C 69.36 H 8.97 N 10.11; Found: 69.21 9.07 10.03

(15) 1-[4-[2-(methoxycarbonyl)ethyl]phenyl]-3-[2-(4-quinuclidinyl)ethyl]-imidazolidin-2-one×BH$_3$ Carried out in dimethylformamide with sodium hydride.

Melting point: 173°–176° C.; $R_f$ value: 0.56 (Silica gel; cyclohexane/ethyl acetate=2:8)

(16) 1-[2-(1-tert.butyloxycarbonyl-4-piperidinyl)ethyl]-3-[4-[2-(methoxycarbonyl)ethyl]phenyl]-hydantoin Carried out in dimethylformamide with sodium hydride.

Melting point: 104°–106° C.; $R_f$ value: 0.30 (Silica gel; cyclohexane/ethyl acetate=1:1); Calculated: C 63.41 H 7.45 N 8.87; Found: 63.66 7.49 8.95

(17) 3-[2-(1-tert.butyloxycarbonyl-4-piperidinyl)ethyl]-1-[4-[2-(methoxycarbonyl)ethyl]phenyl]-4,5-dimethyl-3H-imidazol-2-one Carried out in dimethylformamide with sodium hydride.

Melting point: 123°–125° C.; $R_f$ value: 0.39 (Silica gel; cyclohexane/ethyl acetate=2:8)

(18) 3-[2-(1-tert.butyloxycarbonyl-4-piperidinyl)ethyl]-1-[4-[2-(methoxycarbonyl)ethyl]phenyl]-hydantoin Carried out in dimethylformamide with sodium hydride.

Melting point: 97°–99° C.; $R_f$ value: 0.46 (Silica gel; cyclohexane/ethyl acetate=1:1)

(19) 1-[4-[2-(methoxycarbonyl)ethyl]phenyl]-3-[2-(1-tert.butyloxycarbonyl-4-piperidinyl)ethyl]-3H-benzimidazol-2-one Carried out in dimethylformamide with sodium hydride.

$R_f$ value: 0.33 (Silica gel; cyclohexane/ethyl acetate=6:4)

(20) 1-[4-[2-(methoxycarbonyl)ethyl]phenyl]-3-[2-(1-tert.butyloxycarbonyl-4-piperidinyl)ethyl]-4-methyl-imidazolidin-2-one Carried out in dimethylformamide with sodium hydride.

$R_f$ value: 0.58 (Silica gel; cyclohexane/ethyl acetate=1:1)

(21) 1-[2-(1-tert.butyloxycarbonyl-4-piperidinyl)ethyl]-3-[[4-(ethoxycarbonyl)-1-piperidinyl]carbonylmethyl)imidazolidin-2-one Carried out in dimethylformamide with sodium hydride. The alkylating agent ([4-(ethoxycarbonyl)-1-piperidinyl]-carbonyl]-methyl-chloride [$R_f$ value: 0.35 (Silica gel; cyclohexane/ethyl acetate=1:1)] is obtained by reacting ethyl piperidine-4-carboxylate with chloracetylchloride in the presence of triethylamine.

(22) 1-[2-(1-tert.butyloxycarbonyl-4-piperidinyl)ethyl-3-[4-[2-(methoxycarbonyl)ethenyl]-2-fluoro-phenyl]-imidazolidin-2-one Melting point: 120°–122° C.; $R_f$ value: 0.70 (Silica gel; cyclohexane/ethyl acetate=1:3)

(23) 1-[2-(1-tert.butyloxycarbonyl-4-piperidinyl)ethyl]-3-[4-[2-(methoxycarbonyl)ethenyl]-2-trifluoromethyl-phenyl]imidazolidin-2-one $R_f$ value: 0.54 (Silica gel; cyclohexane/ethyl acetate=1:2)

(24) 1-[2-(1-tert.butyloxycarbonyl-4-piperidinyl)ethyl]-3-[4-[2-(methoxycarbonyl)ethenyl]-2-methyl-phenyl]-imidazolidin-2-one $R_f$ value: 0.60 (Silica gel; cyclohexane/ethyl acetate=1:2)

(25) 1-[2-(1-tert.butyloxycarbonyl-4-piperidinyl)ethyl]-3-[4-[2-(methoxycarbonyl)ethenyl]phenyl]-imidazolidin-2-one Melting point: 148°–149° C.; $R_f$ value: 0.82 (Silica gel; methylene chloride/ethyl acetate=1:1)

(26) 1-[2-(1-tert.butyloxycarbonyl-4-piperidinyl)ethyl]-3-[4-[2-(ethoxycarbonyl)-1-phenyl-ethyl]phenyl]-imidazolidin-2-one Melting point: 100°–102° C.; $R_f$ value: 0.35 (Silica gel; methylene chloride/ethyl acetate=9:1)

(27) 1-(4-cyanobutyl)-3-[4-[2-(methoxycarbonyl)ethyl]phenyl]imidazolidin-2-one

Melting point: 99°–101° C.; $R_f$ value: 0.48 (Silica gel; ethyl acetate/cyclohexane=7:3)

(28) 1-[2-(1-tert.butyloxycarbonyl-3-pyrrolidinyl)ethyl-3-[4-[2-(methoxycarbonyl)ethyl]phenyl]-imidazolidin-2-one Melting point: 118°–119° C.; $R_f$ value: 0.50 (Silica gel; ethyl acetate/cyclohexane=7:3)

(29) 1-[2-(1-benzyl-1-azoniabicyclo[2.2.2]octan-4-yl)-ethyl]-3-[4-[2-(methoxycarbonyl)ethyl]phenyl]-imidazolidin-2-one chloride $R_f$ value: 0.16 (Silica gel; methylene chloride/methanol=9:1)

EXAMPLE 24

1-(trans-4-Carboxycyclohexyl)-3-[4-(4-cyano-4-piperidinyl)-phenyl]-imidazolidin-2-one To 1.4 g 1-[4-(4-cyano-1-trifluoroacetyl-4-piperidinyl)phenyl]-3-[trans-4-(methoxycarbonyl)cyclohexyl]-imidazolidin-2-one in 25 ml of tetrahydrofuran and 6 ml of water are added 2.8 ml of 2N sodium hydroxide solution and the mixture is stirred overnight. 5.6 ml of 1N hydrochloric acid are added, the tetrahydrofuran is evaporated off and the residue is adjusted to a pH of 7.0 using sodium hydroxide solution. It is stirred in an ice bath for 1 hour, the product is suction filtered, washed with a little ice water and with acetone and then dried.

Yield: 1.0 g (91 % of theory), $R_f$ value: 0.61 (Reversed Phase Silica gel; methanol/5% aqueous saline solution=6:4); Mass spectrum: M$^+$=396

The following compounds are obtained analogously to Example 24:

(1) 1-(4-carboxybutyl)-3-[4-(4-cyano-4-piperidinyl)-phenyl]-imidazolidin-2-one $R_f$ value: 0.62 (Reversed Phase Silica gel; methanol/5% aqueous saline solution=6:4); Mass spectrum: M$^+$=370

(2) 1-(trans-4-carboxycyclohexyl)-3-[4-(4-methyl-4-piperidinyl)phenyl]-imidazolidin-2-one $R_f$ value: 0.58 (Reversed Phase Silica gel; methanol/5% aqueous saline solution=6:4); Mass spectrum: M$^+$=385

(3) 1-[4-(1-aza-4-cycloheptyl)phenyl]-3-(trans-4-carboxycyclohexyl)-imidazolidin-2-one (4) 1-(4-carboxybicyclo[2.2.2]octan-1-yl)-3-[4-(4-piperidinyl)phenyl]-imidazolidin-2-one (5) 4-(trans-4-carboxycyclohexyl)-2-[4-(4-piperidinyl)-phenyl]-4H-1,2,4-triazol-3-one×1.1 H$_2$O Melting point: >220° C.; $R_f$ value: 0.59 (Reversed Phase Silica gel; methanol/5% aqueous saline solution=6:4); Calculated: C 61.55 H 7.28 N 14.36; Found: 61.88 7.28 14.06

(6) 4-(trans-4-carboxycyclohexyl)-2-[4-(4-piperidinyl)phenyl]-5-methyl-4H-1,2,4-triazol-3-one×H$_2$O Melting point: >220° C.; $R_f$ value: 0.54 (Reversed Phase Silica gel; methanol/5% aqueous saline solution=6:4); Calculated: C 62.67 H 7.51 N 13.92; Found: 62.85 7.73 12.65

(7) 1-(trans-4-carboxycyclohexyl)-3-[4-(4-piperidinyl)phenyl]-3H-imidazol-2-one×1.3 H$_2$O R$_f$ value: 0.58 (Reversed Phase Silica gel; methanol/5% aqueous saline solution=6:4); Calculated: C 64.20 H 7.59 N 10.69; Found: 64.13 7.56 10.78

(8) 1-(trans-4-carboxycyclohexyl)-3-[4-(4-piperidinyl)phenyl]-imidazolidin-2-one×0.2 H$_2$O Melting point: 327°–330° C. (decomp.); Calculated: C 67.25 H 7.90 N 11.20; Found: 67.19 7.95 11.50

EXAMPLE 25

1-[4-(4-Aminocarbonyl-4-piperidinyl)phenyl]-3-(trans-4-carboxycyclohexyl)-imidazolidin-2-one×0.8 H$_2$SO$_4$ 200 mg of 1-(trans-4-carboxycyclohexyl)-3-[4-(4-cyano-4-piperidinyl)phenyl]-imidazolidin-2-one are stirred with 2 ml of 85% sulphuric acid for 4 days at ambient temperature. Water is added, with cooling, the precipitate is suction filtered, washed with ice water and dried at 90° C. in vacuo.

Yield: 154 mg (54 % of theory), R$_f$ value: 0.65 (Reversed Phase Silica gel; methanol/5% aqueous saline solution 6:4); Calculated: C 53.60 H 6.46 N 11.36 S 5.20; Found: 53.68 6.76 11.23 5.89; Mass spectrum: (M+H)$^+$=415

EXAMPLE 26

1-[4-(2-Carboxyethyl)phenyl]-3-[2-(4-quinuclidinyl)ethyl]-imidazolidin-2-one-hydrochloride Hydogen chloride is passed over a mixture of 1.05 g of 1-[4-[2-(methoxycarbonyl)-ethyl]phenyl]-3-[2-(4-quinuclidinyl)ethyl]-imidazolidin-2-one×BH$_3$ and 1 ml of tetramethyl orthocarbonate in 35 ml of methanol, with stirring. The mixture is stirred at ambient temperature for 2½ days, then evaporated down and the residue is mixed with 10 ml of semi-concentrated hydrochloric acid. It is heated over a steam bath for three hours, cooled and evaporated to dryness. The residue is stirred with acetone, suction filtered, washed with acetone and ether and dried at 100° C.

Yield: 0.90 g (84 % of theory), Melting point: >250° C.; R$_f$ value: 0.49 (Reversed Phase Silica gel; methanol/5% aqueous saline solution=6:4); Calculated: C 61.83 H 7.41 N 10.30 Cl 8.69; Found: 61.56 7.34 10.38 8.42

The following compounds are obtained analogously to Example 26:

(1) 1-[2-(1-azabicyclo[2.2.1]heptan-4-yl)ethyl]-3-[4-(2-carboxyethyl)phenyl]-imidazolidin-2-one-hydrochloride (2) 1-(trans-4-carboxycyclohexyl)-3-[4-(4-quinuclidinyl)phenyl]-imidazolidin-2-one-hydrochloride

EXAMPLE 27

4-[trans-4-(Methoxycarbonyl)cyclohexyl]-2-[4-(1-trifluoroacetyl-4-piperidinyl)phenyl]-5-methyl-4H-1.2.4-triazol-3-one 8.0 g of 4-(4-iodophenyl)-1-trifluoroacetylpiperidine (approximately 90t strength), 4,5 g of 4-[trans-4-(methoxycarbonyl)cyclohexyl]-5-methyl-4H-1,2,4-triazol-3-one, 5.19 g of potassium carbonate, 0.59 ml of tris-[2-(2-methoxyethoxy)ethyl]-amine, 0.42 g of copper(I)-chloride, 0.42 g of copper(I)-iodide and 80 ml of N-methyl-pyrrolidinone are stirred for 1 hour at 170° C. under nitrogen. The mixture is cooled, suction filtered and washed with dimethylformamide. The filtrate is added to a silica gel column and eluted with cyclohexane/ethyl acetate (1:1). The product fractions are evaporated down and the residue is stirred with water overnight. The precipitate is suction filtered and dried at 100° C. in vacuo.

Yield: 650 mg (7 %. of theory), R$_f$ value: 0.30 (Silica gel; cyclohexane/ethyl acetate=1:1)

The following compound is obtained analogously to Example 27:

(1) 4-[trans-4-(methoxycarbonyl)cyclohexyl]-2-[4-(1-trifluoroacetyl-4-piperidinyl)phenyl]-4H-1,2,4-triazol-3-one Melting point: 184°–186° C.; R$_f$ value: 0.26 (Silica gel; cyclohexane/ethyl acetate=1:1)

EXAMPLE 28

1-[trans-4-(5-Indanyloxycarbonyl)cyclohexyl]-3-[4-(1-benzyloxycarbonyl-4-piperidinyl)phenyl]-imidazolidin-2-one 1.5 g of 1-(trans-4-carboxycyclohexyl)-3-[4-(1-benzyloxycarbonyl-4-piperidinyl) phenyl]-imidazolidin-2-one, 1.3 ml of thionylchloride and one drop of dimethylformamide are stirred for 2 hours at ambient temperature. Then the mixture is evaporated to dryness, the residue is dissolved in 5 ml of methylenechloride and combined, whilst cooling with ice, with a solution of 0.4 g of 5-indanole, a spatula tip of 4-dimethylaminopyridine and 0.7 ml of triethylamine in 5 ml of methylenechloride. After 5 hours' stirring at ambient temperature a further 0.8 g of 5-indanole and 2.1 ml of triethylamine are added and the mixture is stirred overnight. The reaction mixture is diluted with 50 ml of methylenechloride and extracted three times with water. The organic phase is separated off, dried and evaporated down. The residue is purified by chromatography over a silica gel column with methylenechloride/ethyl acetate/cyclohexane (1:1:1).

Yield: 1.57 g (85% of theory), Melting point: 172°–174° C.; R$_f$ value: 0.40 (Silica gel; cyclohexane/ethyl acetate/methylene chloride=2:1:1)

The following compound is obtained analogously to Example 28:

(1) 1-[trans-4-(5-indanyloxycarbonyl)cyclohexyl]-3-[4-(1-benzyloxycarbonyl-4-cyano-4-piperidinyl)phenyl]imidazolidin-2-one Melting point: 194°–196° C.; R$_f$ value: 0.27 (Silica gel; cyclohexane/ethyl acetate/methylene chloride=2:1:1)

EXAMPLE 29

1-[4-[2-(O-Ethylphosphono)ethyl]phenyl]-3-[2-(1-tert.butyloxvcarbonyl-4-pineridinvl)ethyl]-imidazolidin-2-one 2,0 g of 1-[4-[2-(O,O'-diethylphosphono)ethyl]phenyl]-3-[2-(1-tert.butyloxycarbonyl-4-piperidinyl)ethyl]imidazolidin-2-one and 0.56 g of sodium iodide are refluxed for 4 days in 20 ml of methylethylketone. The mixture is cooled, the solid matter is suction filtered, washed with methylethylketone and dried. The solid matter is dissolved in 15 ml of water and the solution is mixed with 10% potassium hydrogen sulphate solution until a pH of 2 is obtained. The mixture is cooled in an ice bath, the precipitate is suction filtered, washed with ice water and dried.

Yield: 1.1 g (58 % of theory), R$_f$ value: 0.16 (Reversed Phase Silica gel; methanol/5% aqueous saline solution=6:4)

EXAMPLE 30

1-[4-(2-Carboxyethyl)phenyl]-3-[2-(4-piperidinyl)ethyl]-4-methyl-imidazolidin-2-one×1.1 HCl×x 0.2 H$_2$O 260 mg of 1-[4-[2-(methoxycarbonyl)ethyl)phenyl]-3-[2-(1-tert.butyloxycarbonyl-4-piperidinyl)ethyl]-4-methyl-imidazolidin-2-one are heated to 90° C. with 2.2 ml of 3N hydrochloric acid for 6.5 hours. The reaction mixture is evaporated down, the residue is twice evaporated down with toluene and then triturated with acetone. The solid matter is suction filtered, washed with acetone and diethylether and dried at 60° C.

Yield: 200 mg (90 % of theory), Melting point: 180°–183° C.; R$_f$ value: 0.46 (Reversed Phase Silica gel; methanol/5% aqueous saline solution=6:4); Calculated: C 59.58 H 7.63 N 10.42 Cl 9.67; Found: 59.49 7.76 10.38 9.64

The following compounds are obtained analogously to Example 30:

(1) 1-(1-carboxymethyl-5-indanyl)-3-[2-(4-piperidinyl) ethyl]-imidazolidin-2-one-hydrochloride (2) 1-[4-(2-carboxyethyl)phenyl]-3-methyl-4-[2-(4-piperidinyl)ethyl]-imidazolidin-2-one-hydrochloride (3) 1-[4-(2-carboxy-1-phenyl-ethyl)phenyl]-3-[2-(4-piperidinyl)ethyl]-imidazolidin-2-one-hydrochloride $R_f$ value: 0.43 (Reversed Phase Silica gel; methanol/5% aqueous saline solution=6:4)

(4) 1-[trans-4-[(carboxymethyl)oxy]cyclohexyl]-3-[2-(4-piperidinyl)ethyl]-imidazolidin-2-one-hydrochloride×0.3 $H_2O$ Melting point: 207°–209° C. (decomp.); $R_f$ value: 0.64 (Reversed Phase Silica gel; methanol/5% aqueous saline solution=6:4); Calculated: C 54.69 H 8.31 N 10.63 Cl 8.97; Found: 54.39 8.21 10.63 9.33

(5) 1-[4-(2-carboxyethyl)-2-methyl-phenyl]-3-[2-(4-piperidinyl)ethyl]-imidazolidin-2-on-hydrochloride $R_f$ value: 0.57 (Reversed Phase Silica gel; methanol/5% aqueous saline solution=6:4); Mass spectrum: $M^+$=359

(6) 1-[4-(2-carboxyethyl)-3-chlorophenyl]-3-[2-(4-piperidinyl)ethyl]-imidazolidin-2-one-hydrochloride (7) 1-(2-carboxy-1,2,3,4-tetrahydro-6-naphthyl)-3-[2-(4-piperidinyl)ethyl]-imidazolidin-2-one-hydrochloride (8) 1-[4-(2-carboxyethyl)-2-fluorophenyl]-3-[2-(4-piperidinyl)ethyl]-imidazolidin-2-one-hydrochloride×0.5 $H_2O$ Melting point: 198°–200° C.; $R_f$ value: 0.58 (Reversed Phase Silica gel; methanol/5% aqueous saline solution=6:4); Calculated: C 55.80 H 6.90 N 10.27 Cl 8.67; Found: 55.86 6.68 10.56 9.01

(9) 1-[4-(2-carboxyethyl)-2-trifluoronethyl-phenyl]-3-[2-(4-piperidinyl)ethyl]-iiuidazolidin-2-one-hydrochloride $R_f$ value: 0.50 (Reversed Phase Silica gel; methanol/5% aqueous saline solution=6:4)

(10) 1-(trans-4-carboxycyclohexyl)-3-[4-[(2-aminoethyl)oxy]-phenyl]-imidazolidin-2-one-hydrochloride

(11) 1-[4-(2-carboxyethyl)phenyl]-3-methyl-4-[(4-piperidinyl)oxymethyl]-imidazolidin-2-one-hydrochloride

(12) 1-[4-(2-carboxyethyl)phenyl]-3-(2-(2-oxo-1-piperazinyl)-ethyl]-imidazolidin-2-one-hydrochloride

(13) 1-[4-(2-carboxyethyl)phenyl]-3-[2-(3-pyrrolidinyl)ethyl]-imidazolidin-2-one-hydrochloride×0.25 $H_2O$ Melting point: 200°–203° C.; $R_f$ value: 0.57 (Reversed Phase Silica gel; methanol/5% aqueous saline solution=6:4); Calculated: C 58.06 H 7.17 N 11.28 Cl 9.52; Found: 57.97 7.12 11.28 9.73

(14) 1-[4-(2-carboxyethyl)phenyl]-3-[3-(3-piperidinyl)propyl]-imidazolidin-2-one-hydrochloride

(15) 1-[4-(2-carboxyethenyl)phenyl]-3-[2-(4-piperidinyl)ethyl]-imidazolidin-2-one-hydrochloride×1 $H_2O$ Melting point: 307°–310° C. (decomp.); $R_f$ value: 0.50 (Reversed Phase Silica gel; tetrahydrofuran/water=5:4); Calculated: C 57.35 H 7.09 N 10.56; Found: 57.49 7.15 10.60; Mass spectrum: $M^+$=343

(16) 1-[4-(2-carboxyethyl)-2-cyano-phenyl]-3-[2-(4-piperidinyl)ethyl]-imidazolidin-2-one-hydrochloride $R_f$ value: 0.71 (Reversed Phase Silica gel; methanol/5% aqueous saline solution=6:4)

(17) 1-[1-(2-carboxyethyl)-piperidin-4-yl]-3-[2-(4-piperidinyl)ethyl]-imidazolidin-2-one-dihydrochloride

EXAMPLE 31

1-[4-(2-Phosphonoethyl)phenyl]-3-[2-(4-piperidinyl)ethyl]-imidazolidin-2-one×1.5 $H_2O$ 450 mg of 1-[4-[2-(O-ethyl-phosphono)ethyl]phenyl]-3-[2-(4-piperidinyl)ethyl]-imidazolidin-2-one×0.9 HCl×1.1 $H_2O$, 22.5 ml of methylenechloride and 0.9 ml of bromotrimethylsilane are refluxed for 3 hours. The mixture is evaporated to dryness, the residue obtained is dissolved in 15 ml of water and adjusted to pH 7 with 1N sodium hydroxide solution. The precipitate obtained is suction filtered, washed with water and dried.

Yield: 260 mg (70 % of theory), $R_f$ value: 0.58 (Reversed Phase Silica gel; methanol/5% aqueous saline solution=6:4); Calculated: C 52.93 H 7.65 N 10.28; Found: 52.80 7.48 10.34

EXAMPLE 32

1-(2-Cyano-1,2,3,4-tetrahydro-6-naphthyl)-3-[trans-4-(methoxycarbonyl)cyclohexyl]-3H-imidazol-2-one 2.5 g of N-(2-cyano-1,2,3,4-tetrahydro-6-naphthyl)-N'-(2,2-diethoxyethyl)-N'-[trans-4-(methoxycarbonyl)cyclohexyl]- urea are dissolved in 20 ml trifluoroacetic acid and refluxed for 2.5 hours. Then, the mixture is cooled, evaporated down to dryness and the residue is taken up in 75 ml water and neutralized with 2N sodium hydroxide solution. The solid material obtained is suction filtered, washed with water, dried and purified by chromatography over a silica gel column with ethyl acetate/methylene chloride/cyclohexane (1:1:1).

Yield: 1.4 g (70% of theory); Melting point: 175°–176° C.; $R_f$ value: 0.34 (Silica gel; ethyl acetate/cyclohexane=3:2)

The following compounds are obtained analogously to Example 32:

(1) 1-[2-(methoxycarbonyl)-6-naphthyl]-3-[2-(4-piperidinyl)ethyl]-3H-imidazol-2-one-trifluoroacetate With simultaneous cleavage of the N-tert.butyloxycarbonyl protecting group.

Melting point: 148°–151° C.; $R_f$ value: 0.38 (Reversed Phase Silica gel; methanol/5% aqueous saline solution=6:4); Calculated: C 58.41 H 5.31 N 8.51; Found: 58.47 5.39 8.51

(2) 1-[2-(methoxycarbonyl)-1,2,3,4-tetrahydro-6-naphthyl]-3-[2-(4-piperidinyl)ethyl]-3H-imidazol-2-one With simultaneous cleavage of the N-tert.butyloxycarbonyl protecting group; isolation of the base Melting point: 116°–118° C.; $R_f$ value: 0.50 (Reversed Phase Silica gel; methanol/5% aqueous saline solution=6:4)

(3) 1-(trans-4-(methoxycarbonyl)cyclohexyl]-3-[4-(4-quinuclidinyl)phenyl]-3H-imidazol-2-one Isolation of the base Melting point: 223°–225° C.; $R_f$ value: 0.47 (Reversed Phase Silica gel; methanol/5% aqueous saline solution=6:4); Mass spectrum: $M^+$=409

(4) 1-[trans-4-(methoxycarbonyl)cyclohexyl]-3-[4-(4-methyl- 1-trifluoroacetyl-4-piperidinyl)phenyl]-3H-imidazol-2-one Melting point: 182°–184° C.; $R_f$ value: 0.44 (Silica gel; methylene chloride/ethyl acetate=4:1)

(5) 1-(4-cyano-bicyclo[2.2.2]octan-1-yl)-3-[4-[2-(methoxycarbonyl)ethyl]phenyl]-imidazolidin-2-one Melting point: 195°–197° C.; $R_f$ value: 0.68 (Silica gel; methylene chloride/ethyl acetate=4:1)

(6) 1-[2-(1-benzyl-l-azoniabicyclo[2.2.2]octan-4-yl)ethyl]-3-[-4-[2-(methoxycarbonyl)ethyl]phenyl]-3H-imidazol-2-one-chloride $R_f$ value: 0.19 (Silica gel; methylene chloride/methanol= 100:7)

EXAMPLE 33

1-[2-(1-tert.butyloxycarbonyl-4-piperidinyl)ethyl]-3-[4-[2-(methoxycarbonyl)ethyl]-2-fluoro-phenyl]-imidazolidin-2-one 2.0 g of 1-[2-(1-tert.butyloxycarbonyl-4-piperidinyl)-ethyl]-3-[4-[2-(methoxycarbonyl)ethenyl]-2-fluoro-phenyl]

-imidazolidin-2-one is hydrogenated with 0.5 g of 10% palladium on charcoal in 20 ml of ethyl acetate for 15 minutes at ambient temperature and a hydrogen pressure of 50 psi. The mixture is suction filtered and the filtrate is evaporated to dryness.

Yield: 2.0 g (100% of theory); $R_f$ value: 0.65 (Silica gel; ethyl acetate/cyclohexane=3:1)

The following compounds are obtained analogously to Example 33:

(1) 1-[2-(1-tert.butyloxycarbonyl-4-piperidinyl)ethyl]-3-[4-[2-(methoxycarbonyl)ethyl]-2-trifluoromethyl-phenyl]-imidazolidin-2-one $R_f$ value: 0.50 (Silica gel; ethyl acetate/cyclohexane=2:1)

(2) 1-[2-(1-tert.butyloxycarbonyl-4-piperidinyl)-ethyl]-3-[4-[2-(methoxycarbonyl)ethyl]-2-methyl-phenyl]-imidazolidin-2-one $R_f$ value: 0.60 (Silica gel; ethyl acetate/cyclohexane=2:1)

EXAMPLE 34

1-[4-[(Cyanomethyl)oxy]phenyl]-3-[trans-4-(methoxycarbonyl)cyclohexyl]-imidazolidin-2-one 270 mg of potassium carbonate and 210 mg of bromoacetonitrile are added to a solution of 500 mg of 1-(4-hydroxyphenyl)-3-[trans-4-(methoxycarbonyl)-cyclohexyl]-imidazolidin-2-one in 3 ml of dimethyl-formamide and heated for 5.5 hours at 60° C. The mixture is evaporated down. The residue is taken up in water, neutralized with 2N citric acid and extracted 4 times with ethyl acetate. The combined organic phases are washed with water, dried and evaporated down in vacuo. The residue is purified by chromatography over a silica gel column with methylene chloride/ethyl acetate (100:8).

Yield: 370 mg (65% of theory); Melting point: 136°–138° C.; $R_f$ value: 0.33 (Silica gel; ethyl acetate/cyclohexane=1:1)

EXAMPLE 35
Dry Ampoule Containing 2.5 mg of Active Substance per 1 ml

| Composition: | |
|---|---|
| Active substance | 2.5 mg |
| Mannitol | 50.0 mg |
| Water for injections ad | 1.0 ml |

Preparation:

Active substance and mannitol are dissolved in water. After transferring the solution to the ampoule, it is freeze-dried.

At the point of use, the solution is made up with water for injections.

EXAMPLE 36
Dry Ampoule Containing 35 mg of Active Substance per 2 ml

| Composition: | |
|---|---|
| Active substance | 35.0 mg |
| Mannitol | 100.0 mg |
| Water for injections ad | 2.0 ml |

Preparation: active substance and mannitol are dissolved in water. After transferring the solution to the ampoule, it is freeze-dried.

At the point of use, the solution is made up with water for injections.

EXAMPLE 37
Tablet Containing 50 mg of Active Substance

| Composition: | |
|---|---|
| (1) Active substance | 50.0 mg |
| (2) Lactose | 98.0 mg |
| (3) Corn starch | 50.0 mg |
| (4) Polyvinylpyrrolidone | 15.0 mg |
| (5) Magnesium stearate | 2.0 mg |
| | 215.0 mg |

Preparation: (1), (2) and (3) are mixed together and granulated with an aqueous solution of (4). (5) is mixed with the dried granules. From this mixture, compressed tablets are produced, biplanar, facetted on both sides and notched on one side. Diameter of tablets: 9 mm.

EXAMPLE 38
Tablet Containing 350 mg of Active Substance

| Composition: | |
|---|---|
| (1) Active substance | 350.0 mg |
| (2) Lactose | 136.0 mg |
| (3) Corn starch | 80.0 mg |
| (4) Polyvinylpyrrolidone | 30.0 mg |
| (5) Magnesium stearate | 4.0 mg |
| | 600.0 mg |

Preparation: (1), (2) and (3) are mixed together and granulated with an aqueous solution of (4). (5) is mixed with the dried granules. From this mixture, compressed tablets are produced, biplanar, facetted on both sides and notched on one side. Diameter of tablets: 12 mm.

EXAMPLE 39
Capsule Containing 50 mg of Active Substance

| Composition: | |
|---|---|
| (1) Active substance | 50.0 mg |
| (2) Dried corn starch | 58.0 mg |
| (3) Powdered lactose | 50.0 mg |
| (4) Magnesium stearate | 2.0 mg |
| | 160.0 mg |

Preparation: (1) is triturated with (3). This triturate is added to the mixture of (2) and (4), with thorough mixing.

This powdered mixture is packed into size 3 hard gelatin oblong capsules in a capsule filling machine.

EXAMPLE 40
Capsule Containing 350 mg of Active Substance

| Composition: | |
|---|---|
| (1) Active substance | 350.0 mg |
| (2) Dried corn starch | 46.0 mg |
| (3) Powdered lactose | 30.0 mg |
| (4) Magnesium stearate | 4.0 mg |
| | 430.0 mg |

Preparation: (1) is triturated with (3). This triturate is added to the mixture of (2) and (4), with thorough mixing.

This powdered mixture is packed into size 0 hard gelatin oblong capsules in a capsule filling machine.

What is claimed is:

1. A cyclic urea derivative of formula

 (I)

wherein

X is a carbonyl group;

Y is a —CH$_2$CH$_2$— group optionally substituted by R$_c$ or by R$_c$ and R$_d$, wherein
R$_c$ is a hydrogen atom or a methyl, trifluoromethyl or phenyl group, and
R$_d$ is a hydrogen atom or a methyl group;

R$_a$ is a group of the formula

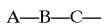

(wherein A together with B is a piperidinyl group wherein the hydrogen atom in the 1-position together with a hydrogen atom in the 2-position is replaced by a straight-chained C$_{3-4}$-alkylene group, or a piperidinyl group in which the hydrogen atom in the 1-position together with a hydrogen atom in the 3-position is replaced by a straight-chained C$_{2-4}$-alkylene group, or a piperidinyl group in which the hydrogen atom in the 1-position together with a hydrogen atom in the 4-position is replaced by a straight-chained C$_{1-3}$-alkylene group, whilst a 4-position bound methylene group of an ethylene chain may be replaced by a hydroxymethylene or carbonyl group; and C is a C$_{1-4}$-alkylene group)

R$_b$ is a group of the formula

(wherein D is a 1,3- or 1,4-phenylene group optionally substituted by a fluorine or chlorine atom or by a methyl, trifluoromethyl or cyano group, or a 1,4-cyclohexylene group;

E is a C$_{1-4}$-alkylene group which may be substituted by a C$_{1-4}$-alkyl group, by a phenyl group or by a C$_{1-4}$-alkylsulphonylamino group;

F is a carbonyl group which is substituted by a hydroxy group, by a C$_{1-5}$-alkoxy group, by a phenylalkoxy group having 1 to 3 carbon atoms in the alkoxy moiety or by an R$_7$O— group, wherein
R$_7$ is a C$_{5-7}$-cycloalkyl group or a cyclohexylmethyl or indanyl group, or F is an R$_8$CO—O—CHR$_9$—O—CO— group, wherein
R$_8$ is a cycloalkyloxy group having 5 to 7 carbon atoms in the cycloalkyl moiety, an alkyl or alkoxy group each having 1 to 4 carbon atoms, and
R$_9$ is a hydrogen atom or a methyl group)

and the shortest distance between the group F and the furthest removed nitrogen atom of the groups A—B—C— amounts to at least 11 bonds;

a tautomer thereof, a stereoisomer thereof or a salt thereof.

2. The cyclic urea derivative of formula I as claimed in claim 1, wherein

A together with B is a piperidinyl group wherein the hydrogen atom in the 1-position together with a hydrogen atom in the 4-position is replaced by a straight-chained C$_{1-3}$-akylene group, whilst the 4-position bound methylene group of an ethylene chain may be replaced by a hydroxymethylene or carbonyl group;

a tautomer thereof, a stereoisomer thereof or a salt thereof.

3. The cyclic urea derivative of formula I according to claim 1 wherein

X is a carbonyl group;

Y is a —CH$_2$CH$_2$— group optionally substituted by R$_c$ or by R$_c$ and R$_d$, wherein
R$_c$ is a hydrogen atom or a methyl, trifluoromethyl or phenyl group, and
R$_d$ is a hydrogen atom or a methyl group;

R$_a$ is a group of the formula

(wherein A together with B is a piperidinyl group wherein the hydrogen atom in the 1-position together with a hydrogen atom in the 4-position is replaced by methylene, ethylene or 1,3-propylene group; and C is a —CH$_2$CH$_2$— group) and R$_b$ is a group of the formula

(wherein D is a 1,4-phenylene group optionally substituted by a fluorine atom or by a methyl, trifluoromethyl or cyano group, or a 1,4-cyclohexylene group;

E is a straight-chained C$_{2-4}$-alkylene group optionally substituted by a C$_{1-4}$-alkyl group, by a phenyl group or by a C$_{1-4}$-alkylsulphonylamino group; and F is a carbonyl group which is substituted by a hydroxy group, by a C$_{1-4}$-alkoxy group or by an R$_7$O— group, wherein
R$_7$ is a cyclopentyl, cyclohexyl or 5-indanyl group, or F is an R$_8$CO—O—CHR$_9$—O—CO— group, wherein
R$_8$ is a tert.butyl, ethoxy or cyclohexyloxy group and
R$_9$ is a hydrogen atom or a methyl group)

and the shortest distance between the group F and the furthest removed nitrogen atom of the groups A—B—C— amounts to at least 11 bonds;

a tautomer thereof, a stereoisomer thereof or a salt thereof.

4. The cyclic urea derivative of formula I according to claim 1 wherein

X is a carbonyl group;

Y is a —CH$_2$CH$_2$— group optionally substituted by R$_c$ or by R$_c$ and R$_d$, wherein
R$_c$ is a hydrogen atom or a methyl, trifluoromethyl or phenyl group, and
R$_d$ is a hydrogen atom or a methyl group;

R$_a$ is a group of the formula

(wherein A together with B is a piperidinyl group wherein the hydrogen atom in the 1-position together with a hydrogen atom in the 4-position is replaced by methylene or ethylene group; and C is a —CH$_2$CH$_2$— group) and R$_b$ is a group of the formula

(wherein D is a 1,4-phenylene group optionally substituted by a fluorine atom or by a methyl, trifluoromethyl or cyano group, or a 1,4-cyclohexylene group;

E is a straight-chained $C_{2-4}$-alkylene group optionally substituted by a $C_{1-4}$-alkyl group, by a phenyl group or by a $C_{1-4}$-alkylsulphonylamino group; and F is a carbonyl group which is substituted by a hydroxy group, by a $C_{1-4}$-alkoxy group or by an $R_7O$— group, wherein $R_7$ is a cyclopentyl, cyclohexyl or 5-indanyl group, or F is an $R_8CO$—O—$CHR_9$—O—CO— group, wherein $R_8$ is a tert.butyl, ethoxy or cyclohexyloxy group and $R_9$ is a hydrogen atom or a methyl group)

and the shortest distance between the group F and the furthest removed nitrogen atom of the groups A—B—C— amounts to at least 11 bonds;

a tautomer thereof, a stereoisomer thereof or a salt thereof.

5. The cyclic urea derivative of formula I according to claim 1 wherein

X is a carbonyl group;

Y is a —$CH_2CH_2$— group optionally substituted by $R_c$ or by $R_c$ and $R_d$, wherein $R_c$ is a hydrogen atom or a methyl, trifluoromethyl or phenyl group, and $R_d$ is a hydrogen atom or a methyl group;

$R_a$ is a group of the formula

A—B—C—

(wherein A together with B is a 4-quinuclidinyl group, and C is a —$CH_2CH_2$— group) and $R_b$ is a group of the formula

F—E—D—

(wherein D is a 1,4-phenylene or 1,4-cyclohexylene group;

E is an ethylene group; and

F is a carbonyl group which is substituted by a hydroxy group, by a $C_{1-4}$-alkoxy group or by an $R_7O$— group, wherein $R_7$ is a cyclopentyl or cyclohexyl group;

and the shortest distance between the group F and the furthest removed nitrogen atom of the groups A—B—C— amounts to at least 11 bonds;

a tautomer thereof, a stereoisomer thereof or a salt thereof.

6. The cyclic urea derivative of formula I according to claim 1 selected from the group:

(a) 1-[4-(2-carboxyethyl)phenyl]-3-[2-(4-quinuclidinyl)ethyl]-imidazolidin-2-one, (b) 1-[(trans-4-(2-carboxyethyl)-cyclohexyl]-3-[2-(4-quinuclidinyl)ethyl]-imidazolidin-2-one, and (c) 3-[4-(2-carboxyethyl)phenyl]-1-[2-(1-azabicyclo[2.2.1]heptan-4-yl)ethyl]-imidazolidin2-one, or a $C_{1-3}$-alkyl ester thereof or a salt thereof.

7. 1-[4-(2-carboxyethyl)phenyl]-3-[2-(4-quinuclidinyl)ethyl]-imidazolidin-2-one, or the ethyl ester or a salt thereof.

* * * * *